United States Patent
Millis et al.

(10) Patent No.: US 7,718,417 B2
(45) Date of Patent: May 18, 2010

(54) PRODUCTION OF ISOPRENOIDS

(75) Inventors: James R. Millis, Kohler, WI (US); Julie Maurina-Brunker, Appleton, WI (US); Thomas W. McMullin, Manitowoc, WI (US)

(73) Assignee: Bio-Technical Resources, a division of Arkion Life Sciences, LLC, New Castle, DE (US)

( * ) Notice: Subject to any disclaimer, the term of this patent is extended or adjusted under 35 U.S.C. 154(b) by 0 days.

(21) Appl. No.: 11/752,933

(22) Filed: May 24, 2007

(65) Prior Publication Data

US 2007/0231861 A1    Oct. 4, 2007

Related U.S. Application Data

(63) Continuation of application No. 10/719,196, filed on Nov. 20, 2003, now abandoned, which is a continuation of application No. 09/909,558, filed on Jul. 20, 2001, now Pat. No. 6,689,593, which is a continuation of application No. 09/350,275, filed on Jul. 6, 1999, now Pat. No. 6,531,303.

(60) Provisional application No. 60/091,964, filed on Jul. 6, 1998.

(51) Int. Cl.
C12N 1/19      (2006.01)
C12P 23/00     (2006.01)
C12P 5/02      (2006.01)

(52) U.S. Cl. ............ 435/254.2; 435/320.1; 435/254.21; 435/67; 435/167; 435/189; 435/183

(58) Field of Classification Search ........................ None
See application file for complete search history.

(56) References Cited

U.S. PATENT DOCUMENTS

| | | | |
|---|---|---|---|
| 3,862,988 A | 1/1975 | Pond | |
| 3,917,710 A | 11/1975 | Pond et al. | |
| 4,305,876 A | 12/1981 | Barner et al. | |
| 4,871,721 A | 10/1989 | Biller | |
| 5,349,097 A | 9/1994 | Thome et al. | |
| 5,429,939 A | 7/1995 | Misawa et al. | |
| 5,460,949 A | 10/1995 | Saunders et al. | |
| 5,530,189 A | 6/1996 | Ausich et al. | |
| 5,545,816 A | 8/1996 | Ausich et al. | |
| 5,589,372 A | 12/1996 | Robinson | |
| 5,599,711 A | 2/1997 | Fleno et al. | |
| 5,656,472 A | 8/1997 | Ausich et al. | |
| 5,684,238 A | 11/1997 | Ausich et al. | |
| 5,705,624 A | 1/1998 | Fitzmaurice et al. | |
| 5,723,497 A | 3/1998 | Ohashi et al. | |
| 5,744,341 A | 4/1998 | Cunningham, Jr. et al. | |
| 5,766,911 A | 6/1998 | Koike et al. | |
| 5,919,818 A | 7/1999 | Lane et al. | |
| 6,242,227 B1 | 6/2001 | Millis et al. | |
| 6,410,755 B1 | 6/2002 | Millis et al. | |
| 6,524,811 B1 | 2/2003 | Cunningham, Jr. et al. | |
| 6,531,303 B1 | 3/2003 | Millis et al. | |
| 6,689,593 B2 | 2/2004 | Millis et al. | |
| 7,129,392 B2 | 10/2006 | Hahn et al. | |
| 7,172,886 B2 | 2/2007 | Keasling et al. | |
| 2002/0086380 A1 | 7/2002 | Cunningham, Jr. | |
| 2003/0125573 A1 | 7/2003 | Millis et al. | |
| 2003/0220405 A1 | 11/2003 | Cunningham, Jr. | |
| 2004/0110257 A1 | 6/2004 | Millis et al. | |
| 2007/0161712 A1 | 7/2007 | Cunningham | |
| 2007/0238157 A1 | 10/2007 | Millis et al. | |
| 2007/0238159 A1 | 10/2007 | Millis et al. | |
| 2007/0238160 A1 | 10/2007 | Millis et al. | |
| 2007/0254354 A1 | 11/2007 | Millis et al. | |

FOREIGN PATENT DOCUMENTS

| | | |
|---|---|---|
| DE | 2404621 | 8/1975 |
| EP | 209158 | 1/1987 |
| EP | 0283946 | 9/1988 |
| EP | 393690 | 10/1990 |
| EP | 486290 | 5/1992 |
| EP | 769551 | 4/1997 |
| EP | 955363 | 11/1999 |
| GB | 1479272 | 7/1977 |
| JP | 61236737 | 10/1986 |
| JP | 63063674 | 3/1988 |
| JP | 63179850 | 7/1988 |
| JP | 5-192184 | 8/1993 |
| JP | 8-242861 | 9/1996 |
| WO | WO 94/21595 | 9/1994 |
| WO | WO 96/28545 | 9/1996 |
| WO | WO 97/23633 | 7/1997 |
| WO | WO 97/36998 | 10/1997 |
| WO | WO 00/01649 | 1/2000 |
| WO | WO 00/01650 | 1/2000 |

OTHER PUBLICATIONS

Mueller C. et al, Properties and inhibition of the first two enzymes of the non-mevalonate pathway of isoprenoid synthesis. Biochem. Soc. Trans. 28, 792-793, 2000; abstract.*

Lange B, M. et al. Isoprenoid synthesis via a Mevalonate-independent Pathway in Plantrs: Cloning and Heterologous Expression of 1-Deoxy-D-xylulose-5-phosphate Reductoisomerase from Peppermint, Arch. Biochem. Biophys. 365, 170-174, 1999; abstract.*

M. Harker et al. "Expression of Prokaryotic 1-Deoxy-D-xylulose-5-phosphatases in *Escherichia coli* Increases Carotenoid and Ubiqinone Biosynthesis", FEBS Letters 488:115-119 (Apr. 1999).*

M. Albrecht et al. "Metabolic Engineering of the Terpenoid Biosynthetic Pathway of *Escherichia coli* for Production of the Carotenoids Beta-Carotene and Zeaxanthin", Biotechnology letters 21: 791-795 (1999).*

(Continued)

*Primary Examiner*—Rebecca Prouty
(74) *Attorney, Agent, or Firm*—Sheridan Ross P.C.

(57) ABSTRACT

The invention provides a biological method of producing isoprenoids.

4 Claims, 11 Drawing Sheets

OTHER PUBLICATIONS

Official Action for U.S. Appl. No. 11/752,931, mailed Oct. 9, 2008.
Dyck et al., Trends, Biotechnol. 21: 394-399, 2003.
Vain et al., Theor Appl. Genet 105: 878-889, 2002.
Extended European Search Report for European Patent Application No. 08003596.7, dated Sep. 9, 2008.
Partial European Search Report for European Patent Application No. 08003596.7, dated Jun. 19, 2008.
Official Action for U.S. Appl. No. 11/645,155, mailed Jun. 6, 2008.
Official Action for U.S. Appl. No. 11/753,399, mailed Jul. 16, 2008.
Bailey et al. "Toward a Science of Metabolic Engineering" Science. Jun. 21, 1991 ;252(5013)1668-75. Review.
Bowman et al. UniProtKB Database—Accession P54839. 1996.
Lee et al. Sequential delta-integration for the regulated insertion of cloned genes in *Saccharomyces cerevisiae*. Biotechnol Prog. Jul.-Aug. 1997;13(4):368-73.
Maeng et al. Expression, purification, and characterization of the dihydrolipoamide dehydrogenase-binding protein of the pyruvate dehydrogenase complex from *Saccharomyces cerevisiae*. Biochemistry. Nov. 22, 1994;33(46):13801-7.
Pronk et al. Pyruvate metabolism in *Saccharomyces cerevisiae*. Yeast. Dec. 1996;12(16):1607-33. Review.
Szkopinska et al. "Polyprenol Formation in the Yeast *Saccharomyces cerevisiae*: Effect of Farnesyl Diphosphate Synthase Overexpression", J. Lipid Research 38(5): 962-968 (May 1997).
Whisstock et al. "Prediction of Protein Function From Protein Sequence and Structure", Quarterly Reviews of Biophysics 36: 307-340 (2003).
Official Action for U.S. Appl. No. 11/752,931, mailed May 14, 2009.
Official Action for U.S. Appl. No. 11/753,254, mailed Apr. 15, 2009.
Official Action for U.S. Appl. No. 11/753,301, mailed Apr. 20, 2009.
Official Action for U.S. Appl. No. 11/753,399, mailed May 26, 2009.
"IMAGE: Mevalonate pathway", Wikipedia, downloaded Mar. 22, 2007, 2 pages.
"Mevalonate pathway", Wikipedia, downloaded Mar. 22, 2007, 3 pages.
"Non-mevalonate pathway", Wikipedia, downloaded Mar. 22, 2007, 2 pages.
"Terpenoid", Wikipedia, downloaded Mar. 22, 2007, 3 pages.
Albrecht et al., Plant Physiol., 1994, vol. 105, pp. 529-534.
Anderson et al., 1989a, J. Biol. Chem. 264:19169-19175.
Anderson et al., 1989b, J. Biol. Chem. 264:19176-19184.
Avalos et al., Biochimica et Biophysica Acta, 966:257-265 (1988).
Badillo et al., 1995, Plant Mol Biol, 27:425-428.
Bansal et al., 1994, Arch Biochem Biophys, 315:393-99.
Basson et al., 1988, Mol Cell Biol, 8:3797-3808.
Bentinger et al., 1998, Arch Biochem Biophys, 353:191-198.
Berges et al., 1997, J. Bacteriol, 179:4664-70.
Bergstrom et al., 1993, Proc. Nat'l Acad Sci USA, 90:80-84.
Bostedor et al., 1997, J Biol. Chem., 272:9197-9203.
Bourot et al., 1995, Gene, 165:97-102.
Carattoli et al., 1991, J. Biol. Chem., 266:5854-5859.
Chambon et al., 1990, Curr. Genetics, 18:41-46.
Chambon et al., 1991, Lipids 26:633-636.
Chen et al., 1994, Prot. Sci. 3:600-607.
Crock et al., "Isolation and bacterial expression of a sequiterpene synthase cDNA clone from peppermint (Mentha x piperita, L.) that produces the aphid alarm pheromone (E)-beta-farnesene", Proc. Natl. Acad. Sci., Nov. 1997, vol. 94, p. 12833-12838.
Crowley et al., 1998, J. Bacteriol., 180:4177-4183.
Dequin et al., 1988, Biotech Lett, 10:457-462.
Dimster-Denk et al., 1994, Mol. Biol. Cell., 5:655-665.
Dimster-Denk et al., 1996, Mol. Cell. Biol., 16:3981-3989.
Donald et al., 1997, Appl. Environ. Microbiol., 63:3341-3344.
Downing et al., 1980, Biochem Biophys Res Comm, 94:974-979.
Eisenreich et al., 1998, Chem Biol, 5:R221-R233.
Faulkner et al., 1999, J. Biol Chem, 274:14831-14837.
Fegueur et al., 1991, Curr Genetics, 20:365-372.
Fujisaki et al., 1990, J. Biochem. 108:995-1000.
Grabowska D. et al. Effect of squalene gene disruption on synthesis of polyprenols in *Saccharomyces cerevisiae*, FEBS Letters, (1998) 434, 406-408.
Hahn et al., 1996, J Bacter. 178:619-624.
Hahn et al., Journal of Bacteriology, Jan 2001, p. 1-11.
Hamano et al. Biosci. Biotechnol. Biochem., 2001, vol. 65, No. 7, pp. 1627-1635.
Hampton et al., 1996, Tr. Biochem Sci, 21:140-145.
Heide et al., Phytochemistry, 26(6):1651-1655 (1987).
Hemmi et al., 1998, J. Biochem. 123:1088-1096.
Hill et al., J. Org. Chem., 48:3607 (1983).
Hiser et al., 1994, J Biol Chem, 269:31383-31389.
Jennings et al., 1991, Proc. Natl. Acad. Sci. USA 88:6038-6042.
Jiang et al., 1995, J Biol Chem, 270:21793-21799.
Kajiwara et al., 1997, Biochem J, 324:421-426.
Karst et al., 1977, Molec. Gen. Genet. 154:269-277.
Kasperek, "Chemistry of Tocopherols and Tocotrienols" Ch. 2, pp. 8-65, L. Maclin, ed., "Vitamin E: A Comprehensive Treatise," Marcel Dekker, NY, 1980.
Keasling "Award #9911463—ME: Metabolic Engineering of Isoprenoid Production", National Science Foundation, Jun. 19, 2000, 2 pages.
Keller et al., 1998, Euro J Biochem, 251:413-417.
Kirk-Othmer "Vitamin E" Encyclopedia of Chemical Technology, vol. 24, pp. 214-225, 3rd Ed. John Wiley and Sons, 1984.
Koyama et al., 1993, J. Biochem. 113:355-363.
Kribii R. et al. Cloning and characterization of the *Arabidopsis thaliana* SQS1 gene encoding squlene synthase. Involvment of the C-terminal region of the enzyme in the channeling of squalene through the sterol pathway, Eur. J. Biochem. (1997) 249, 61-69.
Kuntz et al., 1992, Plant Journal 2:25-34.
Lewis et al., 1985, J Bacter 163:199-207.
Lewis et al., 1988, Yeast 4:93-106.
Lois et al., 1998, Proc Nat'l Acad Sci USA, 95:2105-2110.
Loubbardi et al., 1995, J Bacter., 177:1817-1823.
Mao et al., Curr Microbiol., Jul. 2002; 45(1): pp. 37-40 (Abstract only).
Martin et al., "Engineering a mevalonate pathway in *Escherichia coli* for production of terpenoids", Nature Biotechnology, Jul. 2003, vol. 21, No. 7, pp. 796-802.
Math et al., 1992, Proc. Natl. Acad. Sci. USA 89:6761-6764.
Mayer et al., 1992, Yeast 8:743-748.
Meigs, 1997, Arch Biochem Biophys, 345:1-9.
Misawa N. et al. Metabolic engineering for the production of carotenoids in non-carotenogenic bacteria and yeasts, Journal of Buotechnology, (1998) 59, 169-181.
Miura et al., Production of the Carotenoids Lycopene, β-Carotene, and Astaxanthin in the Food Yeast *Candida utilis*; Applied and Environmental Microbiology 1998, 64(4):1226-1229.
Miura Y. et al. Production of Lycopene by the food yeast *Candida utilis* that does not naturally synthesize cartenoid, Biotech. Bioengineering 1998, 58, 306-308.
Miura Y. et al. Production of the carotenoids lycopene, beta-carotene, and astaxanthin in the food yeast *Candida utilis* , Applied and environmental microbiology, (1998) 64, 1226-1229.
Mosqueda-Cano et al., Current Microbiology, 31:141-145 (1995).
Muzart, Tetrahedron Lett., 32(45):6551-6552 (1991).
Newman et al. "High-Level Procuction of Amorpha-4,11-Diene in a Two-Phase Partitioning Bioreactor of Metabolically Engineered *Escherichia coli*", Wiley InterScience, Jul. 28, 2006, pp. 684-691.
Novotny et al., 1994, Biotech Lett, 16:539-542.
Ohnuma et al., 1996a, J Biol Chem, 271:30748-30754.
Ohnuma et al., 1996b, J. Biochem. 119:541-547.
Oulmouden et al., 1990, Gene 88:253-end.
Oulmouden et al., 1991, Curr. Genet., 19:9-14.
Pitera "Engineering a Heterologous Mevalonate Pathway for the Production of Isoprenoids in *Escherichia coli*", dissertation for the University of California, Berkeley, Spring 2006, 273 pages.
Parks et al., 1995, Annu. Rev. Microbiol. 49:95-116.
Randall et al., Plant Cell, 5:433-442 (1993).
Ro et al., "Loblolly pine abietadienol/abietadienal oxidase PtAO (CYP720B1) is a multifunctional, multisubstrate cytochrome P450 monooxygenase", PNAS, May 31, 2005, vol. 102, No. 22, pp. 8060-8065.
Rontani et al., J. Photochem. Photobiol. A. 79(3):167 (1994) (abstract only).

Rontani et al., J. Photochem. Photobiol. A., 85(1-2):137 (1995) (abstract only).
Rontani et al., Phytochemistry 42(2):347 (1996) (abstract only).
Rontani et al., Tetrahedron Lett., 28(19):2133 (1987) (abstract only).
Sandmann et al., 1993, J. Photochem. Photobiol. B: Biol. 18:245-251.
Sata et al., Tetrahedron Lett., 40(4):719 (1999) (abstract only).
Schmidt, J. Prakt. Chem./Chem Ztg. 339, 493 (1997).
Servouse et al., 1984, Biochem Biophys Res Comm, 123:424-430.
Servouse et al., 1986, Biochem J, 240:541-547.
Sharpless et al., J. Amer. Chem. Soc., 95:6136 (1973).
Shimada H. et al. Increased carotenoid production by the food yeast Candida utilis through metabolic engineering of the isoprenoid pathway, Applied and Environmental Microbiology, (1998), 64, vol. 7, 2676-2680.
Song et al., 1994, Proc. Natl. Acad. Sci. USA, 91:3044-3048.
Street et al., Biochemistry, vol. 29, No. 3, pp. 7531-7538, 1990.
Szkopinska et al., 1993, FEMS Microbiol. Lett, 112:325-328.
Takahashi et al., 1998, Proc Nat'l Acad Sci USA, 95:9879-9884.
Tarshis et al., 1996, Proc. Nat'l Acad Sci USA, 93:15018-15023.
Toth et al., 1996, J Biol Chem, 271:7895-7898.
Tsay et al., 1991, Mol. Cell. Biol., 11:620-631.
Wang et al., 1999, Biotech Bioeng, 62:235-241.
Wiedemann et al., 1993, Arch Biochem Biophys, 306:152-157.
Yamano et al., 1994, Biosci. Biotechnol. Biochem. 58:1112-1114.
Zhu et al., J. Mol. Catalysis A: Chemical 103:87-97 (1995).
Zhu et al., J. Org. Chem., 61:324-328 (1996).
International Search Report for International (PCT) Patent Application No. PCT/US99/15264, mailed Nov. 9, 1999.
International Preliminary Examination Report for International (PCT) Patent Application No. PCT/US99/15264, completed Mar. 6, 2000.
Supplementary Partial European Search Report for European Patent Application No. 99932295.1, dated Mar. 31, 2005.
Supplementary European Search Report for European Patent Application No. 99932295.1, dated Jun. 21, 2005.
Examination Report for European Patent Application No. 99932295.1, dated Sep. 29, 2005.
Examination Report for European Patent Application No. 99932295.1, dated Dec. 21, 2006.
Examination Report for European Patent Application No. 99932295.1, dated Apr. 16, 2007.
Examination Report for European Patent Application No. 99932295.1, dated Aug. 27, 2007.
Lange et al. "A family of transketolases that directs isoprenoid biosynthesis via a mevalonate-independent pathway." Proc Natl Acad Sci U S A. Mar. 3, 1998;95(5):2100-4.
Sprenger et al. "Identification of a thiamin-dependent synthase in Escherichia coli required for the formation of the 1-deoxy-D-xylulose 5-phosphate precursor to isoprenoids, thiamin, and pyridoxol." Proc Natl Acad Sci U S A. Nov. 25, 1997;94(24):12857-62.
Stewart. "A Chemist's Perspective on the Use of Genetically Engineered Microbes as Reagents for Organic Synthesis", Biotechnology and Genetic Engineering Reviews, 14:67-143 (Apr. 1997).
Official Action for Canadian Patent Application No. 2,331,343, mailed Apr. 14, 2009.
Summons to Attend Oral Proceedings for European Patent Application No. 08003596.7, dated Aug. 31, 2009.
U.S. Appl. No. 12/510,041, filed Jul. 27, 2009, Millis et al.
Extended European Search Report for European Patent Application No. 09004155.9, dated Aug. 6, 2009.
Official Action (including English summary) for Japanese Patent Application No. 2000-558056, mailed Jun. 30, 2009.
Official Action for U.S. Appl. No. 11/752,931, mailed September 2, 2009.
Official Action for U.S. Appl, No. 11/753,399, mailed Sep. 17, 2009.
Notice of Allowance for U.S. Appl. No. 11/752,931, mailed Nov. 30, 2009.

* cited by examiner

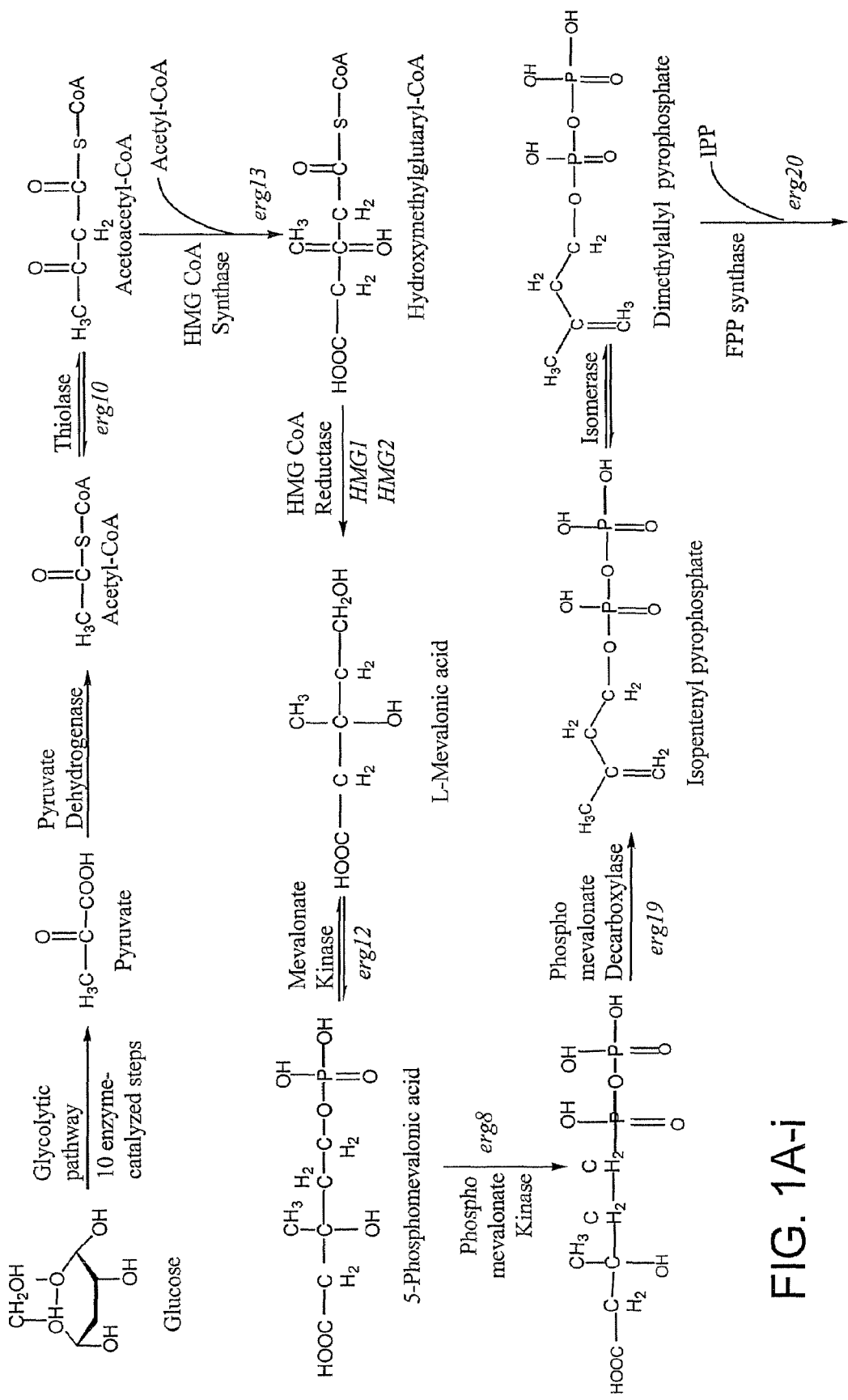
FIG. 1A-i

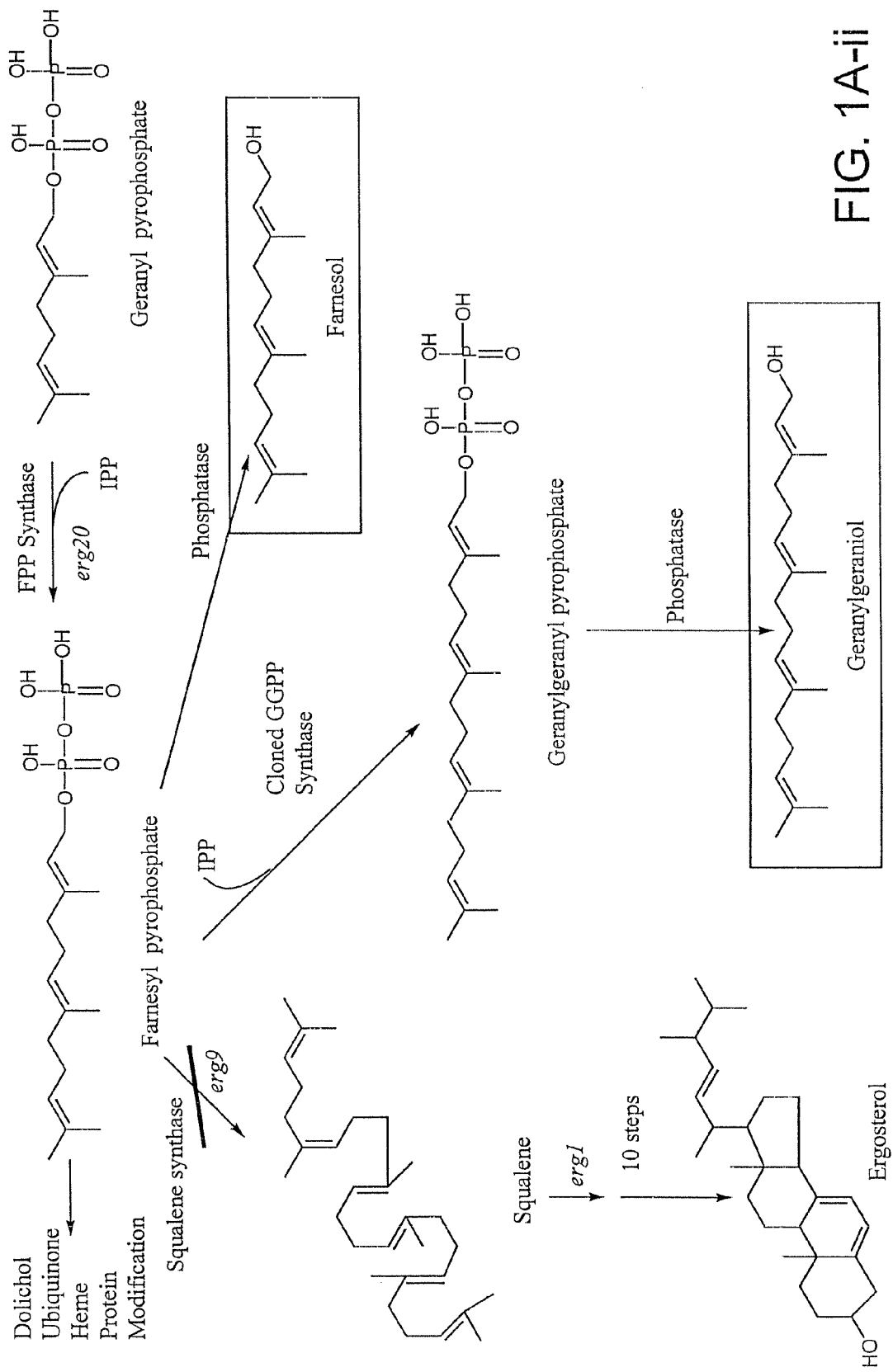
FIG. 1A-ii

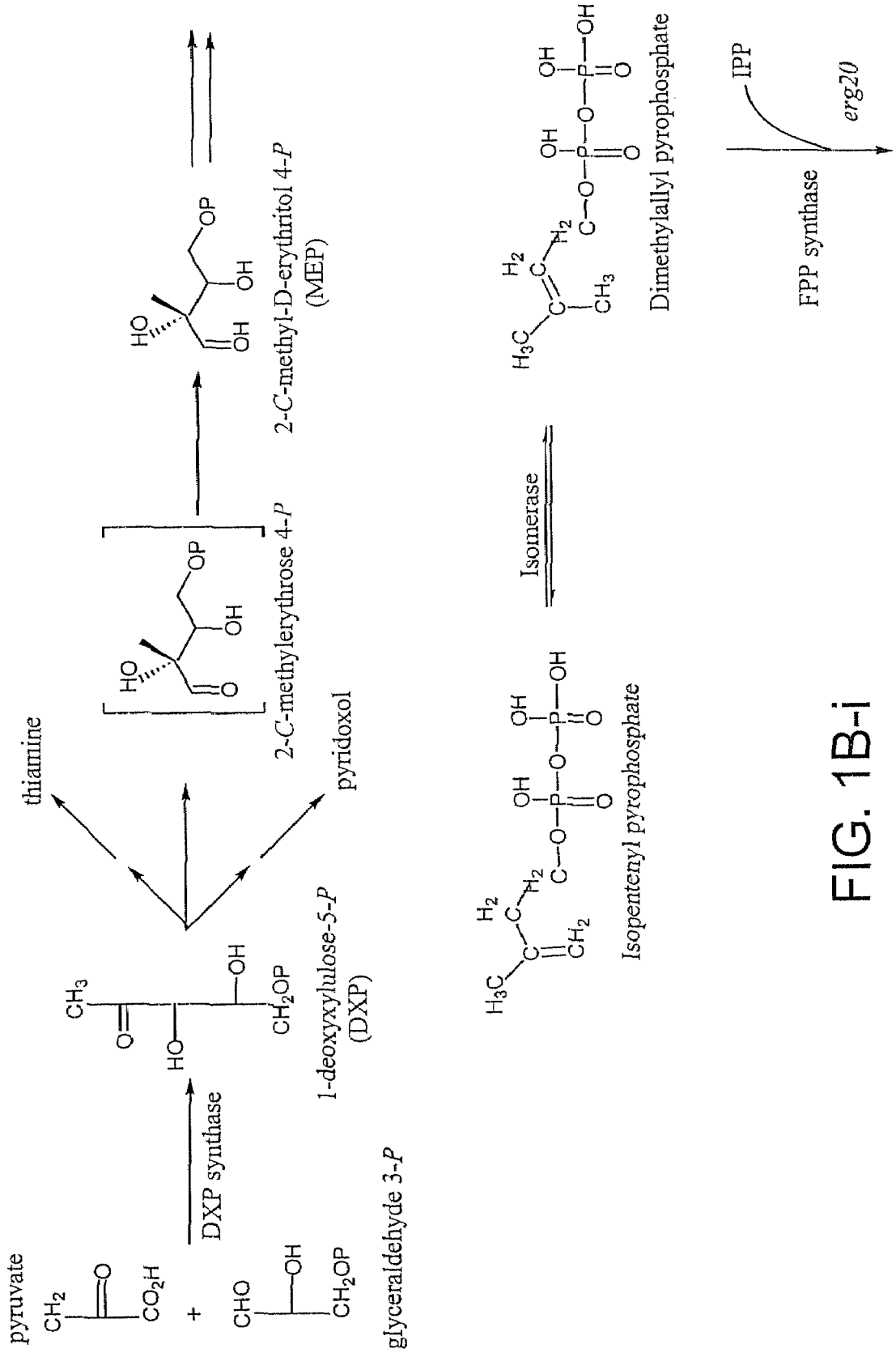
FIG. 1B-i

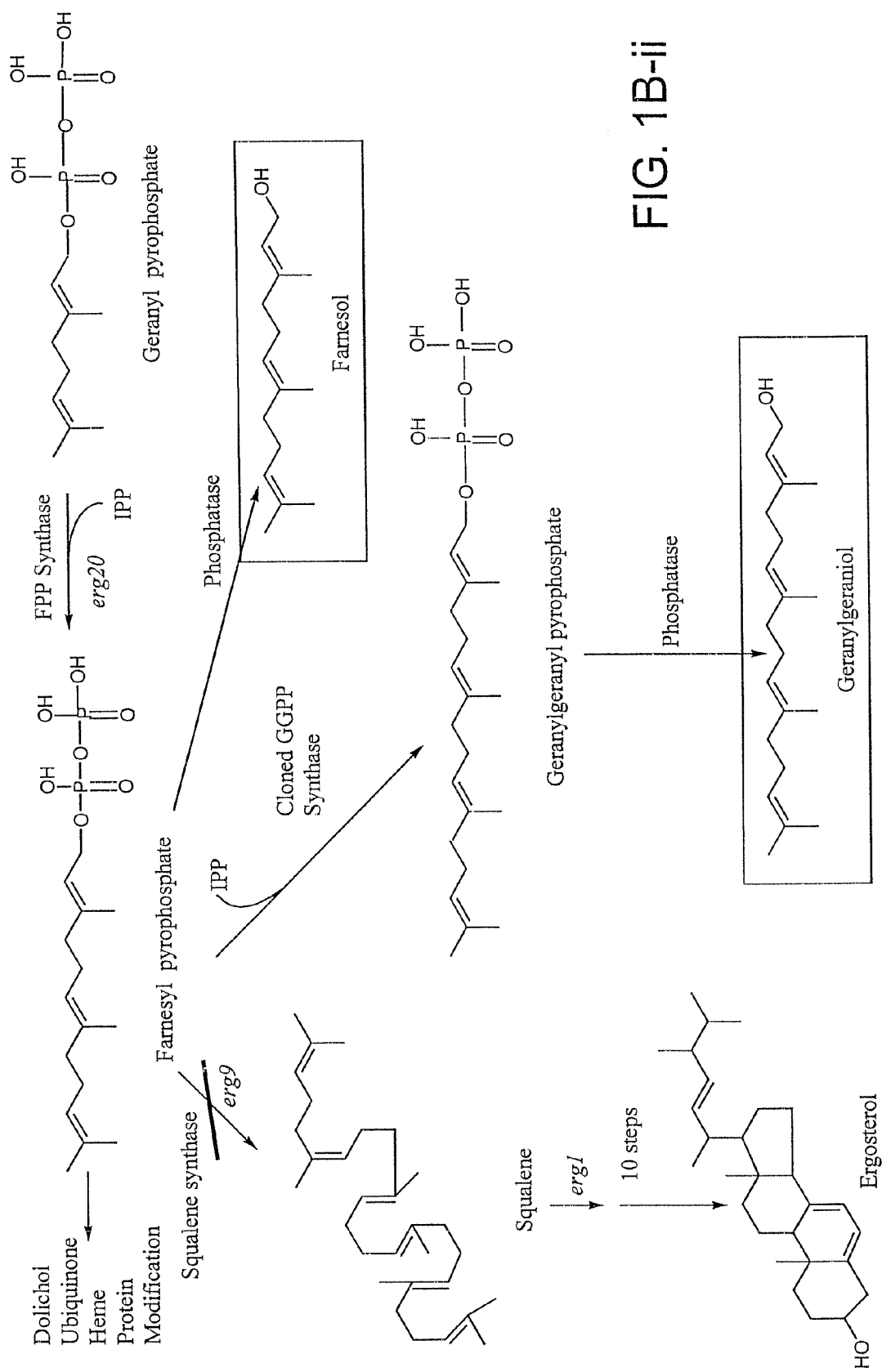
FIG. 1B-ii geranyl pyrophosphate
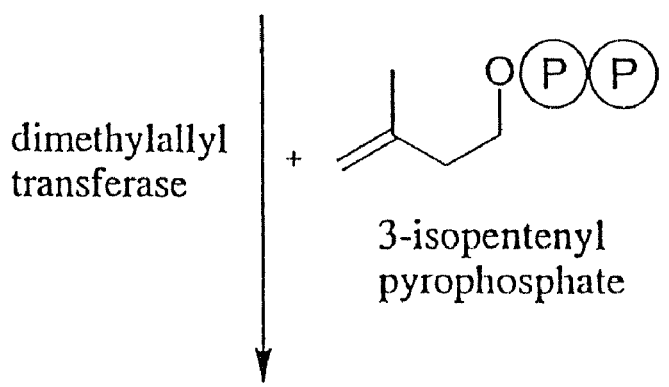
dimethylallyl transferase
3-isopentenyl pyrophosphate
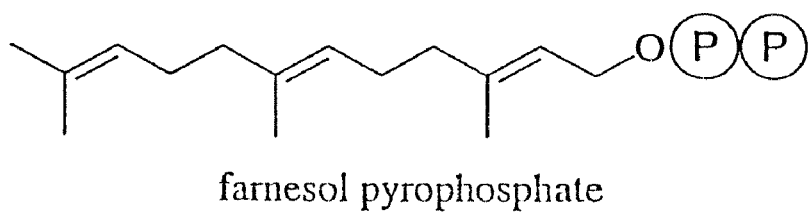
farnesol pyrophosphate
phosphatase
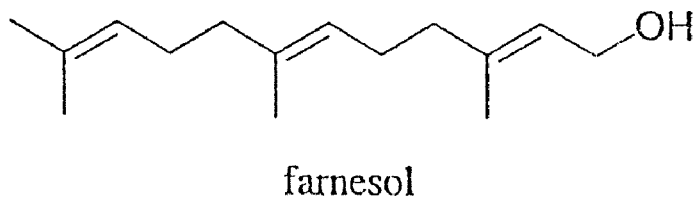
farnesol
FIG. 7-2

US 7,718,417 B2

PRODUCTION OF ISOPRENOIDS

REFERENCE TO RELATED APPLICATION

This application is a continuation of U.S. patent application Ser. No. 10/719,196, filed Nov. 20, 2003, now abandoned, which is a continuation of U.S. patent application Ser. No. 09/909,558, filed Jul. 20, 2001, now U.S. Pat. No. 6,689,593, which is a continuation of U.S. patent application Ser. No. 09/350,275, filed Jul. 6, 1999, now U.S. Pat. No. 6,531,303, which claims priority to U.S. Provisional Patent Application No. 60/091,964, filed Jul. 6, 1998. Each of these priority documents is incorporated herein, in their entirety, by this reference.

FIELD OF THE INVENTION

The present invention relates to the biological production of farnesol and geranylgeraniol.

BACKGROUND OF THE INVENTION

Geranylgeraniol and farnesol are synthesized as, inter alia, precursors of cholesterol and are used as highly lipophilic molecules for fixating proteins to cell membranes. In addition, geranylgeraniol and farnesol exhibit wide range of biological activities such as antimicrobial, antiviral and antitumor activities. These compounds also possess ability to prevent a wide variety of illnesses such as ulcer, neuro-degenerative illnesses, conditions linked to skin aging, the phenomena of thrombosis and atherosclerosis and immune deficiencies. In addition, geranylgeraniol diphosphate is a precursor for the biological synthesis of Taxol®, which is a potent anticancer compound currently marketed by Bristol-Myers Squibb Co. under the generic name paclitaxel.

There remains a need for an efficient and economical method for producing farnesol and/or geranylgeraniol.

BRIEF DESCRIPTION OF THE DRAWINGS

FIG. 1A illustrates a diagramatic representation of the mevalonate-dependent isoprenoid biosynthetic pathway.

FIG. 1B illustrates a diagramatic representation of the mevalonate-independent isoprenoid biosynthetic pathway.

DETAILED DESCRIPTION OF THE INVENTION

1.0 Introduction

Figure 2:
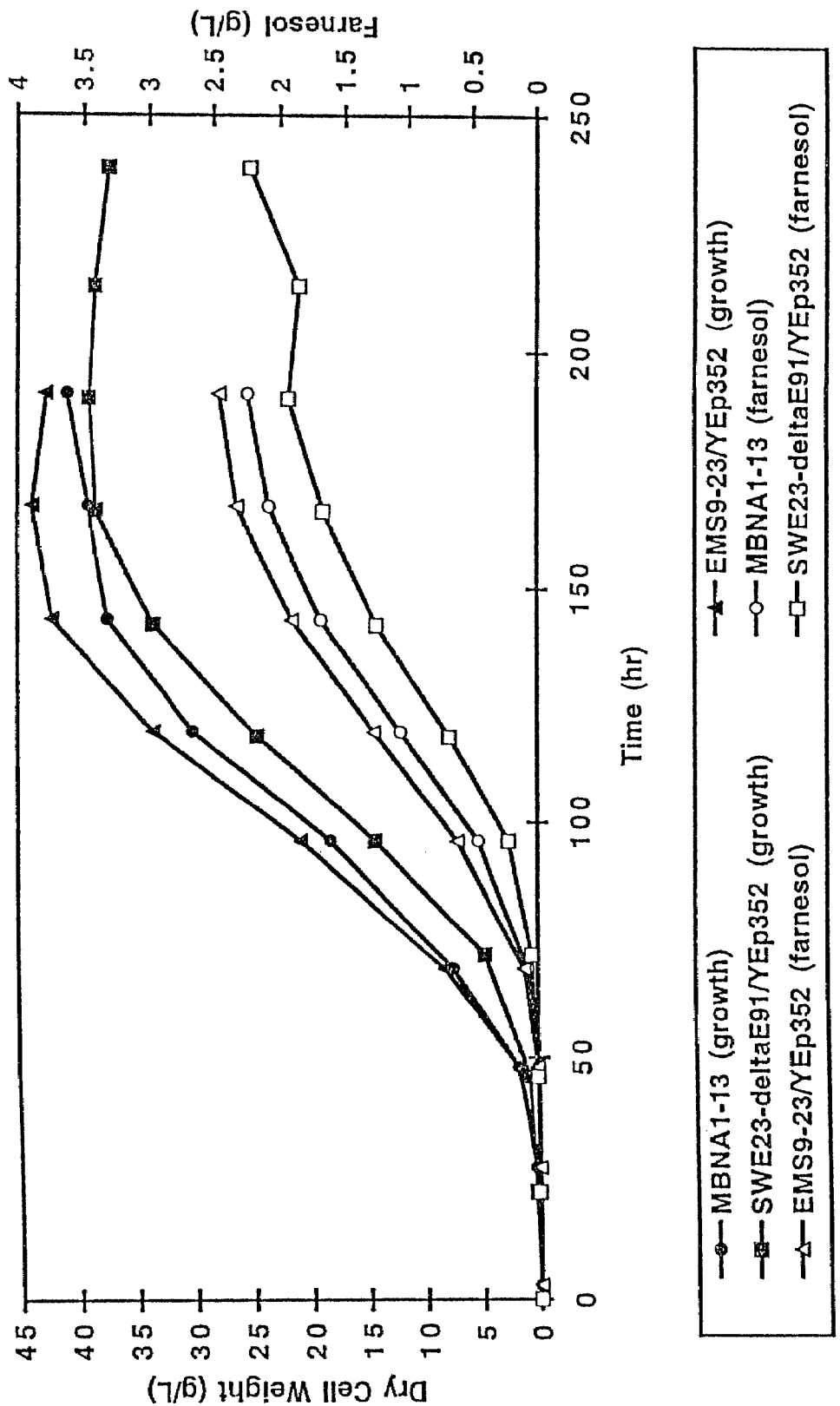
FIG. 2 illustrates the growth and farnesol production of strains derived from strain MBNA1-13.

The present invention provides a method for producing farnesol and geranylgeraniol (GG). The present invention also includes various aspects of biological materials and intermediates useful in the production of farnesol and GG by biological production.

Isoprenoids are the largest family of natural products, with about 22,000 different structures known. All isoprenoids are derived from the $C_5$ compound isopentylpyrophosphate (IPP). Thus, the carbon skeletons of all isoprenoid compounds are created by sequential additions of the $C_5$ units to the growing polyprenoid chain.

While the biosynthetic steps leading from IPP to isoprenoids are universal, two different pathways leading to IPP exist. Fungi (such as yeast) and animals possess the well known mevalonate-dependent pathway (depicted in FIG. 1A) which uses acetyl CoA as the initial precursor. Bacteria and higher plants, on the other hand, possess a newly discovered mevalonate independent pathway, also referred to herein as the non-mevalonate pathway, (depicted in FIG. 1B) leading from pyruvate and glyceraldehyde 3-phosphate [Lois et al., *Proc. Natl. Acad. Sci. USA*, 95, 2105-2110 (1998); Rohmer et al., *J. Am. Chem. Soc.* 118, 2564-2566 (1996); Arigoni, et al., *Proc. Natl. Acad. Sci. USA*, 94, 10600-10605 (1997); Lange et al., *Proc. Natl. Acad. Sci. USA*, 95, 2100-2104 (1998)]. In plants, there is evidence that both the mevalonate-dependent and -independent pathways exist, the former being cytosolic and the latter being plastidial [Arigoni, et al., *Proc. Natl. Acad. Sci. USA*, 94, 10600-10605 (1997); Lange et al., *Proc. Natl. Acad. Sci. USA*, 95, 2100-2104 (1998)]. Several steps of the mevalonate-independent pathway have been established. The first step, catalyzed by D-1-deoxyxylulose 5-phosphate synthase, forms D-1-deoxyxylulose 5-phosphate from pyruvate and glyceraldehyde 3-phosphate. The second and third steps, catalyzed by D-1-deoxyxylulose 5-phosphate reductoisomerase, catalyze the conversion of D-1-deoxyxylulose 5-phosphate to 2-C-methyl D erythritol-4-P (MEP). Several further reactions are required to convert MEP to IPP, and these enzymes are unknown at this time [Lois et al., *Proc. Natl. Acad. Sci. USA*, 95, 2105-2110 (1998); Takahashi et al., *Proc. Natl. Acad. Sci. USA*, 95, 2100-2104 (1998); Duvold et al. *Tetrahedron Letters*, 38, 4769-4772 (1997)].

Farnesol and GG are prenyl alcohols produced by dephosphorylation of farnesylpryrophosphate (FPP) and geranylgeranylpyrophosphate (GGPP), respectively. FPP and GGPP are intermediates in the biosynthesis of isoprenoid compounds, including sterols, ubiquinones, heme, dolichols, and carotenoids, and are used in the post-translational prenylation of proteins. Both FPP and GGPP are derived from IPP. Embodiments of the present invention include the biological production of farnesol or GG in prokaryotic or eukaryotic cell cultures and cell-free systems, irrespective of whether the organism utilizes the mevalonate-dependent or -independent pathway for the biosynthesis of the precursor of all isoprenoids, IPP. Reference herein to farnesyl phosphate or geranylgeranyl phosphate refers to the respective mono-, di- and tri-phosphate compounds, unless one specific form is specifically designated.

2.0 Modified Microorganism

Suitable biological systems for producing farnesol and GG include prokaryotic and eukaryotic cell cultures and cell-free systems. Preferred biological systems include fungal, bacterial and microalgal systems. More preferred biological systems are fungal cell cultures, more preferably a yeast cell culture, and most preferably a *Saccharomyces cerevisiae* cell culture. Fungi are preferred since they have a long history of use in industrial processes and can be manipulated by both classical microbiological and genetic engineering techniques. Yeast, in particular, are well-characterized genetically. Indeed, the entire genome of *S. cerevisiae* has been sequenced, and the genes coding for enzymes in the isoprenoid pathway have already been cloned. Also, *S. cerevisiae* grows to high cell densities, and amounts of squalene and ergosterol (see FIG. 1) up to 16% of cell dry weight have been reported in genetically-engineered strains. For a recent review of the isoprenoid pathway in yeast, see Parks and Casey, *Annu. Rev. Microbiol.* 49:95-116 (1995).

The preferred prokaryote is *E. coli*. *E. coli* is well established as an industrial microorganism used in the production of metabolites (amino acids, vitamins) and several recombinant proteins. The entire *E. coli* genome has also been sequenced, and the genetic systems are highly developed. As mentioned above, *E. coli* uses the mevalonate-independent pathway for synthesis of IPP. The *E. coli* dxs, dxr, idi, and ispA genes, encoding D-1-deoxyxylulose 5-phosphate synthase, D-1-deoxyxylulose 5-phosphate reductoisomerase, IPP isomerase, and FPP synthase, respectively, have been cloned and sequenced [Fujisaki, et. al, *J. Biochem.* 108, 995-1000 (1990); Lois et al., *Proc. Natl. Acad. Sci. USA*, 95, 2105-2110 (1998); Hemmi et al., *J. Biochem.*, 123, 1088-1096 (1998)].

Preferred microalga for use in the present invention include *Chlorella* and *Prototheca*.

Suitable organisms useful in producing farnesol and GG are available from numerous sources, such as the American Type Culture Collection (ATCC), Manassas, Va., Culture Collection of Algae (UTEX), Austin, Tex., the Northern Regional Research Laboratory (NRRL), Peoria, Ill. and the *E. coli* Genetic Stock Center (CGSC), New Haven, Conn. In particular, there are culture collections of *S. cerevisiae* that have been used to study the isoprenoid pathway which are available from, e.g., Jasper Rine at the University of California, Berkeley, Calif. and from Leo Parks at North Carolina State University, Raleigh, N.C.

Preferably the cells used in the cell culture are genetically modified to increase the yield of farnesol or GG. Cells may be genetically modified by genetic engineering techniques (i.e., recombinant technology), classical microbiological techniques, or a combination of such techniques and can also include naturally occurring genetic variants. Some of such techniques are generally disclosed, for example, in Sambrook et al., 1989, *Molecular Cloning: A Laboratory Manual*, Cold Spring Harbor Labs Press. The reference Sambrook et al., ibid., is incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect of increased yields of farnesol or GG within the microorganism or in the culture supernatant. As used herein, genetic modifications which result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity). Genetic modifications which result in an increase in gene expression or function can be referred to as amplification, overproduction, overexpression, activation, enhancement, addition, or up-regulation of a gene. Addition of cloned genes to increase gene expression can include maintaining the cloned gene(s) on replicating plasmids or integrating the cloned gene(s) into the genome of the production organism. Furthermore, increasing the expression of desired cloned genes can include operatively linking the cloned gene(s) to native or heterologous transcriptional control elements.

2.1 Squalene Synthase Modifications

Embodiments of the present invention include biological production of farnesol or GG by culturing a microorganism, preferably yeast, which has been genetically modified to modulate the activity of one or more of the enzymes in its isoprenoid biosynthetic pathway. In one embodiment, a microorganism has been genetically modified by decreasing (including eliminating) the action of squalene synthase activity (see FIG. 1). For instance, yeast erg9 mutants that are unable to convert mevalonate into squalene, and which accumulate farnesol, have been produced. Karst and Lacroute, *Molec. Gen. Genet.*, 154, 269-277 (1977); U.S. Pat. No. 5,589,372. As used herein, reference to erg9 mutant or mutation generally refers to a genetic modification that decreases the action of squalene synthase, such as by blocking or reducing the production of squalene synthase, reducing squalene synthase activity, or inhibiting the activity of squalene synthase, which results in the accumulation of farnesyl diphosphate (FPP) unless the FPP is otherwise converted to another compound, such as farnesol by phosphatase activity. Blocking or reducing the production of squalene synthase can include placing the ERG9 gene under the control of a promoter that requires the presence of an inducing compound in the growth medium. By establishing conditions such that the inducer becomes depleted from the medium, the expression of ERG9 (and therefore, squalene synthase synthesis) could be turned off. Also, some promoters are turned off by the presence of a repressing compound. For example, the promoters from the yeast CTR3 or CTR1 genes can be repressed by addition of copper. Blocking or reducing the activity of squalene synthase could also include using an excision technology approach similar to that described in U.S. Pat. No. 4,743,546, incorporated herein by reference. In this approach, the ERG9 gene is cloned between specific genetic sequences that allow specific, controlled excision of the ERG9 gene from the genome. Excision could be prompted by, for example, a shift in the cultivation temperature of the culture, as in U.S. Pat. No. 4,743,546, or by some other physical or nutritional signal. Such a genetic modification includes any type of modification and specifically includes modifications made by recombinant technology and by classical mutagenesis. Inhibitors of squalene synthase are known (see U.S. Pat. No. 4,871,721 and the references cited in U.S. Pat. No. 5,475,029) and can be added to cell cultures. In another embodiment, an organism having the mevalonate-independent pathway of isoprenoid biosynthesis (such as *E. coli*) is genetically modified so that it accumulates FPP and/or farnesol. For example, decreasing the activity of octaprenyl pyrophosphate synthase (the product of the ispB gene) would be expected to result in FPP accumulation in *E. coli*. (Asai, et al., Biochem. Biophys. Res. Comm. 202, 340-345 (1994)). The action of a phosphatase could further result in farnesol accumulation in *E. coli*.

Yeast strains need ergosterol for cell membrane fluidity, so mutants blocked in the ergosterol pathway, such as erg9 mutants, need extraneous ergosterol or other sterols added to the medium for the cells to remain viable. The cells normally cannot utilize this additional sterol unless grown under anaerobic conditions. Therefore, a further embodiment of the present invention is the use of a yeast in which the action of squalene synthase is reduced, such as an erg9 mutant, and which takes up exogenously supplied sterols under aerobic conditions. Genetic modifications which allow yeast to utilize sterols under aerobic conditions are demonstrated below in the Examples section (see Example 1) and are also known in the art. For example, such genetic modifications include upc (uptake control mutation which allows cells to take up sterols under aerobic conditions) and hem1 (the HEM1 gene encodes aminolevulinic acid synthase which is the first committed step to the heme biosynthetic pathway from FPP, and hem1 mutants are capable of taking up ergosterol under aerobic conditions following a disruption in the ergosterol biosynthetic pathway, provided the cultures are supplemented with unsaturated fatty acids). Yeast strains having these mutations can be produced using known techniques and also are available from, e.g., Dr. Leo Parks, North Carolina State University, Raleigh, N.C. Haploid cells containing these mutations can be used to generate other mutants by genetic crosses with other haploid cells. Also, overexpression of the SUT1 (sterol uptake) gene can be used to allow for uptake of sterols under aerobic conditions. The SUT1 gene has been cloned and sequenced. Bourot and Karst, *Gene,* 165: 97-102 (1995).

In a further embodiment, microorganisms of the present invention can be used to produce farnesol and/or GG by culturing microorganisms in the presence of a squalene synthase inhibitor. In this manner, the action of squalene synthase is reduced. Squalene synthase inhibitors are known to those skilled in the art. (See, for example, U.S. Pat. No. 5,556,990.

2.2 HMG-CoA Reductase Modifications

A further embodiment of the present invention is the use of a microorganism which has been genetically modified to increase the action of HMG-CoA reductase. It should be noted that reference to increasing the action of HMG-CoA reductase and other enzymes discussed herein refers to any genetic modification in the microorganism in question which results in increased functionality of the enzymes and includes higher activity of the enzymes, reduced inhibition or degradation of the enzymes and overexpression of the enzymes. For example, gene copy number can be increased, expression levels can be increased by use of a promoter that gives higher levels of expression than that of the native promoter, or a gene can be altered by genetic engineering or classical mutagenesis to increase the activity of an enzyme. One of the key enzymes in the mevalonate-dependent isoprenoid biosynthetic pathway is HMG-CoA reductase which catalyzes the reduction of 3-hydroxy-3-methylglutaryl-coenzyme A (HMG-CoA). This is the primary rate-limiting and first irreversible step in the pathway, and increasing HMG-CoA reductase activity leads to higher yields of squalene and ergosterol in a wild-type strain of *S. cerevisiae*, and farnesol in an erg9 strain. One mechanism by which the action of HMG-CoA reductase can be increased is by reducing inhibition of the enzyme, by either genetically modifying the enzyme or by modifying the system to remove the inhibitor. For instance, both sterol and non-sterol products of the isoprenoid pathway feedback inhibit this enzyme (see, e.g., Parks and Casey, *Annu. Rev. Microbiol.* 49:95-116 (1995). Alternatively or in addition, the gene(s) coding for HMG-CoA reductase can be altered by genetic engineering or classical mutagenesis techniques to decrease or prevent inhibition. Also, the action of HMG-CoA reductase can be increased by increasing the gene copy number, by increasing the level of expression of the HMG-CoA reductase gene(s), or by altering the HMG-CoA reductase gene(s) by genetic engineering or classical mutagenesis to increase the activity of the enzyme. See U.S. Pat. No. 5,460,949, the entire contents of which are incorporated herein by reference. For example, truncated HMG-CoA reductases have been produced in which the regulatory domain has been removed and the use of gene copy numbers up to about six also gives increased activity. Id. See also, Downing et al., *Biochem. Biophys. Res. Commun.,* 94, 974-79 (1980) describing two yeast mutants having increased levels of HMG-CoA reductase. Two isozymes of HMGCoA reductase, encoded by the HMG1 and HMG2 genes, exist in *S. cerevisiae*. The activity of these two isozymes is regulated by several mechanisms including regulation of transcription, regulation of translation, and for Hmg2p, degradation of the enzyme in the endoplasmic reticulum (Hampton and Rine, 1994; Donald, et. al. 1997). In both Hmg1p and Hmg2p, the catalytic domain resides in the COOH terminal portion of the enzyme, while the regulatory domain resides in the membrane spanning $NH_2$-terminal region. It has been shown that overexpression of just the catalytic domain of Hmg1p in *S. cerevisiae* increases carbon flow through the isoprenoid pathway, resulting in overproduction of squalene (Saunders, et. al. 1995; Donald, et. al., 1997). The present inventors have expressed the catalytic domain of the *S. cerevisiae* Hmg2p in strains having a normal (i.e., unblocked) isoprenoid pathway and observed a significant increase in the production of squalene. Furthermore, overexpression of the catalytic domain of Hmg2p resulted in increased farnesol production in an erg9 mutant, and increased farnesol and GG production in an erg9 mutant overexpressing GGPP synthase, grown in fermentors.

2.3 GGPP Synthase Modifications

A further embodiment of the present invention is the use of a microorganism which has been genetically modified to increase the action of GGPP synthase. Genes coding for this enzyme from a variety of sources, including bacteria, fungi, plants, mammals, and archaebacteria, have been identified. See, Brinkhaus et al., *Arch. Biochem. Biophys.,* 266, 607-612 (1988); Carattoli et al., *J. Biol. Chem.,* 266, 5854-59 (1991); Chen et al., *J. Biol. Chem.,* 268, 11002-11007 (1993); Dogbo et al., *Biochim. Biophys. Acta,* 920, 140-148 (1987); Jiang et al., *J. Biol. Chem.,* 270, 21793-99 (1995); Kuntz al., *Plant J.,* 2, 25-34 (1992); Laferriere, et al., *Biochim. Biophys. Acta,* 1077, 167-72 (1991); Math et al., *Proc. Natl. Acad. Sci. USA,* 89, 6761-64 (1992); Ohnuma et al., *J. Biol. Chem.,* 269, 14792-97 (1994); Sagami et al., *Arch. Biochem. Biophys.,* 297, 314-20 (1992); Sagami et al., *J. Biol. Chem.,* 269, 20561-66 (1994); Sandmann et al., *J. Photochem. Photobiol. B: Biol.,* 18, 245-51 (1993); Scolnik et al., *Plant Physiol.,* 104, 1469-70 (1994); Tachibana et al., *Biosci. Biotech. Biochem.,* 7, 1129-33 (1993); Tachibana et al., *J. Biochem.,* 114, 389-92 (1993); Wiedemann et al., *Arch. Biochem. Biophys.,* 306, 152-57 (1993). Some organisms have a bifunctional enzyme which also serves as an FPP synthase, so it is involved in the overall conversion of IPP and DMAPP to FPP to GGPP (see FIG. 1). Some enzymes, such as those found in plants, have relaxed specificity, converting IPP and DMAPP to GGPP (see FIG. 1). Genetic modifications of GGPP synthase, as used herein, encompass engineering a monofunctional GGPP synthase or a bifunctional FPP/GGPP synthase to enhance the GGPP synthase activity component of the enzyme. A preferred GGPP synthase gene is the BTS1 gene from *S. cervisiae*. The BTS1 gene and its isolation are described in Jiang et al., *J. Biol. Chem.,* 270, 21793-99 (1995) and copending application Ser. No. 08/761,344, filed on Dec. 6, 1996, the complete disclosure of which incorporated herein by reference. However, GGPP synthases of other hosts can be used, and the use of the bifunctional GGPP synthases may be particularly advantageous in terms of channeling carbon flow through FPP to GGPP, thereby avoiding loss of FPP to competing reactions in the cell.

In further embodiments of the invention, in addition to the modifications of GGPP synthase described above, the wild type GGPP synthase is eliminated from the production organism. This would serve, for example, to eliminate competition between the modified GGPP synthase and the wild type enzyme for the substrates, FPP and IPP. Deletion of the wild-type gene encoding GGPP synthase could also improve the stability of the cloned GGPP synthase gene by removing regions of high genetic sequence homology, thereby avoiding potentially detrimental genetic recombination.

2.4 FPP Synthase Modifications

A further embodiment of the present invention is the use of a microorganism which has been genetically modified to increase the action of FPP synthase.

Genes coding for this enzyme from a variety of sources have been identified. See, Anderson et al., *J. Biol. Chem.*, 264, 19176-19184 (1989); Attucci, et al., *Arch. Biochem. Biophys.*, 321, 493-500 (1995); Cane et al., *J. Am. Chem. Soc.*, 105, 122-124 (1983); Chambon et al., *Current Genetics*, 18, 41-46 (1990); Chambon et al., *Lipids*, 26, 633-36 (1991); Chen al., *Protein Science*, 3, 600-607 (1994); Davisson, et al., *J. Am. Chem. Soc.*, 115, 1235-45 (1993); Ding et al., *Biochem. J*, 275, 61-65 (1991); Hugueney et al., *FEBS Letters*, 273, 235-38 (1990); Joly et al., *J. Biol. Chem.*, 268, 26983-89 (1993); Koyama al., *J. Biochem.*, 113, 355-63 (1993); Sheares, et al., *Biochem.*, 28, 8129-35 (1989); Song et al., *Proc. Natl. Acad. Sci. USA*, 91, 3044-48 (1994); Spear et al., *J. Biol. Chem.*, 267, 14662-69 (1992); Spear et al., *J. Biol. Chem.*, 269, 25212-18 (1994). Anderson et al., *J. Biol. Chem.*, 264, 19176-19184 (1989) reported a 2-3 fold overexpression of FPP synthase with the *S. cerevisiae* gene in a yeast shuttle vector.

As described in the Examples section, it has been surprisingly found that overexpression of FPP synthase did not lead to an increase in farnesol production, but unexpectedly lead to an increase in the production of GG in the absence of any overexpression of GGPP synthase.

In further embodiments of the invention, in addition to the modifications of FPP synthase described above, the wild type FPP synthase is eliminated from the production organism. This would serve, for example, to eliminate competition between the modified FPP synthase and the wild type enzyme for the substrates, IPP, DMAPP and GPP. Deletion of the wild-type gene encoding FPP synthase could also improve the stability of the cloned FPP synthase gene by removing regions of high genetic sequence homology, thereby avoiding potentially detrimental genetic recombination.

2.5 Phosphatase Modifications

A further embodiment of the present invention is the use of a microorganism which has been genetically modified to increase phosphatase action to increase conversion of FPP to farnesol or GGPP to GG. For example, both *S. cerevisiae* and *E. coli* contain numerous phosphatase activities. By testing several phosphatases for efficient dephosphorylation of FPP or GGPP, one could select an appropriate phosphatase and express the gene encoding this enzyme in a production organism to enhance farnesol or GG production. In addition to (or instead of) increasing the action of a desired phosphatase to enhance farnesol or GG production, one could eliminate, through genetic means, undesirable phosphatase activities. For example, one could eliminate through mutation the activity of a phosphatase that specifically acts on FPP, so that the FPP that was spared would be available for conversion to GGPP and subsequently GG.

2.6 Additional Genetic Modifications.

Modifications of Other Isoprenoid Pathway Enzymes. Modifications that can be made to increase the action of HMGCoA reductase, GGPP synthase and phosphatases are described above. Modification of the action of isoprenoid pathway enzymes is not limited to those specific examples, and similar strategies can be applied to modify the action of other isoprenoid pathway enzymes such as acetoacetyl Co-A thiolase, HMG-CoA synthase, mevalonate kinase, phosphomevalonate kinase, phosphomevalonate decarboxylase, IPP isomerase, farnesyl pyrophosphate synthase or D-1-deoxyxylulose 5-phosphate synthase D-1-deoxyxylulose 5-phosphate reductoisomerase.

Engineering of Central Metabolism to Increase Precursor Supply to the Isoprenoid Pathway. In organisms having the mevalonate-dependent isoprenoid pathway, the biosynthesis of farnesol or GG begins with acetyl CoA (refer to FIG. 1). One embodiment of the present invention is genetic modification of the production organism such that the intracellular level of acetyl CoA is increased, thereby making more acetyl CoA available for direction to the isoprenoid pathway (and hence to farnesol and/or GG). For example, the supply to acetyl CoA can be increased by increasing the action of the pyruvate dehydrogenase complex. The supply of acetyl CoA can be further increased by increasing the level of pyruvate in the cell by increasing the action of pyruvate kinase. In organisms having the mevalonate-independent isoprenoid pathway, the biosynthesis of isoprenoids begins with pyruvate and glyceraldehyde 3-phosphate. The supply of pyruvate and glyceraldehyde 3-phosphate available for isoprenoid biosynthesis can be increased by increasing the action of pyruvate kinase and triophosphate isomerase, respectively.

The examples above are provided only to illustrate the concept of engineering central metabolism for the purpose of increasing production of isoprenoid compounds, and are not an exhaustive list of approaches that can be taken. Numerous other strategies could be successfully applied to achieve this goal.

Blocking Pathways that Compete for FPP or GGPP. In yeast, FPP is a branch point intermediate leading to the biosynthesis of sterols, heme, dolichol, ubiquinone, GGPP and farnesylated proteins. In *E. coli*, FPP serves as the substrate for octaprenyl pyrophosphate synthase in the pathway leading to ubiquinone. In bacteria that synthesize carotenoids, such as *Erwina uredovora*, FPP is converted to GGPP by GGPP synthase in the first step leading to the carotenoids. To increase the production of farnesol or GG, it is desirable to inactivate genes encoding enzymes that use FPP or GGPP as substrate, or to reduce the activity of the enzymes themselves, either through mutation or the use of specific enzyme inhibitors (as was discussed above for squalene synthase). In *S. cerevisiae*, for example, it may be advantageous to inactivate the first step in the pathway from FPP to heme, in addition to inactivating ERG9. As discussed earlier, in *E. coli*, partial or complete inactivation of the octaprenyl pyrophosphate synthase could increase the availability of FPP for conversion of farnesol. Finally, in bacteria that produce carotenoids, such as *Erwina uredovora*, elimination of GGPP synthase can increase the level of FPP for conversion of farnesol, while inactivating or reducing the activity of phytoene synthase (the crtB gene product) can increase the level of GGPP available for conversion to GG.

It is possible that blocking pathways leading away from FPP or GGPP could have negative effects on the growth and physiology of the production organism. It is further contemplated that additional genetic modifications required to offset these complications can be made. The isolation of mutants of *S. cerevisiae* that are blocked in the isoprenoid pathway and take up sterols under aerobic conditions, as described above, illustrates that compensating mutations can be obtained that overcome the effects of the primary genetic modifications.

Isolation of Production Strains that are Resistant to Farnesol or GG. In the Examples section, production of high levels of farnesol and GG by genetically modified strains of *S. cerevisiae* is described. It is recognized that as further increases in farnesol or GG production are made, these compounds may reach levels that are toxic to the production organism. Indeed, product toxicity is a common problem encountered in biological production processes. However, just as common are the genetic modifications made by classical methods or recombinant technology that overcome product toxicity. The present invention anticipates encountering product toxicity. Thus a further embodiment of this invention is the isolation of mutants with increased resistance to farnesol and/or GG.

Isolation of Production Organisms with Improved Growth Properties. One effect of blocking the isoprenoid pathway in *S. cerevisiae* is that the mutant organisms (in the present invention, erg9 mutants) grow more slowly than their parent (unblocked) strains, despite the addition of ergosterol to the culture medium. That the slower growth of the erg9 mutants is due to the block at erg9 is illustrated in Example 1.G, which shows that repairing the erg9 mutation restores the growth rate of the strain to about that of the wild-type parent. The slower growth of the erg9 mutants could be due to differences related to growing on exogenously supplied ergosterol vs. ergosterol synthesized in the cell, or could be due to other physiological factors. One embodiment of the present invention is to isolate variants of the farnesol or GG producing strains with improved growth properties. This could be achieved, for example by continuous culture, selecting for faster growing variants. Such variants could occur spontaneously or could be obtained by classical mutagenesis or molecular genetic approaches.

3.0 Incorporation of Prenol and Isoprenol

Figures 1, 7:
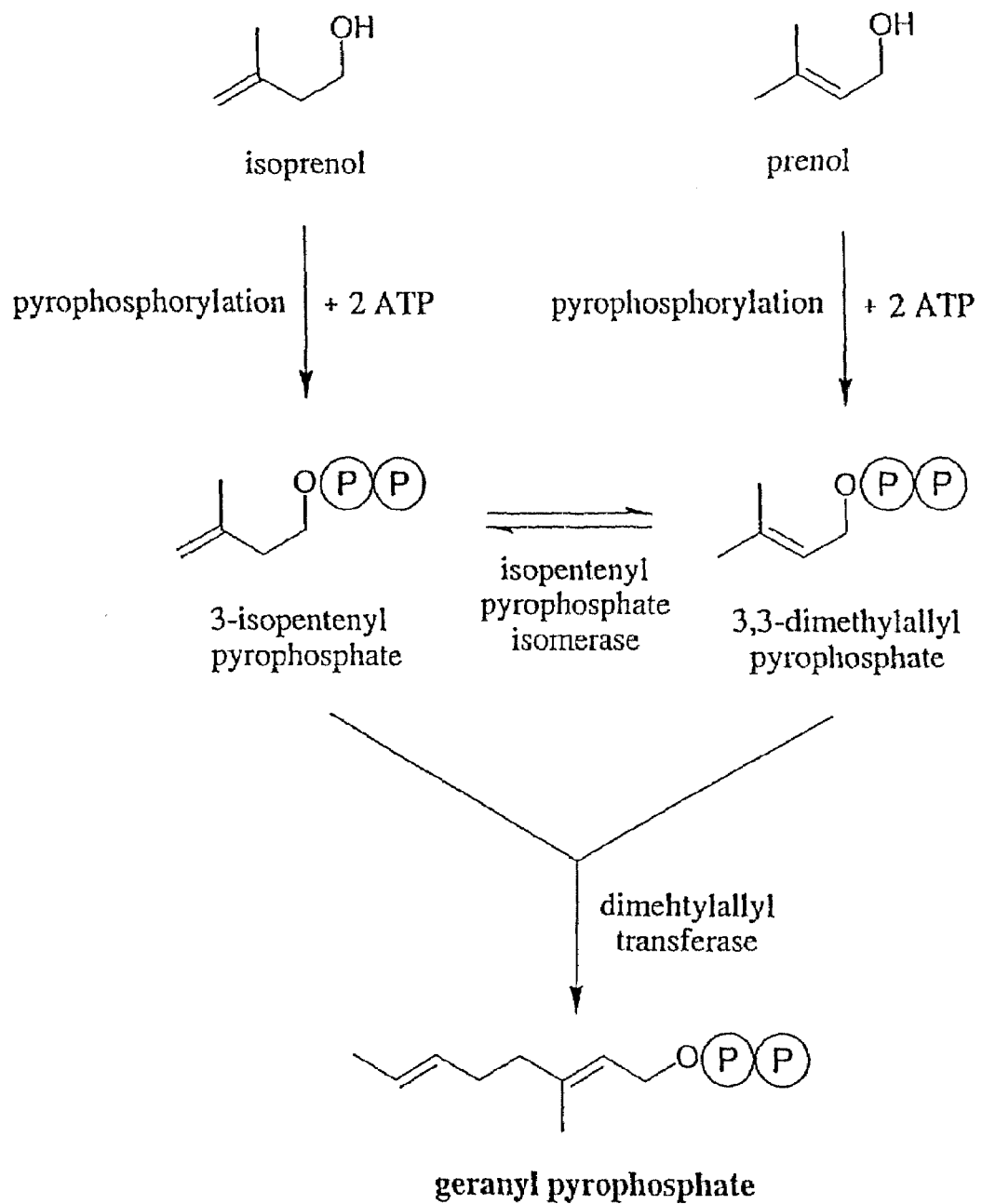
FIG. 7 illustrates the pathway for metabolic conversion of isoprenol and prenol to farnesol.

In a further embodiment of the present invention, farnesol or GG is produced by the introduction of isoprenol and/or prenol into a fermentation medium. With reference to FIG. 7, each of these compounds, when taken up by an organism is phosphorylated with a pyrophosphate group to form, respectively, 3-isopentenyl pyrophosphate and 3,3-dimethylallyl pyrophosphate. These two compounds interconvert by the action of isopentenyl pyrophosphate isomerase. These compounds are then converted to farnesyl pyrophosphate by the action of FPP synthase. Farnesol is formed by dephosphorylation of farnesyl pyrophosphate. Farnesyl pyrophosphate can be further converted to geranylgeranyl pyrophosphate. Geranylgeraniol is formed be dephosyphorylation of geranylgeranyl pyrophosphate. GG would be formed from FPP by the combined action of GGPP synthase and a phosphatase. Isoprenol and prenol are commercially available compounds and can be produced by methods known in the art In this embodiment, the microorganism used in the fermentation can be any microorganism as described elsewhere herein. In addition, the microorganism can be genetically modified to increase the action of dimethylallyl transferase to promote the production of geranyl pyrophosphate and farnesol pyrophosphate. Genes coding for this enzyme from a variety of sources have been identified [Chen et al., *Protein Sci.*, 3, 600-607 (1994)]. In addition a microorganism can be genetically modified to increase the action of isoprenol kinase or prenol kinase. Although these enzymes have not been discovered, similar enzymes that phosphorylate farnesol and geranylgeraniol have been described [Bentinger et al., *Arch.* *Biochem. Biophys.*, 353, 191-198 (1998); Ohnuma et al., *J. Biochem.*, 119, 541-547 (1996)].

4.0 Fermentation Media and Conditions

In the method for production of farnesol or GG, a microorganism having a genetically modification, as discussed above is cultured in a fermentation medium for production of farnesol or GG. An appropriate, or effective, fermentation medium refers to any medium in which a genetically modified microorganism of the present invention, when cultured, is capable of producing farnesol or GG. Such a medium is typically an aqueous medium comprising assimilable carbon, nitrogen and phosphate sources. Such a medium can also include appropriate salts, minerals, metals and other nutrients. In addition, when an organism which is blocked in the ergosterol pathway and requires exogenous sterols, the fermentation medium must contain such exogenous sterols. Appropriate exemplary media are shown in the discussion below and in the Examples section. It should be recognized, however, that a variety of fermentation conditions are suitable and can be selected by those skilled in the art.

Sources of assimilable carbon which can be used in a suitable fermentation medium include, but are not limited to, sugars and their polymers, including, dextrin, sucrose, maltose, lactose, glucose, fructose, mannose, sorbose, arabinose and xylose; fatty acids; organic acids such as acetate; primary alcohols such as ethanol and n-propanol; and polyalcohols such as glycerine. Preferred carbon sources in the present invention include monosaccharides, disaccharides, and trisaccharides. The most preferred carbon source is glucose.

The concentration of a carbon source, such as glucose, in the fermentation medium should promote cell growth, but not be so high as to repress growth of the microorganism used. Typically, fermentations are run with a carbon source, such as glucose, being added at levels to achieve the desired level of growth and biomass, but at undetectable levels (with detection limits being about <0.1 g/l). In other embodiments, the concentration of a carbon source, such as glucose, in the fermentation medium is greater than about 1 g/L, preferably greater than about 2 g/L, and more preferably greater than about 5 g/L. In addition, the concentration of a carbon source, such as glucose, in the fermentation medium is typically less than about 100 g/L, preferably less than about 50 g/L, and more preferably less than about 20 g/L. It should be noted that references to fermentation component concentrations can refer to both initial and/or ongoing component concentrations. In some cases, it may be desirable to allow the fermentation medium to become depleted of a carbon source during fermentation.

Sources of assimilable nitrogen which can be used in a suitable fermentation medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the fermentation medium is greater than about 0.1 g/L, preferably greater than about 0.25 g/L, and more preferably greater than about 1.0 g/L. Beyond certain concentrations, however, the addition of a nitrogen source to the fermentation medium is not advantageous for the growth of the microorganisms. As a result, the concentration of the nitrogen sources, in the fermentation medium is less than about 20 g/L, preferably less than about 10 g/L and more preferably less than about 5 g/L. Further, in some instances it may be desirable to allow the fermentation medium to become depleted of the nitrogen sources during fermentation.

The effective fermentation medium can contain other compounds such as inorganic salts, vitamins, trace metals or growth promoters. Such other compounds can also be present in carbon, nitrogen or mineral sources in the effective medium or can be added specifically to the medium.

The fermentation medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the fermentation medium is greater than about 1.0 g/L, preferably greater than about 2.0 g/L and more preferably greater than about 5.0 g/L. Beyond certain concentrations, however, the addition of phosphate to the fermentation medium is not advantageous for the growth of the microorganisms. Accordingly, the concentration of phosphate in the fermentation medium is typically less than about 20 g/L, preferably less than about 15 g/L and more preferably less than about 10 g/L.

A suitable fermentation medium can also include a source of magnesium, preferably in the form of a physiologically acceptable salt, such as magnesium sulfate heptahydrate, although other magnesium sources in concentrations which contribute similar amounts of magnesium can be used. Typically, the concentration of magnesium in the fermentation medium is greater than about 0.5 g/L, preferably greater than about 1.0 g/L, and more preferably greater than about 2.0 g/L. Beyond certain concentrations, however, the addition of magnesium to the fermentation medium is not advantageous for the growth of the microorganisms. Accordingly, the concentration of magnesium in the fermentation medium is typically less than about 10 g/L, preferably less than about 5 g/L, and more preferably less than about 3 g/L. Further, in some instances it may be desirable to allow the fermentation medium to become depleted of a magnesium source during fermentation.

The fermentation medium can also include a biologically acceptable chelating agent, such as the dihydrate of trisodium citrate. In such instance, the concentration of a chelating agent in the fermentation medium is greater than about 0.2 g/L, preferably greater than about 0.5 g/L, and more preferably greater than about 1 g/L. Beyond certain concentrations, however, the addition of a chelating agent to the fermentation medium is not advantageous for the growth of the microorganisms. Accordingly, the concentration of a chelating agent in the fermentation medium is typically less than about 10 g/L, preferably less than about 5 g/L, and more preferably less than about 2 g/L.

The fermentation medium can also initially include a biologically acceptable acid or base to maintain the desired pH of the fermentation medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In a preferred embodiment of the present invention, the base used is ammonium hydroxide.

The fermentation medium can also include a biologically acceptable calcium source, including, but not limited to, calcium chloride. Typically, the concentration of the calcium source, such as calcium chloride, dihydrate, in the fermentation medium is within the range of from about 5 mg/L to about 2000 mg/L, preferably within the range of from about 20 mg/L to about 1000 mg/L, and more preferably in the range of from about 50 mg/L to about 500 mg/L.

The fermentation medium can also include sodium chloride. Typically, the concentration of sodium chloride in the fermentation medium is within the range of from about 0.1 g/L to about 5 g/L, preferably within the range of from about 1 g/L to about 4 g/L, and more preferably in the range of from about 2 g/L to about 4 g/L.

As previously discussed, the fermentation medium can also include trace metals. Such trace metals can be added to the fermentation medium as a stock solution that, for convenience, can be prepared separately from the rest of the fermentation medium. A suitable trace metals stock solution for use in the fermentation medium is shown below in Table 1. Typically, the amount of such a trace metals solution added to the fermentation medium is greater than about 1 ml/L, preferably greater than about 5 mL/L, and more preferably greater than about 10 mL/L. Beyond certain concentrations, however, the addition of a trace metals to the fermentation medium is not advantageous for the growth of the microorganisms. Accordingly, the amount of such a trace metals solution added to the fermentation medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

As shown below in Table 1, a suitable trace metals solution for use in the present invention can include, but is not limited to ferrous sulfate, heptahydrate; cupric sulfate, pentahydrate; zinc sulfate, heptahydrate; sodium molybdate, dihydrate; cobaltous chloride, hexahydrate; and manganous sulfate, monohydrate. Hydrochloric acid is added to the stock solution to keep the trace metal salts in solution.

TABLE 1

TRACE METALS STOCK SOLUTION

| COMPOUND | CONCENTRATION (mg/L) |
|---|---|
| Ferrous sulfate heptahydrate | 280 |
| Cupric sulfate, pentahydrate | 80 |
| Zinc (II) sulfate, heptahydrate | 290 |
| Sodium molybdate, dihydrate | 240 |
| Cobaltous chloride, hexahydrate | 240 |
| Manganous sulfate, monohydrate | 170 |
| Hydrochloric acid | 0.1 ml |

The fermentation medium can also include vitamins. Such vitamins can be added to the fermentation medium as a stock solution that, for convenience, can be prepared separately from the rest of the fermentation medium. A suitable vitamin stock solution for use in the fermentation medium is shown below in Table 2. Typically, the amount of such vitamin solution added to the fermentation medium is greater than 1 ml/L, preferably greater than 5 ml/L and more preferably greater than 10 ml/L. Beyond certain concentrations, however, the addition of vitamins to the fermentation medium is not advantageous for the growth of the microorganisms. Accordingly, the amount of such a vitamin solution added to the fermentation medium is typically less than about 50 ml/L, preferably less than 30 ml/L and more preferably less than 20 ml/L. It should be noted that, in addition to adding vitamins in a stock solution, the individual components can be added separately each within the ranges corresponding independently to the amounts of the components dictated by the above ranges of the vitamin stock solution.

As shown in Table 2, a suitable vitamin solution for use in the present invention can include, but is not limited to, biotin, calcium pantothenate, inositol, pyridoxine-HCl and thiamine-HCl.

TABLE 2

| COMPOUND | CONCENTRATION (mg/L) |
| --- | --- |
| Biotin | 10 |
| Calcium pantothenate | 120 |
| Inositol | 600 |
| Pyridoxine-HCl | 120 |
| Thiamine-HCl | 120 |

As stated above, when an organism is blocked in the sterol pathway, an exogenous sterol must be added to the fermentation medium. Such sterols include, but are not limited to, ergosterol and cholesterol. Such sterols can be added to the fermentation medium as a stock solution that is prepared separately from the rest of the fermentation medium. Sterol stock solutions can be prepared using a detergent to aid in solubilization of the sterol. A typical ergosterol stock solution is described in Example 1.D. Typically, an amount of sterol stock solution is added to the fermentation medium such that the final concentration of the sterol in the fermentation medium is within the range of from about 1 mg/L to 3000 mg/L, preferably within the range from about 2 mg/L to 2000 mg/L, and more preferably within the range from about 5 mg/L to 2000 mg/L.

Microorganisms of the present invention can be cultured in conventional fermentation modes, which include, but are not limited to, batch, fed-batch, cell recycle, and continuous. It is preferred, however, that the fermentation be carried out in fed-batch mode. In such a case, during fermentation some of the components of the medium are depleted. It is possible to initiate the fermentation with relatively high concentrations of such components so that growth is supported for a period of time before additions are required. The preferred ranges of these components are maintained throughout the fermentation by making additions as levels are depleted by fermentation. Levels of components in the fermentation medium can be monitored by, for example, sampling the fermentation medium periodically and assaying for concentrations. Alternatively, once a standard fermentation procedure is developed, additions can be made at timed intervals corresponding to known levels at particular times throughout the fermentation. As will be recognized by those in the art, the rate of consumption of nutrient increases during fermentation as the cell density of the medium increases. Moreover, to avoid introduction of foreign microorganisms into the fermentation medium, addition is performed using aseptic addition methods, as are known in the art. In addition, a small amount of anti-foaming agent may be added during the fermentation.

The temperature of the fermentation medium can be any temperature suitable for growth and production of farnesol or GG. For example, prior to inoculation of the fermentation medium with an inoculum, the fermentation medium can be brought to and maintained at a temperature in the range of from about 20° C. to about 45° C., preferably to a temperature in the range of from about 25° C. to about 40° C., and more preferably in the range of about 28° C. to about 32° C.

The pH of the fermentation medium can be controlled by the addition of acid or base to the fermentation medium. In such cases when ammonia is used to control pH, it also conveniently serves as a nitrogen source in the fermentation medium. Preferably, the pH is maintained from about 3.0 to about 8.0, more preferably from about 3.5 to about 7.0, and most preferably from about 4.0 to about 6.5.

The fermentation medium can also be maintained to have a dissolved oxygen content during the course of fermentation to maintain cell growth and to maintain cell metabolism for production of farnesol or GG. The oxygen concentration of the fermentation medium can be monitored using known methods, such as through the use of an oxygen electrode. Oxygen can be added to the fermentation medium using methods known in the art, for, through agitation and aeration of the medium by stirring, shaking or sparging. Preferably, the oxygen concentration in the fermentation medium is in the range of from about 20% to about 100% of the saturation value of oxygen in the medium based upon the solubility of oxygen in the fermentation medium at atmospheric pressure and at a temperature in the range of from about 20° C. to about 40° C. Periodic drops in the oxygen concentration below this range may occur during fermentation, however, without adversely affecting the fermentation.

Although aeration of the medium has been described herein in relation to the use of air, other sources of oxygen can be used. Particularly useful is the use of an aerating gas which contains a volume fraction of oxygen greater than the volume fraction of oxygen in ambient air. In addition, such aerating gases can include other gases which do not negatively affect the fermentation.

In an embodiment of the fermentation process of the present invention, a fermentation medium is prepared as described above and in Example 1.H. This fermentation medium is inoculated with an actively growing culture of microorganisms of the present invention in an amount sufficient to produce, after a reasonable growth period, a high cell density. Typical inoculation cell densities are within the range of from about 0.01 g/L to about 10 g/L, preferably from about 0.2 g/L to about 5 g/L and more preferably from about 0.05 g/L to about 1.0 g/L, based on the dry weight of the cells. In production scale fermentors, however, greater inoculum cell densities are preferred. The cells are then grown to a cell density in the range of from about 10 g/L to about 100 g/L preferably from about 20 g/L to about 80 g/L, and more preferably from about 50 g/L to about 70 g/L. The residence times for the microorganisms to reach the desired cell densities during fermentation are typically less than about 200 hours, preferably less than about 120 hours, and more preferably less than about 96 hours.

In one mode of operation of the present invention, the carbon source concentration, such as the glucose concentration, of the fermentation medium is monitored during fermentation. Glucose concentration of the fermentation medium can be monitored using known techniques, such as, for example, use of the glucose oxidase enzyme test or high pressure liquid chromatography, which can be used to monitor glucose concentration in the supernatant, e.g., a cell-free component of the fermentation medium. As stated previously, the carbon source concentration should be kept below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the fermentation medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the fermentation medium by addition of aliquots of the original fermentation medium. The use of aliquots of the original fermentation medium may be desirable because the concentrations of other nutrients in the medium (e.g. the nitrogen and phosphate sources) can be maintained simultaneously. Likewise, the trace metals concentrations can be maintained in the fermentation medium by addition of aliquots of the trace metals solution.

5.0 Farnesol and GG Recovery

Once farnesol or GG are produced by a biological system, they are recovered or isolated for subsequent use. The present inventors have shown that for both farnesol and GG, the product may be present in culture supernatants and/or associated with the yeast cells. With respect to the cells, the recovery of farnesol or GG includes some method of permeabilizing or lysing the cells. The farnesol or GG in the culture can be recovered using a recovery process including, but not limited to, chromatography, extraction, solvent extraction, membrane separation, electrodialysis, reverse osmosis, distillation, chemical derivatization and crystallization. When the product is in the phosphate form, i.e., farnesyl phosphate or geranylgeranyl phosphate, it only occurs inside of cells and therefore, requires some method of permeabilizing or lysing the cells.

The following Examples are provided to illustrate embodiments of the present invention and are not intended to limit the scope of the invention as set forth in the claims.

EXAMPLES

Example 1

This example describes the creation of erg9 mutants by chemical mutagenesis of S. cerevisiae strain ATCC 28383 using nitrous acid.

As noted above, one way of increasing yields of farnesol or GG is to decrease or eliminate squalene synthase activity. In S. cerevisiae, squalene synthase is encoded by the ERG9 gene.

A. Mutagenesis

Strain 28383 was obtained from the ATCC. It is the parent of strain 60431 used below in some experiments for comparative purposes (also obtained from ATCC). Strain 60431 is an erg9-1 mutant that produces farnesol.

A kill curve was performed using nitrous acid with ATCC 28383. Using information derived from the kill curve, a mutagenesis of ATCC 28383 with nitrous acid was performed as follows. The 28383 cells were incubated overnight at 30° C. in YPD medium (1% Bacto-yeast extract, 2% Bacto-peptone, and 2% glucose) with shaking. The cells were washed and mutagenized. After mutagenesis, the cells were allowed to recover by culturing them in YPDC (YPD plus 4 mg/L cholesterol) at 22° C. overnight. The culture was then washed and plated onto YPDC agar (YPDC plus 2% Bacto-agar) containing various levels of nystatin (20, 30, 40, 50 mg/L). These cultures were incubated for two weeks at 22° C. The antifungal polyene antibiotic nystatin inhibits cell wall synthesis in growing cells by binding specifically to ergosterol, which, in turn, results in an alteration of selective permeability. Some strains that are resistant to nystatin have been shown to have decreased production of ergosterol. Nystatin has little, if any, affinity for cholesterol which, when supplied exogenously, can be used by sterol auxotrophs as efficiently as ergosterol.

Approximately 3,000 nystatin-resistant colonies were obtained. They were screened for temperature sensitivity (ts) and sterol auxotrophy. To determine temperature sensitivity, mutagenized cells were grown on YPDC at a permissive temperature (22° C.) and subsequently replica plated to YPD agar and incubated at a restrictive temperature (37° C.). Any cells which fail to grow at the higher temperature would include those with both a conditionally lethal and a constitutively lethal defect in the sterol pathway. Temperature sensitive mutants were screened for sterol auxotrophy by replica plating to YPD agar (lacking cholesterol) and incubation overnight at 28° C. Of the 3,000 nystatin-resistant colonies, 170 were saved after confirmation of ts and sterol auxotrophy.

B. Tube Assays

The 170 strains were initially evaluated in tube assays for the production of farnesol and other intermediates of the isoprenoid pathway as follows. Cells were cultured in 10 ml YPDC in tubes with screw caps for 48 hours at 28° C. with shaking. The cells were centrifuged for 5-10 minutes at 2800 rpm, and the supernatant was transferred to another tube. The cells were washed once with 5 ml distilled water and centrifuged again for 5-10 minutes at 2800 rpm.

The cell pellet was extracted by adding 2.5 ml 0.2% pyrogallol (in methanol) and 1.25 ml 60% KOH (in distilled $H_2O$), vortexing to mix, and incubating in a 70-75° C. water bath for 1.5 hours. After this saponification, 5 ml hexane were added, and the tube was recapped and vortexed for 15-30 seconds. The tube was centrifuged at 2800 rpm for 5 minutes to separate the phases. The hexane layer was recovered. If necessary, the sample can be concentrated by evaporating solvent under nitrogen and adding back an appropriate amount of hexane for analysis.

To extract the supernatant, 5 ml of hexane were added to the supernatant, and the tube was recapped and vortexed for 15-30 seconds. The tube was centrifuged at 2800 rpm for 25 minutes to separate phases. The hexane layer was recovered, and the sample was concentrated by evaporating under nitrogen and adding back an appropriate amount of hexane for analysis.

The hexane extracts from this primary screen were analyzed by thin layer chromatography (TLC) with confirmation by gas chromatography (GC)/mass spectrometry (MS) for the presence of farnesol and other intermediates of the isoprenoid pathway. TLC was performed on reversed-phase C18 silica gel plates using 6:4 (v/v) ethylacetate/acetonitrile (EtOAc/MeCN) as the mobile phase and 2% (w/v) phosphomolybdic acid (PMA) in ethanol for detection. GC/MS was performed using a Hewlett Packard 5890 GC and a 5970 series mass selective detector. The column used was a Restek Rtx-5MS (15 m length, 0.25 mm ID, 1 μm film system. Thirteen mutants were identified as producers of farnesol or other intermediates.

C. Shake Flask Assays

These thirteen mutants were then screened in shake flasks, along with the parental strain, 28383, and the farnesol producing strain, 64031. Fifty ml of YPDC medium in 250 ml baffled Erlenmeyer flasks were inoculated with overnight cultures to an initial OD at 600 nm of 0.05 and incubated with shaking at 28° C. The flasks were sampled, and OD at 600 nm, dry weight and sterol content were determined. To measure dry weight, 5 ml of the culture were centrifuged at 8,000 rpm. The cells were washed twice with distilled $H_2O$, and the cell pellet was resuspended in 3-5 ml distilled $H_2O$ and transferred to a pre-weighed dry weight pan. The pan was placed in 100° C. oven for 24 hours, then cooled in a desiccator, weighed on an analytical balance, and the dry weight in g/L determined from the formula:

[Total weight (pan+cells)−pan weight]×200=dry weight in g/L.

For sterol determination, 20 ml of culture were processed, the cell pellet and supernatant extracted, and farnesol and other sterols measured as described above.

Seven of the 13 mutants appeared to produce intermediates in the ergosterol pathway and were evaluated further in other shake flask experiments (see below). All 13 mutants had been selected by resistance to the highest levels of nystatin.

Overnight cultures were used to inoculate 50 ml of YPDC medium in triplicate shake flasks for each of the seven mutant strains (MBNA1-1, MBNA1-5, MBNA1-9, MBNA1-10, MBNA1-11, MBNA1-13, MBNA1-14), the parental strain 28383 and mutant strain 64031. The cells and medium were extracted separately at 24, 48, and 72 hours into hexane, as described above. Dry weight analysis (performed as described above) was performed at each of these time points to determine cell density. The hexane extracts were analyzed by GC/MS for their farnesol, squalene, cholesterol, and ergosterol levels. The farnesol results are presented in Table 3 below.

Low levels of farnesol were found in the culture supernatants with much higher levels accumulating in the cells. Strain MBNA1-1 produced 1% farnesol and also made 0.1% ergosterol at 72 hours. Strain MBNA1-5 did not make any farnesol, but produced 0.3% squalene. Strain MBNA1-9 produced 0.64% farnesol in 48 hours. MBNA1-10, MBNA1-11, and MBNA1-14 produced very low levels of farnesol in the cells and appeared to make ergosterol. MBNA1-13 showed the highest farnesol production (2.5%) based on cell dry weight (42,187 ng/ml culture) and did not show any ergosterol production. Thus, among the farnesol-producing strains (MBNA1-1, MBNA1-9 and MBNA1-13), there appeared to be different degrees of blockage in the ergosterol pathway, since MBNA1-1 and MBNA1-9 produced lower levels of farnesol and did not require ergosterol for growth, and MBNA1-13 produced the highest level of farnesol and had a strict requirement for sterol supplementation for growth. The parental strain 28383 showed ergosterol production up to 0.4% (no farnesol production), and erg9 mutant strain 64031 showed farnesol accumulation to approximately 0.4%.

TABLE 3

Characterization of New Mutants in Shake Flask Experiment

| Strain Name | Hours of Growth | Dry weight mg/ml | Farnesol (ng/ml of culture) | Farnesol (% of cell dry weight) |
|---|---|---|---|---|
| MBNA1-1 | 24 | 0.16 | 0 | 0.00 |
|  | 48 | 1.12 | 1793 | 0.16 |
|  | 72 | 1.26 | 13187 | 1.05 |
| MBNA1-5 | 24 | 2.46 | 0 | 0.00 |
|  | 48 | 1.6 | 0 | 0.00 |
|  | 72 | 1.06 | 0 | 0.00 |
| MBNA1-9 | 24 | 1.32 | 1122 | 0.09 |
|  | 48 | 2.96 | 19062 | 0.64 |
|  | 72 | 4.34 | 70625 | 0.00 |
| MBNA1-10 | 24 | 4.76 | 4636 | 0.10 |
|  | 48 | 9.44 | 444 | 0.00 |
|  | 72 | 7.9 | 166 | 0.00 |
| MBNA1-11 | 24 | 1.82 | 0 | 0.00 |
|  | 48 | 3.58 | 258 | 0.01 |
|  | 72 | 2.36 | 281 | 0.01 |

TABLE 3-continued

Characterization of New Mutants in Shake Flask Experiment

| Strain Name | Hours of Growth | Dry weight mg/ml | Farnesol (ng/ml of culture) | Farnesol (% of cell dry weight) |
|---|---|---|---|---|
| MBNA1-13 | 24 | 0.18 | 0 | 0.00 |
|  | 48 | 3.12 | 3657 | 0.12 |
|  | 72 | 1.66 | 42187 | 2.54 |
| MBNA1-14 | 24 | 2.42 | 0 | 0.00 |
|  | 48 | 8.98 | 0 | 0.00 |
|  | 72 | 7.36 | 0 | 0.00 |
| ATCC28383 | 24 | 7.36 | 0 | 0.00 |
|  | 48 | 8.52 | 0 | 0.00 |
|  | 72 | 8.84 | 0 | 0.00 |
| ATCC64031 | 24 | 1.58 | 90 | 0.01 |
|  | 48 | 1.84 | 6845 | 0.37 |
|  | 72 | 1.28 | 4874 | 0.38 |

D. Enzyme Analysis

For all enzyme assays, cells were grown in YPDE medium. (YPD medium containing 5 mg/L ergosterol). The cells were harvested by centrifugation. One gram of cells (wet weight) was suspended in 4 ml of 0.1 M Tris·HCl, pH 7.0. The cell suspension was then disrupted by passage through a French pressure cell (20,000 psi). The resulting (lysed) cell suspension was then centrifuged (15,000×g) and the supernatant (cell free extract) was used directly for enzyme assays unless noted otherwise.

The mutants were assayed for squalene synthase activity. The squalene synthase assay involved incubation of a cell-free extract with FPP in the presence the reduced form of nicotinamide adenine dinucleotide phosphate, (NADPH), extraction into ethyl acetate, and squalene detection by GC. Specifically, 0.1 M Tris/HCl pH7 (X µL), 0.1 M DTT (2 µL), 0.1 M $MgCl_2$ (10 µL), 0.1 M NADPH (4 µL), 1 mg/mL FPP (6 µL), and cell-free extract (7000×g supernatant) (Y µL), where X+Y=178 µL to make 200 µL total, were combined. This mixture was incubated in glass tubes at 37° C. for 40 min. Then, it was extracted with 0.15 mL ethyl acetate. The extract was transferred to plastic vials and centrifuged at 15,000×g for 5 min. The ethyl acetate extract was analyzed using GC/MS.

Table 4 shows squalene synthase levels for mutants MBNA1-1, MBNA1-9, MBNA1-13, and ATCC strains 64031 and 28383. Squalene synthase activity was 0.12 µg squalene formed/min×mg protein for the wild-type organism 28383. The activity levels for the other four strains were less than the detectable limits of this assay. Reduced squalene synthase levels would be expected for MBNA1-1, MBNA1-9 and 64031 since they have been characterized as being partially-blocked mutants that produce farnesol and low amounts of ergosterol. MBNA1-13 is a farnesol-producing mutant which cannot grow without added sterol, so this blocked mutant would be expected to have no detectable level of squalene synthase. The extracts of these strains were reassayed with higher concentrations of cell-free extract and longer incubation times. Once again, squalene synthase was not detected in any of the mutants.

TABLE 4

| Strain | Squalene Synthase Assay (µg/min × mg protein) |
|---|---|
| MBNA1-1 | ND |
| MBNA1-9 | ND |
| MBNA1-13 | ND |

TABLE 4-continued

| Strain | Squalene Synthase Assay (μg/min × mg protein) |
|---|---|
| ATCC 64031 | ND |
| ATCC 28383 | 0.12 |

ND = Not detected

An enzyme analysis was performed for the farnesol-producing strains (MBNA1-1, MBNA1-9 and MBNA1-13) and their parental strain, 28283. The enzyme levels compared were those of the acetoacetyl CoA thiolase, HMG-CoA synthase, HMG-CoA reductase, FPP synthase, and a phosphatase. Cell-free extracts were prepared as described above.

For the FPP synthase assay, 0.1 M DTT (2 μL), 0.1 M $MgCl_2$ (2 μL), 1 mg/mL IPP (6 μL), 1 mg/mL GPP (6 μL), cell-free extract (Y), and 0.1 M Tris/HCl (pH 7.0) (X μL), where X+Y=84 μL, were combined, and incubated at 37° C. for 15 min. This mixture was then extracted twice with 0.3 mL hexane to remove pre-existing farnesol. Next, 0.1 mL of 2× glycine buffer (0.2 M glycine, 2 mM $MgCl_2$, 2 mM Zn $Cl_2$), pH 10.4, and 33 units of alkaline phosphatase were added, and the mixture was incubated at 37° C. for an hour. The mixture was extracted with 0.1 mL of ethyl acetate and dried with sodium sulfate. Farnesol was determined with GC. A no-phosphatase control was included in each assay.

HMG-CoA reductase catalyzes the reaction of HMG-CoA with NADPH to form mevalonate, nicotinamide adenine dinucleotide phosphate (NADP) and CoA (see FIG. 1). For these assays, the cell-free extracts were prepared as described above except that the disrupted cell suspensions were centrifuged at 7,000×g instead of 15,000×g. The reaction was followed by monitoring consumption of HMG-CoA by high performance liquid chromatography (HPLC). For the assay, a reaction mixture containing (in a final volume of 0.1 ml) 0.1 M $Na_2H_2P_2O_7$, pH 6.5, 2 mM DTT, 1 mM NADPH, 0.4 mM HMG-CoA, and cell-free extract (the volume of extract was varied, with the balance of the 0.1 ml reaction made up with 0.1 M $Na_2H_2P_2O_7$, pH 6.5) was incubated at 37° C. for 15 minutes. The reaction was monitored with HPLC (Luna C18 (Phenomenex) reversed-phase column using a gradient of 0% Solvent B for 1 min. followed by 0-11% B over 42 min. Solvent A was 86:14 (v/v) 40 mM potassium phosphate (pH 6.0)/methanol. Solvent B was methanol. The wavelength for detection was 260 nm).

HMG-CoA synthase converts acetoacetyl CoA and acetyl CoA to HMG-CoA and CoA. The assay monitors the production of HMG-CoA by HPLC. For the assay, 0.1 M $Na_2H_2P_2O_7$, pH 6.5, (X μL), 20 mM acetoacetyl CoA (4 μL), 20 mM acetyl CoA (2 μL), and cell-free extract (Y μL), where X+Y is 94 μL (total volume 100 μL), were combined and incubated at 37° C. for 5 minutes. Then, the reaction mixture was heated at 60° C. for 5 minutes to inactive the enzyme, followed by centrifugation in a microfuge at full speed for 5 minutes. The supernatant was analyzed by HPLC.

Acetoactyl CoA thiolase catalyzes a reversible reaction whereby, in the forward direction, two molecules of acetyl CoA are reacted to form acetoacetyl CoA and CoA. The assay monitors the formation of acetyl CoA (reverse reaction) by HPLC. For the assay, 0.1 M $Na_2H_2P_2O_7$, pH 6.5, (X μL), 20 mM acetoacetyl CoA (2 μL), 20 mM CoA (3 μL), and cell-free extract (Y μL), where X+Y is 95 μL (total volume 100 μL), were combined and incubated at 37° C. for 5 minutes. Then, the reaction mixture was centrifuged in a Microcon-10 (Amicon) centrifuge to separate the enzyme from the product. The supernatant was analyzed by HPLC.

The phosphatase assay quantitates phosphatase activity by measuring the formation of p-nitrophenol (increased absorbance at 400 nm). For the phosphatase assay, 0.1 M Tris-HCl, pH 7 (X ul), 1 M $MgCl_2$ (2 ul), 50 mM p-nitrophenyl phosphate (10 ul) and cell-free extract (Y ul), where X+Y=1 mL, were combined and incubated at 37° C. for 15 minutes, after which the absorbance at 400 nm was measured.

Table 5 shows the levels for each of the five enzymes in these four strains. The acetoacetyl CoA thiolase levels were comparable in all of these strains. The HMG-CoA synthase and HMG-CoA reductase levels appeared to be two to three times higher in the mutant strains. The FPP synthase levels were the same or lower in the mutants than in 28383. The phosphatase levels appeared to be elevated three to four fold in the mutant strains compared to the parent. Since all of these strains were isolated by classical mutagenesis, it is possible that other mutations exist in these strains, besides the erg9 mutation.

TABLE 5

|  | MBNA1-1 | MBNA1-9 | MBNA1-13 | ATCC 28383 |
|---|---|---|---|---|
| Acetoacetyl CoA Thiolase (nmol AcCoA/min × mg protein) | $2.4 \times 10^2$ | $2.7 \times 10^2$ | $1.6 \times 10^2$ | $2.0 \times 10^2$ |
| HMG-CoA Synthase (nmol HMG-CoA/ min × mg protein) | 5.7 | 7.2 | 7.1 | 2.7 |
| HMG-CoA Reductase (nmol CoA/min × mg protein) | 0.35 | 0.55 | 0.36 | 0.15 |
| FPP Synthase (nmol Farnesol/ min × mg protein) | 1.3 | 2.0 | 1.6 | 2.2 |
| General Phosphatase (nmol p-nitrophenol/ min × mg protein) | 82 | 83 | 91 | 24 |

E. ERG9 Genetic Analysis

Chromosomal DNA was prepared from strains ATCC 28383, MBNA1-1, MBNA1-9 and MBNA1-13 according to the method described in Sherman et al. (Sherman, F., G. R. Fink, and J. B. Hicks, 1989, Methods in Yeast Genetics, Cold Spring Harbor Laboratories, Cold Spring Harbor, N.Y.). The genomic DNA was digested with the restriction enzymes ApaI and NsiI, and subjected to Southern blot analysis using a biotinylated ERG9 DNA fragment as a probe. The ERG9 probe consisted of a 2044 bp ERG9 DNA fragment isolated from an agarose gel after digestion of the plasmid pTWM103 with ApaI and NsiI. pTWM103 consists of the ERG9 gene and flanking sequences extending from position #10916 to #13868 of GenBank Accession #U00030 sequence. This plasmid was constructed by polymerase chain reaction (PCR) amplification of the ERG9 gene and flanking regions using the following two oligonucleotides:

```
5'-oligo = VE107-5 CTC AGT ACG CTG GTA CCC GTC AC
(denoted herein as SEQ ID NO:1)

3'-oligo = VE105-3 gat gga TCC CAA TAT GTG TAG CTC
AGG (denoted herein as SEQ ID NO:2)
```

Capital letters designate DNA sequences from ERG9 flanking region, while small letters designate bases added to create restriction sites. VE107-5 contains sequences from position #10905 to position #10928 of GenBank Accession

U00030 sequence. VE105-3 contains the reverse complement of sequences from position #13868 to position #13847.

The amplification conditions were as follows:

Template DNA was genomic DNA isolated from strain S288C (Yeast Genetic Stock Center, Berkeley, Calif.)

2 min. 94° C./1 cycle 1 min. 94° C., 1 min. 52° C., 1.5 min. 74° C./30 cycles 5 min. At 74° C./1 cycle The 2969 bp ERG9 DNA generated from this PCR reaction was digested with KpnI and BamHI, then ligated to KpnI, BamHI digested YEp352 to generate plasmid pTWM103. YEp352 is a yeast/*E. coli* shuttle vector (Hill, J. E., Myers, A. M., Koerner, T. J., and Tzagaloff, A., 1986, Yeast/*E. coli* Shuttle Vectors with Multiple Unique Restriction Sites, Yeast 2: 163-167).

DNA for the ERG9 probe described above was obtained by digesting TWM103 with ApaI and NsiI, and purifying the 2044 bp fragment containing the ERG9 gene and flanking sequences. The ERG9 DNA was then biotinylated using random primer extension (NEBlot Phototope Kit, New England BioLabs, Beverly, Mass.).

Approximately 1 μg of biotinylated ERG9 probe was hybridized to the Southern blot of ApaI, NsiI digested genomic DNA from strains ATCC 28383, MBNA1-1, MBNA1-9, and MBNA1-13. The blot revealed that all four strains contained a single hybridizing sequence located on a 2044 bp fragment.

To clone the ERG9 genes from these four strains, genomic DNA from each was again digested with ApaI and NsiI. The yeast/*E. coli* shuttle vector pRS315 (Sikorski, R. S., and P. Hieter, 1989, A System of Shuttle Vectors and Yeast Host Strains Designed for Efficient Manipulation of DNA in *Saccharomyces cerevisiae*, Genetics, 122: 19-27) was digested with ApaI and PstI (NsiI and PstI have compatible cohesive ends). The digested DNAs were separated on an agarose gel, and chromosomal DNA fragments in the size range from approximately 1.6 kb to approximately 3 kb, as well as the 3895 bp band corresponding to digested pRS316 were cut from the gel and purified using GeneClean (BIO 101, Inc., Visa, Calif.). The purified genomic DNA fragments from each of the four strains was ligated to pRS316, and transformed into *E. coli*. Transformants containing the pRS316/ ERG9 clones were identified by colony hybridization using the ERG9 probe described above. ERG9 clones derived from each of the four strains were isolated in this manner. The cloned ERG9 genes from each strain were sequenced by ACGT, Inc., Northbrook, Ill., using an Applied Biosystems, Inc. automated DNA sequencer, Model ABI 100.

The sequence of the ERG9 gene from ATCC 28383 was identical to the sequence deposited in GenBank (Accession #U00030). The erg9 genes from MBNA1-2 and MBNA1-9 were found to have the same mutation, namely, a change from G to A at position #12386 of GenBank Accession #U00030, which changes a TGG codon to a TGA stop codon. This causes termination of the ERG9 protein at 237 amino acids instead of the normal 444 amino acids found in the wild-type ERG9 protein.

The erg9 gene from MBNA1-13 was found to contain a deletion of a C at position #12017 of GenBank Accession #U00030, which causes a frameshift and early termination of the ERG9 protein at 116 amino acids, with the last two amino acids being different from the wild-type ERG9 protein (due to the frameshift). The erg9 alleles from MBNA1-1 and MBNA1-9 retain low levels of activity. This was determined by transforming an ergosterol-requiring erg9 deletion mutant with plasmids that carry the mutant erg9 genes from MBNA1-1 and MBNA1-9. The presence of the cloned genes in the erg9 deletion strains allowed these transformants to grow, albeit slowly, on medium lacking ergosterol. The erg9 allele from MBNA1-13 did not show any residual activity when tested in this manner. The erg9 deletion strain grew at wild-type levels when transformed with the ERG9 allele from ATCC 28383.

F. Description of Secondary Mutations

*Saccharomyces cerevisiae* does not normally import ergosterol from its environment under aerobic conditions. However, the isolated erg9 mutants were able to grow aerobically when supplemented with ergosterol or cholesterol, and therefore, must contain secondary mutations that allow aerobic sterol uptake to occur. The methods used to isolate ergosterol pathway mutants, such as the erg9 mutant MBNA1-13, included not only a selection for ergosterol pathway mutants, but a selection for cells that import sterols under aerobic conditions as well, since only mutants with mutations in both a sterol pathway gene and a sterol uptake gene would have survived.

In Example 3 below, the difficulty encountered when attempting to obtain erg9 knockout mutations by molecular methods, even in a strain carrying the upc2 mutation, which is reported to allow uptake of sterols under aerobic conditions (Lewis, T. L., G. A. Keesler, G. P. Fenner and L. W. Parks, 1988, Pleiotropic mutations in *Saccharomyces cerevisiae* affecting sterol uptake and metabolism, Yeast 4:93-106) is described. It appears that the upc2 mutation does not confer efficient aerobic sterol uptake in an erg9 mutant, and that the strains described in Example 3 acquired additional spontaneous mutations (at a low frequency rate) that improve their ability to take up sterols aerobically.

Having the appropriate mutations that enhance aerobic uptake of ergosterol and cholesterol in an otherwise wild type strain allow one to isolate erg9 mutations in that strain at a much higher frequency than would be obtained with a non-sterol uptake mutant strain. In order to demonstrate that the erg9 mutant strain MBNA1-13 (and derivatives of this strain) had acquired a mutation(s) that enhances uptake of sterols under aerobic conditions (referred to as sterol uptake enhancement or sue mutations), the frequency of creating an erg9 knockout in the MBNA1-13 background, which contains the sterol uptake mutation, to the frequency of obtaining the erg9 knockout mutation in the ATCC 28383 parental background, which presumably lacks the sterol uptake mutation, was compared. This was done with the following two strains representing each strain background. SWE23-ΔHE9 (ura3, his3, sue) was derived from MBNA1-13 and contains a repaired ERG9 gene. SWY5-ΔH1 (ura3, his3) is an auxotrophic mutant derived from strain ATCC 28383. The construction of SWE23-ΔHE9 and SWY5-ΔH1 is described in detail in Section G below. Since SWE29-ΔHE9 was derived from MBNA1-13, this strain served as the host carrying the sue mutation, whereas SWY5-ΔH, which was derived from ATCC 28383, served as the host without the sue mutation. Both strains were transformed with equal amounts (approximately 1 μg) of the erg9Δ::HIS3 DNA fragment obtained by digesting pKML19-41 (plasmid construction described in Example 3) with BamHI and XmaI, and purifying the resulting 2.1 kb fragment. Cells were transformed with this 2.1 kb fragment using the LiAc transformation procedure (Gietz, R. D., R. H. Schiestl, A. R. Willems and R. A. Woods, 1995, Studies on the transformation of intact yeast cells by the LiAc/SS-DNA/PEG procedure, Yeast 11: 355-360), and transformants were selected on SCE-ura medium. SCE medium contains 0.67% Bacto yeast nitrogen base (without amino acids), 2% dextrose, 20 mg/L adenine sulfate, 20 mg/L uracil, 20 mg/L L-tryptophan, 20 mg/L L-histidine, 20 mg/L L-arginine, 20 mg/L L-methionine, 30 mg/L L-tyrosine, 30 mg/L L-leucine, 30 mg/L L-isoleucine, 30 mg/L L-lysine, 50 mg/L L-phenylalanine, 100 mg/L L-glutamic acid, 100 mg/L L-aspartic acid, 150 mg/L L-valine, 200 mg/L L-threonine, 400 mg/L L-serine and 5 mg/L ergosterol. For agar plates, 2% Bacto agar is added to the SCE medium. SCE-ura medium is SCE lacking uracil.

A total of 24 HIS+ colonies arose from the transformation of SWY5-ΔH1, while 401 HIS+ colonies were obtained from SWE23-ΔHE9. Since it was possible for the erg9Δ::HIS3 gene to integrate at loci other than the ERG9 locus (and therefore allowing the cells to remain prototrophic for ergosterol), twenty of each type of transformant were tested for an ergosterol requirement by plating onto YPD medium (lacks ergosterol). All 20 of the HIS+ colonies derived from SWY5-ΔH were able to grow on YPD which indicated that they still contained a functional ERG9 gene, and suggested that the erg9Δ::HIS3 gene was not integrated at the ERG9 locus. On the other hand, none of the HIS+ colonies derived from SWE23-ΔHE9 were able to grow on YPD indicating that the erg9Δ::HIS3 DNA had replaced the wild type ERG9 gene in this strain background at a relatively high frequency. To verify this, nine HIS+ colonies of each strain were analyzed by PCR to determine the types of ERG9 alleles present in their genomes. Genomic DNA was prepared as described in Sherman et al. (1989). The oligonucleotides used for the analysis are given below.

```
                                       (SEQ ID NO:3)
5'oligo = 250 UpBam    gcgcatCCACGGGCTATATAAA (SEQ ID NO:4)
3'oligo = 1764 LoBam   gcggatCCTATTATGTAAGTACTTAG
```

PCR conditions were as follows:

94° C., 3 min.

94° C., 30 sec.; 50° C., 30 sec.; 72° C., 3 min.; 30 cycles

72° C., 7 min.

Oligonucleotides 250 UpBam contains sequences corresponding to position #11555 to #11570 of the GenBank Accession #J05091 sequence. Oligo 1764LoBam contains the reverse complement of sequences from position #13049 to #13068 of the same GenBank sequence file. In all 9 of the HIS transformants of SWE23-ΔHE9, the PCR product was 2.1 kbp indicating that the ERG9 gene had been replaced by the erg9Δ::HIS3 gene. In 8 of the 9 HIS transformants of SWY5-ΔH1, the PCR products were 2.1 kbp and 1.5 kbp, indicating that the wild type ERG9 gene remained intact and that the erg9Δ::HIS3 DNA had integrated elsewhere in the genome. The ninth HIS+ transformant showed only the 1.4 kbp PCR product, also indicating that the ERG9 gene was intact in this strain. In this case, the HIS3 gene is believed to have integrated into the genome without carrying all of the erg9 sequences with it.

These results show that during the course of isolating strain MBNA1-13, an additional mutation(s), referred to herein as sue, arose in the strain. Based on the results described in Example 3 below, the sue mutation appear to be different from the previously reported upc2 mutation and confers more efficient uptake of sterols.

G. Derivation of New Strains from MBNA1-13

In order to use the erg9 mutant strain MBNA1-13 for molecular genetic manipulations, the strain was further developed so that it carried auxotrophic markers suitable for this purpose. MBNA1-13 was mutagenized using ethyl methane sulfonate using standard procedures and mutants resistant to 5-fluoroorotic acid (5-FOA) were obtained by plating the mutagenized cells on medium containing 5-FOA. The use of 5-FOA selection was described in Sikorski and Boeke, 1991 (Sikorski, R. S. and Boeke, J. D., 1991, In Vitro Mutagenesis and Plasmid Shuffling: From Cloned Gene to Mutant Yeast, Methods in Enzymology 194: 302-318). This selection method allowed for the isolation of strains containing mutations in the URA3 gene, coding for orotidine-5'-phosphate decarboxylase. Several resistant strains were isolated that exhibited 5-FOA resistance (i.e., a ura⁻ phenotype). To determine which of these strains contained a mutation specifically in the URA3 gene, the ura⁻ strains were transformed with pRS316 (Sikorski and Hieter, 1989), which contains the intact URA3 gene, using the LiOAc transformation procedure (Gietz et al., 1995). Several strains were identified whose lack of growth on medium lacking uracil was restored by pRS316, indicating that those strains carried the ura3 mutation. One of these strains, EMS9-23 (ura3, erg9) was chosen for further modification.

Strain EMS9-23 was genetically altered to contain deletions in leu2, trp1, or his3 genes using gene transplacement plasmids described in Sikorski and Hieter 91989), and the pop-in/pop-out gene replacement procedure described in Rothstein (1991) (Rothstein, R., 1991, Targeting, Disruption, Replacement, and Allele Rescue: Integrative DNA Transformation in Yeast, Methods in Enzymology 194: 281-301). The leu2, trp1 and his3 mutants derived from MBNA 1-13 were named SWE23-ΔL1, SWE23-ΔT1 and SWE23-ΔH1, respectively. Strain SWE23-ΔH1 was further manipulated to exchange the original erg9 frameshift mutation (see Section E) with the erg9Δ::HIS3 allele. This was done by transforming SWE23-ΔH1 (using the LiOAc procedure) with approximately 5 μg of a linear DNA fragment containing the erg9Δ::HIS3 cassette (the construction of the erg9Δ::HIS3 cassette is described in detail in Example 3). The erg9Δ::HIS3 cassette was obtained by digesting pKML19-40 with BamHI and XmaI, and purifying the 2.1 kbp DNA fragment containing the erg9Δ::HIS3 fragment. Transformants of SWE23-ΔH1 in which the erg9 frameshift allele had been replaced by the erg9Δ::HIS3 allele were selected by plating the transformants on SCE medium lacking histidine. One of the resulting strains is referred to as SWE23-ΔE91.

Strain SWE23-DH1 was further modified so as to contain mutations in the leu2 and trp1 genes. These mutations were introduced using the gene transplacement plasmids (Sikorski and Hieter, 1981) and the pop-in/pop-out gene replacement procedure (Rothstein 1991) described above. One of the resulting strains is referred to as SW23-DH1 #42, and contains erg9, ura3, his3, leu2, trp1, and sue mutations. Strain SW23-DH1 #42 was further modified to exchange the original erg9 frameshift mutation with the erg9D::HIS3 allele. This was done by transforming SW23-DH1 #42 (using the LiOAc procedure) with approximately 5 mg of a linear DNA fragment containing the erg9D::HIS3 cassette as described above. HIS+ transformants in which the erg9 frameshift mutation had been replaced by the erg9D::HIS3 allele were selected on SCE-his medium. One of the resulting strains is referred to as SW23B, and carries mutations in the following genes ura3, leu2, trp1, his3, erg9::HIS3, sue.

A summary of the strains derived from MBNA1-13 and their respective farnesol production in shake flask cultures is given in Table 6. The strains were grown overnight in YPDE medium (30° C. with shaking at 180 rpm). These cultures were used to inoculate 25 ml of YPDE medium in a 250 ml flask such that the initial $OD_{600}$ was 0.05. The cells were grown for 72 hours at 30° C. (with shaking at 180 rpm). Samples of the whole broth (i.e., cells plus culture medium) were analyzed for dry cell weight and farnesol as described in Section C above.

TABLE 6

Growth and Farnesol Production in Strains Derived from MBNA1-13

| Strain | Genotype | Farnesol (% of dry cell weight) |
|---|---|---|
| MBNA1-13 | erg9, sue | 7.9 |
| EMS9-23 | erg9, ura3, sue | 8.0 |
| SWE23-ΔH1 | erg9, ura3, his3-Δ200, sue | 7.9 |
| SWE23-ΔL1 | erg9, ura3, leu2-Δ1, sue | 9.3 |
| SWE23-ΔT1 | erg9, ura3, trp1-Δ63, sue | 10.8 |
| SWE23-ΔE91 | erg9Δ::HIS3, ura3, his3, sue | 8.0 |

Strains MBNA1-13, EMS9-23 and SWE23-ΔE91 were further evaluated for growth and farnesol production in 1-L fermentors using the method described in Section H below. EMS9-23 and SWE23-ΔE91 were each transformed with plasmid YEp352, which contains the cloned URA3 gene. This obviated the need to add uracil to the fermentation medium for these two strains. FIG. 2 and Table 7 summarize the results of these fermentations. MBNA1-13 and EMS9-23/YEp352 performed similarly. Although the growth of SWE23-ΔE91/YEp352 lagged behind the other two strains, it did reach a cell density and farnesol production level comparable to the other strains.

TABLE 7

Comparison of MBNA1-13 and Strains Derived from it in 1-L Fermentors

| Strain/Plasmid | Time (hr) | Dry Cell Weight (g/L) | Farnesol g/L | Farnesol (% of dry cell weight) |
|---|---|---|---|---|
| MBNA1-13 | 191 | 40.8 | 2.25 | 5.5 |
| EMS9-23/YEp352 | 191 | 42.6 | 2.46 | 5.8 |
| SWE23-ΔE91/YEp352 | 239 | 37.2 | 2.23 | 6.0 |

Strains EMS9-23 and SWE23-ΔH1 were further manipulated by repairing their erg9 mutations back to wild type function. This was done by transforming the two strains (using the LiOAc transformation procedure) with approximately 5 μg of a DNA fragment containing the intact ERG9 gene. The ERG9 gene DNA fragment was obtained by digesting pTWM103 (see Section E above) with SacI and BamHI, and purifying the 2.5 kb DNA fragment containing the ERG9 gene. Transformants of EMS9-23 and SWE23-ΔH1 in which the erg9 frameshift mutation had been replaced by the wild type ERG9 gene were obtained from each strain by selecting for cells that could grow on YPD medium lacking ergosterol. One erg9-repaired strain derived from EMS9-23, designated SWE23-E9, and one erg9-repaired strain derived from SWE23-ΔH1, designated SWE23-ΔHE9, were chosen for further study. In separate experiments, auxotrophic mutations were introduced into the parental strain ATCC 28383. A spontaneous ura3 mutant of ATCC 28383 was obtained after plating cells on medium containing 5-FOA as described above. Mutants resistant to 5-FOA were transformed with pRS316 (described above) to identify those that had spontaneously acquired a mutation specifically in their URA3 gene. One strain, SWY5, exhibited a stable ura⁻ phenotype (low reversion frequency), and was chosen for further study. SWY5 was further manipulated to carry the his3 mutation by using the gene transplacement plasmid YRp14/his3-Δ200 described by Sikorski and Hieter (Sikorski and Hieter, 1989) and the pop-in/pop-out gene replacement procedure described by Rothstein (Rothstein, 1991). One his3 mutant derived from SWY5, designated SWY5-ΔH, was chosen for further study.

Table 8 lists the repaired and auxotrophic strains described and their genotypes.

TABLE 8

Repaired and Auxotrophic Strains related to ATCC 28383 and MBNA1-13

| Strain | Genotype | Parent |
|---|---|---|
| SWE23-E9 | ura3, sue | EMS9-23 |
| SWE23-ΔHE9 | ura3, his3, sue | SWE23-ΔH1 |
| SWY5 | ura3 | ATCC 28383 |
| SWY5-ΔH | ura3, his3 | SWY5 |

To test whether the erg9 mutant MBNA1-13 had acquired any additional nutritional requirements during the course of its isolation, a growth experiment was conducted in shake flasks to compare the parental strain ATCC 28383, the erg9 mutant strain EMS9-23 and the erg9-repaired strain SWE23-E9. The cultures were grown in YPD medium at 30° C. with shaking at 180 rpm. The EMS9-23 culture was also supplemented with 5 mg/L ergosterol. Growth was monitored by $OD_{600}$.

Figure 3:
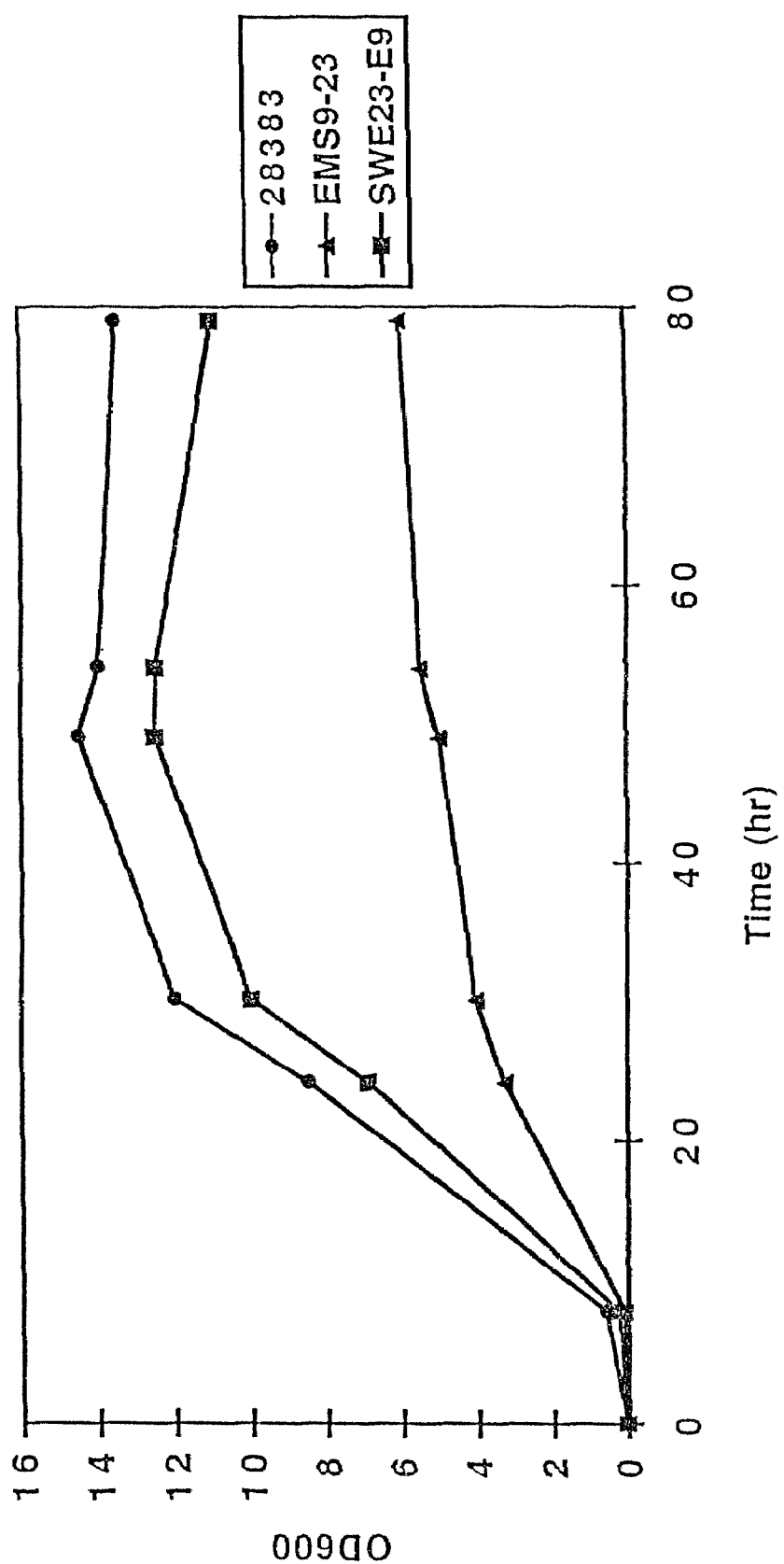
FIG. 3 illustrates the growth of wild-type, erg9 and repaired ERG9 strains.

The results of this experiment, presented in FIG. 3, show that the growth of the erg9 mutant was reduced, but that the growth of the wild-type parent strain 28383 and the erg9-repaired strain SWE23-E9 grew similarly. The slightly lower final $OD_{600}$ in the SWE23-E9 culture was probably due to the fact that this strain is a uracil auxotroph, and the concentration of uracil in the YPD medium was not optimal. These results indicate that the major cause of the growth defect in the erg9 mutants is the erg9 mutation itself. Other mutations in the erg9 mutants, such as the sue mutation(s), do not have a significant effect on growth.

H. One-Liter Fermentation

Strains MBNA1-13, EMS9-23/YEp352 and SWE23-ΔE91/YEp352 were grown in one-liter fermentors under fed-batch conditions as described below. Under these conditions, farnesol production by these strains ranged from 5.5-6.0% of dry cell weight (data shown in Section G above) in 191-239 hours.

Fermentation Conditions and Materials

The one-liter fermentation was performed by first autoclaving for 45 minutes at 121° C., in the fermenter, the following solution:

| | |
|---|---|
| $(NH_4)_2SO_4$ | 10.0 g/L |
| $KH_2PO_4$ | 10.0 g/L |
| $CaCl_2—2H_2O$ | 0.5 g/L |
| NaCl | 0.5 g/L |
| $MgSO_4—7H_2O$ | 3.0 g/L |
| yeast extract (Difco) | 2.0 g/L |
| salt solution | 20.0 mL |
| defoamer (Dow 1520) | 4.0 drops |
| deionized water | 500 mL. |

After autoclaving, the following sterile solutions were added:

| | |
|---|---|
| glucose solution (50%) w/v | 5.0 mL |
| vitamin solution | 15.0 mL |
| ergosterol solution | 0.2 mL. |

The glucose and vitamin solutions were sterilized by passage through a 0.45 micron filter.

The ergosterol solution is considered sterile (see below).

Glucose feed solution (made up in deionized water)

| | |
|---|---|
| glucose solution (60% w/v) | 360 mL |
| yeast extract solution (12.5% w/v) | 80 mL |
| ergosterol solution | 5.8 mL |

Glucose, yeast extract sterilized by autoclaving; ergosterol considered sterile.

Inoculum
1 mL cell suspension frozen in 10% glycerol inoculated into 250 mL YPDE medium in 1000 mL baffled flask, incubated 48 hours at 29° C. and 150 rpm; used 30 mL inoculum per fermenter.

Fermentation Conditions
28° C.
pH 4.5
Agitation 300-1000 rpm, aeration 50-200 mL/min as required to maintain dissolved oxygen at 10-60% of air saturation. Glucose feed solution added after initial glucose was depleted. Addition rate to achieve a growth rate of 0.04 $hr^{-1}$ considering that cell yield on glucose is 0.25. Maximum feed rate=3.5 ml/hr.

Salt Solution (Given Per Liter in Deionized Water)

| | |
|---|---|
| $FeSO_4$—$7H_2O$ | 0.28 g |
| $ZnSO_4$—$7H_2O$ | 0.29 g |
| $CuSO_4$—$5H_2O$ | 0.08 g |
| $Na_2MoO_4$—$2H_2O$ | 0.24 g |
| $CoCl_2$—$6H_2O$ | 0.24 g |
| $MnSO_4$—$H_2O$ | 0.17 g |
| HCl | 0.10 mL |

Vitamin Solution (Given Per Liter in Deionized Water)

| | |
|---|---|
| biotin | 10 mg |
| Ca-pantothenate | 120 mg |
| inositol | 600 mg |
| pyridoxine-HCl | 120 mg |
| thiamine-HCl | 120 mg |

Ergosterol Solution

| | |
|---|---|
| ethanol | 20 mL |
| IGEPAL | 20 mL |
| ergosterol | 0.4 g |

Heat at 50° C. with mixing until dissolved, store at −20° C.

IGEPAL is 1,3,3 tetramethyl butyl phenoxy(ethoxy)$_8$ ethanol (Sigma Chemical Company, St. Louis, Mo., Product IGEPAL CA-630, Cat. # 13021).

Example 2

This example describes the production of erg9 mutants by chemical mutagenesis of *S. cerevisiae* strain 64031 using ethylmethane sulfonate (EMS). Strain 64031 (obtained from ATCC) is an erg9-1 mutant that produces low levels of farnesol (see Example 1), and additional mutagenesis produced mutants exhibiting improved yields of farnesol.

A kill curve was performed using EMS, and a mutagenesis of 64031 was performed as described in Example 1. Selection was also performed as described in Example 1.

A total of 163 strains were found to be nystatin-resistant, ts, sterol auxotrophs. They were cultured in tubes and shake flasks, and farnesol production was determined as described in Example 1. The amounts of farnesol produced in the shake flask cultures are presented in Table 9.

TABLE 9

| | Farnesol (mg/ml) | | Farnesol (% dry weight) | |
|---|---|---|---|---|
| Strain | Cell | Medium | Cell extracts | Medium extracts |
| MBEMS8-1 | 0.038 | 0.019 | 1.7 | 0.8 |
| MBEMS8-2 | 0.048 | 0.008 | 3.6 | 0.6 |
| MBEMS8-5 | 0.013 | 0.022 | 0.5 | 1.0 |
| MBEMS8-6 | 0.045 | 0.016 | 5.6 | 2.0 |
| MBEMS8-11 | 0.024 | 0.003 | 2.0 | 0.2 |
| MBEMS8-12 | 0.043 | 0.006 | 6.9 | 1.0 |
| MBEMS8-16 | 0.026 | 0.001 | 3.5 | 0.2 |
| MBEMS8-18 | 0.040 | 0.009 | 1.4 | 0.3 |
| MBEMS8-19 | 0.023 | 0.003 | 2.8 | 0.4 |
| MBEMS8-21 | 0.021 | 0.009 | 1.5 | 0.7 |
| MBEMS8-23 | 0.025 | 0.008 | 2.9 | 0.9 |
| MBEMS8-25 | 0.018 | 0.007 | 1.3 | 0.5 |
| MBEMS8-26 | 0.028 | 0.011 | 3.7 | 1.5 |
| MBEMS8-27 | 0.035 | 0.010 | 5.5 | 1.5 |
| MBEMS8-31 | 0.020 | 0.011 | 1.1 | 0.6 |
| MBEMS8-32 | 0.016 | 0.009 | 0.5 | 0.3 |
| MBEMS8-33 | 0.000 | 0.000 | 0 | 0 |
| MBEMS8-34 | 0.000 | 0.000 | 0 | 0 |
| MBEMS8-35 | 0.000 | 0.000 | 0 | 0 |
| ATCC64031 | 0.018 | 0.005 | 0.9 | 0.3 |
| ATCC28383 | 0.000 | 0.000 | 0 | 0 |

Example 3

In Example 1.G. above, the creation of an erg9Δ::HIS3 mutant of MBNA1-13 was described. In this example, the construction of other haploid *S. cerevisiae* strains (not derived from MBNA1-13) containing an erg9 deletion::HIS3 insertion allele is described.

The ERG9 gene was PCR amplified using genomic DNA isolated from strain S288C (according to the method of Sherman et al.) as template and the following two primers:

(SEQ ID NO:5)
5'oligo = gag cat CCA CGG GCT ATA TAAA; 250 BamUp (SEQ ID NO:6)
3'oligo = tcc ccc cg GGC GCA GAC TTC ACG CTC; 1712 XmaLo The PCR amplified ERG9 DNA was digested with BamHI and XmaI, then ligated to BamHI, XmaI digested pRS316 (Yeast/*E. coli* shuttle vector, Sikorski and Hieter, 1989).

The PCR conditions were:

| | | |
|---|---|---|
| 94° C. for 1 min. - | | 1 cycle |
| 94° C. for 30 sec. | } | |
| 58° C. for 1 min | | 30 cycles |
| 72° C. for 1 min. | | |
| 72° C. for 2 min. - | | 1 cycle |

The ERG9 gene cloned in this manner extends from position #11555 to position #13047 of GenBank Accession #U00030, and the resulting clone was named pJMB98-12. The construction of the deletion in ERG9 and the insertion of HIS3 DNA was done as follows:

The HIS3 gene was obtained by digesting the HIS3 containing plasmid pRS403 (Stratagene, LaJolla, Calif.) with Eco47III and SspI, and purifying the 1226 bp fragment containing the HIS3 gene.

The plasmid pJMB98-12 was digested with Van91I, then treated with T4 DNA polymerase to make it blunt-ended. The plasmid was further digested with HpaI so that an internal 589 bp fragment within ERG9 was deleted. Into this site was ligated the 1226 bp Eco47III, SspI fragment containing the HIS3 gene. The resulting plasmid, pKML19-41, has the HIS3 gene cloned within the deleted ERG9 gene, with the HIS3 coding sequence in the same orientation as the ERG9 coding sequence.

To transform yeast with this erg9Δ::HIS3 DNA, the plasmid pKML19-41 was digested with SmaI and XhaI, and the 2141 bp fragment containing the erg9Δ::HIS3 gene was isolated. DNA was purified from agarose gel slices by using GeneClean.

Approximately 5 μg of purified erg9Δ::HIS3 DNA was used to transform diploid strain CJ3A X CJ3B (a/α, ura3/ura3, his3/his3, leu2/leu2, trp1/trp1, upc2/upc2, obtained from Dr. L. Parks, N.C. State University, Raleigh, N.C.) using the lithium acetate transformation procedure described in Gietz, et al. (1995). CJ3A X CJ3B is homozygous for the upc2 mutation. This mutation allows sterol uptake under aerobic conditions (Lewis, et al., 1988). It was believed that the upc2 mutation would allow the easy production of a haploid strain carrying a mutation in the erg9 gene. The histidine auxotrophy was necessary to select for strains carrying the plasmids that contain the functional HIS3 gene.

The transformed cells were plated onto SCE medium (described in Example 1.F.) lacking histidine (SC-His) to select for HIS+ transformants.

Hundreds of transformants were obtained. These HIS+ cells were then patched onto SC-His and allowed to grow for two more days. The transformants were then patched onto sporulation medium (Sherman, et. al, 1986). Sporulation medium contains (per liter of distilled water): 1% potassium acetate, 0.1% Bacto yeast extract, 0.05% dextrose and 2% Bacto agar. The patches were then allowed to grow and sporulate for 3-5 days. A portion of the cells was removed and placed in a solution of lyticase to digest the ascus cell wall. The cells were then spread in a thin line onto a YPD+2 mg/L ergosterol (YPDE) plate. The sporulated diploid cells form tetrads containing four spores, and the individual spores were separated using a micromanipulator. These individual haploid spores will germinate with each containing a single copy of the chromosomes.

A 2:2 segregation was expected for erg9Δ::HIS3 knockouts in this strain. Two spores should be viable on YPD since they would contain the copy of the chromosome which was not disrupted (meaning they would not need ergosterol since they have a functioning ERG9 gene and would be able to grow on YPD because histidine is present in the medium). The other two spores should grow on SC-His+2 mg/L ergosterol (SCE-His) since, if the erg9Δ::HIS3 DNA integrated at the ERG9 site, the cells would require ergosterol, but would grow without histidine.

Tetrads from some of the pKML19-41 transformants were analyzed for phenotypic determination of the erg9 knockout. The results showed that only two of the four spores were viable when grown aerobically. When these were replica-plated to YPD these two spores survived, but they did not survive on SC-His or SCE-His. This indicated a 2:2 segregation and that the two surviving spores were of the parental type or auxotrophic for histidine. This indicated that the two that did not survive aerobically probably contained the erg9: HIS3 knockout.

PCR analysis confirmed the results of an erg9Δ::HIS3 knockout in several of the strains. Total DNA was isolated using a rapid DNA isolation method from several of the diploid transformants that showed the 2:2 segregation. The total DNA was then used as template for PCR amplification with primers complementing sequence 5' and 3' to the ERG9 gene in the chromosome.

The oligonucleotides used for this analysis were as follows:

```
5'-oligo = 250 Bam Up (described above)

(SEQ ID NO:7)
3'-oligo = 3ERG9-1 = gat ccg cg GCT CAA GCT AGC
GGT ATT ATG CC
```

3ERG9-1 contains sequences corresponding to the reverse complement of sequences from position #14812 to position #14790 of the GenBank Accession #U00030 sequence.

Oligonucleotide 250 Bam Up lies within the sequence of the ERG9 clone used to construct the erg9Δ::HIS3 allele, whereas oligonucleotide 3ERG9-1 lies downstream of the boundary of the cloned ERG9 DNA. ERG9 sequences amplified from genomic DNA by these two primers must represent ERG9 genes located at the actual chromosomal ERG9 locus, and will not amplify erg9Δ::HIS3 sequences that integrated at other chromosomal locations.

The results showed two bands at 3.271 and 3.908 kb, indicating the presence in the diploid strains of one functional copy of the ERG9 gene and one interrupted copy that is kb 637 bp larger due to the HIS3 gene insertion.

Southern blot analysis also was performed to verify the erg9Δ::HIS3 interruption in the diploids. Genomic DNA from a parental diploid strain carrying two normal copies of ERG9 gene was compared to three different transformants believed to carry one normal ERG9 gene and one disrupted ERG9 gene. The DNA was digested with either Acc I or Xba I, separated by gel electrophoresis, transferred to an Immobilon S membrane, and probed with specific probes to examine the ERG9 genes present. The probe in this case was a 1.4 kb fragment containing a portion of the ERG9 gene.

The probe used for Southern blot analysis of genomic DNA was prepared from the PCR amplified ERG9 gene using oligonucleotides 250 Bam Up and 1712 Xma Lo (described above). Plasmid pJMB98-12 was used as template.

PCR Conditions were:

| | |
|---|---|
| 94° C. for 1 min. - | 1 cycle |
| 94° C. for 30 sec. | |
| 58° C. for 1 min | 30 cycles |
| 72° C. for 1 min. | |
| 72° C. for 2 min. - | 1 cycle |

The amplified ERG9 DNA was purified and biotinylated, as described above. Approximately 1 µg of biotinylated probe was used to hybridize to the blot.

Hybridization of the probe to the specific DNA bands under stringent conditions identified complementary sequence being present. For the parental diploid, CJ3AxCJ3B, a single band was seen at 2.1 kb for the Acc I digest and a single band at 2.8 kb was seen with the Xba I digest. The putative erg9Δ::HIS3 knockouts each contained two bands: bands at 2.1 kb and 1.3 kb for the Acc I digest; and bands at 2.8 kb and 3.4 kb for the Xba I digest. These results indicated the presence of one copy of the wild-type ERG9 gene along with an erg9Δ::HIS3 disruption in the transformed diploids.

Attempts were then made to grow the haploid cells anaerobically on YPDE agar. Strains that are blocked in the ergosterol pathway can take up sterols under anaerobic conditions. Two of the spores grew rapidly under anaerobic conditions (ERG9, his−) and two grew very slowly (erg9Δ::HIS3). The spores of three of the strains erg9Δ::HIS3 (KML505, KML510, and KML521) that grew anaerobically on plates were grown in liquid medium under anaerobic conditions and showed farnesol production. Upon further incubation of the original YPDE plates aerobically, it appeared that a few of the haploid strains that tested positive for farnesol production under anaerobic growth were growing. Three such viable spores (derived from KML505) arose after prolonged aerobic incubation. These aerobically-growing strains, designated as BKY1-2D, BKY1-7C, and BKY1-8D, all produced farnesol under aerobic conditions.

The parent strain KML510 (a/α, ura3/ura3, his3/his3, trp1/trp1, leu2/leu2, upc2/upc2, ERG9/erg9Δ::HIS3) containing either pJMB98-12 or pRS316 were sporulated and tetrads were dissected onto YPDE plates. The plates were incubated under aerobic conditions, and the following patterns of spore growth were observed.

Tetrad analysis of KML510/pJMB98-12 were done with 20 tetrads. 16 tetrads gave rise to two viable, fast-growing spores and two nonviable spores. All viable spores were his−, erg+. Three tetrads gave rise to two viable, fast-growing spores, one viable, slow-growing spore, and one non-viable spore. The viable, fast-growing were all his−, erg+. The viable, slow-growing spores were all his+, erg−. One tetrad did not give rise to any viable spores. All of the his+,erg− spores were also ura−, indicating that pJMB98-12 did not segregate into these spores during meiosis. One of the his+, erg+ spores was used for further studies, and was named BTY19-9C.

Tetrad analysis of KML510/pRS316 was done with 20 tetrads. 18 tetrads gave rise to two viable, fast-growing spores and two non-viable spores. Two tetrads gave rise to two viable, fast-growing spores, one viable, slow-growing spore, and one non-viable spore. All fast-growing spores were his−, erg+. All slow-growing spores were his+, erg−. All his+, erg− spores were also ura−, indicated that pRS316 did not segregate into these spores during meiosis. One of the his+, erg− spores was studied further, and was named BTY20-2A.

To confirm that BTY19-9C and BTY20-2A did not carry the wild-type ERG9 gene, a PCR experiment was conducted using genomic DNA isolated from the two strains, and the oligonucleotides VE104-5 and VE105-3.

5'oligo = VE104-5 = gac tct AGA AGC GGA AAA CGT ATA CAC

3'oligo = VE105-3 = described above

VE104-5 contains sequences corresponding to position #11631 to 116541 of GenBank Accession #U00030 sequence.

The predicted PCR product size for a functional ERG9 gene was 2.23 kb, and for the erg9Δ::HIS3 disruption, 2.87 kb. Strains BTY19-9C and BTY20-2A had a PCR product of approximately 2.87 kb, which indicated the presence of the erg9Δ::HIS3 disruption.

Five strains (BKY1-2D, BKY1-7C, BKY1-8D, BTY19-9C and BTY20-2A) were evaluated for farnesol production in shake flasks. Strains BKY1-7C and BTY20-2A gave the best production of farnesol of the five strains, but BKY1-7C grew very slowly.

Transformants KML505, KML510, and KML521 were transferred to sporulation medium. Tetrads were dissected onto YPDE and allowed to grow for extended periods of time under aerobic conditions to look for growth of additional spores beyond the anticipated 2:2 segregation (viable:nonviable). Two additional spores were viable after further incubation under aerobic conditions. These two strains, BJY7-5D and BJY8-1A, produced farnesol in a tube screen.

Strains BJY7-5D and BJY8-1A were evaluated in shake flasks. BJY8-1A gave the best farnesol production (0.29 mg/ml, 4.7% based on cell dry weight) after 72 hours incubation. BJY7-5D gave 0.18 mg farnesol/ml, (3.5% based on cell dryweight).

Example 4

This example shows the overexpression of HMG CoA reductase in strains with and without a functional ERG9 gene.

HMG CoA reductase has been proposed to be the key enzyme regulating the flow of carbon through the isoprenoid pathway. In *S. cerevisiae*, two genes, HMG1 and HMG2, code for the two isozymes of HMG CoA reductase, designated HMG1p and HMG2p. Regulation of HMG CoA reductase is achieved through a combination of transcriptional and translational regulation as well as protein degradation. The segments of the HMG1 and HMG2 genes that encode the catalytic domains of the HMG1p and HMG2p isozymes have been cloned under transcriptional control of the strong promoter from the GPD (glyceraldehyde-3-phosphate dehydrogenase) gene. The plasmids containing these constructions (pRH127-3 and pRH124-31, containing the catalytic domains of HMG1p and HMG2p, respectively) were obtained from R. Hampton, U.C. San Diego. Strains of *S. cerevisiae* overexpressing the catalytic domain of HMG1p were reported to have an elevated flow of carbon through the isoprenoid pathway. This increased carbon flow was manifested as squalene and ergosterol overproduction (Donald, K. A. G., Hampton, R. Y., and Fritz, I. B., 1997, Effects of Overproduction of the Catalytic Domain of 3-Hydroxy-3-Methylglutaryl Coenzyme A Reductase on Squalene Synthesis in *Saccharomyces cerevisiae*. Applied and Environmental Microbiology 63:3341-3344).

A. HMG CoA Reductase Overexpression in Strains with a Functional ERG9 Gene

In order to confirm that overexpressing HMG CoA reductase would result in increased carbon flow through the isoprenoid pathway in the strains derived from ATCC 28383, similar to other strains of *S. cerevisiae* (Donald, et. al., 1997), the strain SWY5, a ura3 mutant of the parental strain ATCC 28383, and SWE23-E9, the erg9 repaired version of EMS9-23 (strains described in Example 1.G. above), were transformed with plasmids pRH127-3 and pRH124-31. Transformations were performed using the LiOAc procedure (Gietz, et. al., 1995). Control strains carrying the empty vector YEp352 were also constructed. Representative transformants were tested for squalene and ergosterol production in a shake flask experiment. Cells were grown in 50 ml SCE-ura medium at 30° C., with shaking at 180 rpm for 48 hours. At 24 hours, 10 ml of the culture was withdrawn, and the cells harvested for HMGCoA reductase assays as described in Example I.D. At the end of the 48-hour growth period, an aliquot of the cultures was used to inoculate flasks containing 50 ml YPD medium such that the starting $OD_{600}$ of the cultures was 0.1. The cultures in YPD medium were grown for 72 hours at 30° C., with shaking at 180 rpm, and then analyzed for dry cell weight, squalene and ergosterol production. The extraction method used for this analysis was as follows. Ten ml of the culture was pelleted by centrifugation at 1,500×g for 10 minutes. The cell pellet was resuspended in 1 ml of deionized water, and the cells were repelleted. Cell pellets were resuspended in 1 ml of deionized water and disrupted by agitation with zirconium silicate beads (0.5 mm diameter). The broken cell suspension was saponified with 2.5 ml of a 0.2% solution of pyrogallol (in methanol) and 1.25 ml of 60% potassium hydroxide solution at 75 degrees C. for 1.5 hours. The samples were then extracted with 5 ml of hexane, vortexed for 3 minutes and centrifuged at 1,000×g for 20 minutes to separate the phases. The hexane layer was then analyzed by GC-MS as described in Example 1.B.

The data from this experiment are shown in Table 10. Compared to the control strains carrying only the Yep352 vector, the strains that overexpress the catalytic domains of either HMG1p or HMG2p contained high levels of HMGCoA reductase activity and elevated levels of squalene. However, neither of the strains overexpressing HMG1p or HMG2p contained significantly increased levels of ergosterol. Nevertheless, these data show that increasing the activity of HMG CoA reductase in the MBNA1-13 strain lineage increases the carbon flow through the isoprenoid pathway.

B. HMG CoA Reductase Overexpression in an erg9 Mutant

Having shown that amplification of HMG1p or HMG2p increased carbon flow to squalene, whether overexpression of HMG1 or HMG2 would increase farnesol production in a strain carrying the erg9 mutation was tested. Strain SWE23-ΔE91 (described in Example 1.G.) was transformed with plasmids pRH127-3 or pRH124-31. Transformation of SWE23-ΔE91 was accomplished using the LiOAc transformation procedure (Gietz et al, 1996). Approximately 2.5 μg of pRH127-3 or pRH124-31 DNA were used in each transformation. Transformants were selected on SCE-ura plates, and several were chosen and restreaked for purification on SCE-ura plates. To test the effect of amplified HMG CoA reductase on farnesol production, representative transformants were grown for 48 hours in liquid SCE-ura medium. A control strain, SWE23-ΔE91/YEp352, was also included in the experiment. At the end of the 48 hours growth period, aliquots of the cultures were used to inoculate flasks containing 50 ml of YPDE medium such that the initial $OD_{600}$ was 0.5. These cultures were grown for 72 hours at 30° C., with shaking at 180 rpm. At the end of the incubation period, samples were analyzed for dry cell weight and farnesol concentration. To confirm that the HMG CoA reductase genes were being overexpressed in the transformants, 20 ml of the cultures grown in SCE-ura were harvested by centrifugation at 1500×g for 10 minutes, and HMG CoA reductase activity measured using the permeabilized cell method described in Example I.D. The data from this experiment are shown in Table 11.

TABLE 11

Effect of Elevated HMG CoA Reductase Activity on Farnesol Production in an erg9:.-HIS3 Mutant Grown in Shake Flask Cultures.

| Strain/plasmid | Dry Cell Weight (g/L) | Farnesol | | HMG CoA Reductase Activity (nmol/min/mg) |
|---|---|---|---|---|
| SWE23-ΔE91/ YEp352 | 3.31 | 222 | 6.7 | 7.5 |
| SWE23-ΔE91/ pRHI27-3 | 3.87 | 104 | 2.7 | 47.0 |
| SWE23-ΔE91/ pRH124-31 | 3.48 | 104 | 3.0 | 36.0 |

In both SWE23-ΔE91/pRH127-3 and SWE23-ΔE91/pRH124-31, the levels of HMG CoA reductase activity were elevated. However, the farnesol production in these strains

TABLE 10

Effect of Amplified HMGCoA Reductase Activity on Squalene and Ergosterol Production in Strains Having a Normal Isoprenoid Pathway

| Strain/plasmid | Dry Cell Weight (g/L) | Squalene | | Ergosterol | | HMG CoA Reductase Activity (nmol/min/mg) |
|---|---|---|---|---|---|---|
| | | μg/ml | % dry wt. | μg/ml | % dry wt. | |
| SWY5/YEp352 | 7.68 | 0.18 | 0.003 | 2.9 | 0.038 | 2.4 |
| SWY5/pRH127-3 | 6.82 | 3.50 | 0.051 | 5.2 | 0.076 | 52 |
| SWY5/pRH124-31 | 7.49 | 4.15 | 0.055 | 2.9 | 0.039 | 27 |
| SWE23-E9/YEp352 | 6.96 | 0.33 | 0.005 | 5.5 | 0.079 | 2.7 |
| SWE23-E9/pRH127-3 | 6.89 | 6.78 | 0.099 | 8.3 | 0.121 | 55 |
| SWE23-E9/pRH124-31 | 6.90 | 4.90 | 0.071 | 6.1 | 0.088 | 29 | was lower than the control strain SWE23-ΔE91/YEp352. This unexpected result was observed several times in independent experiments.

Figure 4:
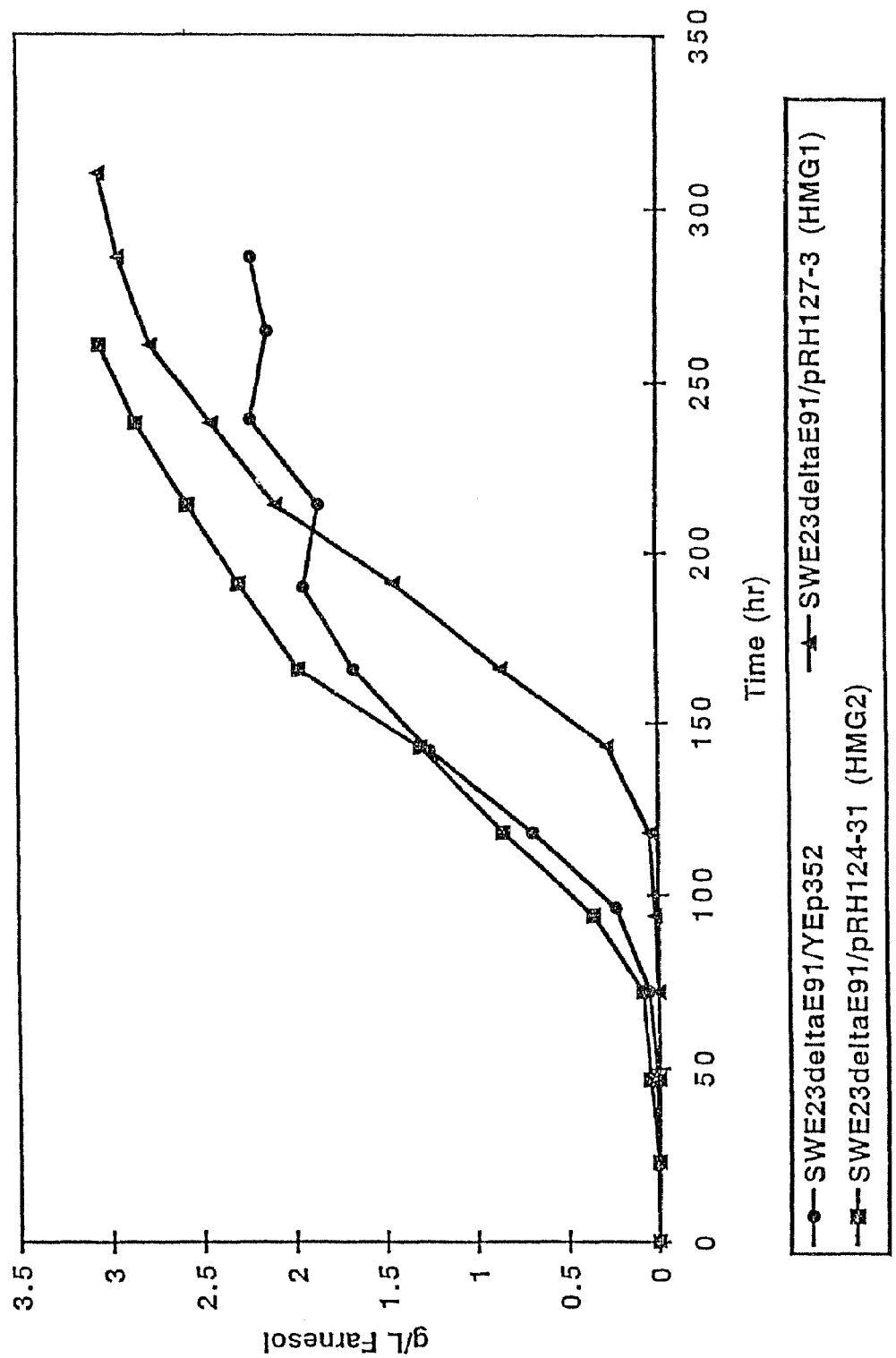
FIG. 4 illustrates the production of farnesol in microorganisms with amplified production of HMG CoA reductase.

Despite the failure of amplified HMG CoA reductase activity to increase farnesol production in an erg9Δ::HIS3 strain grown in shake flask cultures, the strains listed in Table 12 were tested for farnesol production in 1-L fermentors using the protocol described in Example 1.H. Under these conditions, the expected result was observed; the strains overexpressing HMG CoA reductase produced significantly more farnesol than the control strain. The data are summarized in FIG. 4 and Table 12. The elevation of HMG CoA reductase activity in strains SWE23-ΔE91/pRH127-3 and SWE23-ΔE91/pRH124-31 was confirmed by direct enzyme assay using the permeabilized cell method. This is illustrated by the reductase activities at specific time points during the fermentation (shown in Table 12).

TABLE 12

Effect of Elevated HMG CoA Reductase Activity on Farnesol Production in an erg9Δ::HIS3 Mutant Grown in 1-L Fermentors.

| Strain/plasmid | Time (hr.) | Dry Cell Weight (g/L) | Farnesol g/L | % dry cell weight | HMG CoA Reductase Activity (nmol/min/mg) |
|---|---|---|---|---|---|
| SWE23-ΔE91/YEp352 | 239 | 37.2 | 2.23 | 6.0 | 4.1 |
| SWE23-ΔE91/pRHI27-3 | 310 | 35.0 | 3.06 | 8.7 | 20 |
| SWE23-ΔE91/pRH124-31 | 261 | 31.7 | 3.05 | 9.6 | 14 |

Example 5

This example describes the overexpression of various GGPP synthases in erg9 mutants.

In order to convert FPP produced in erg9 mutant strains to GGPP (the precursor of desired product, GG), the genes coding for various GGPP synthases in erg9 mutants were overexpressed. The genes cloned for this purpose were the BTS1 gene from *Saccharomyces cerevisiae*, the crtE gene from *Erwinia uredovora*, the al-3 gene from *Neurospora crassa*, and the ggs gene from *Gibberella fujikuroi*. Plasmids carrying these genes were constructed as follows.

To clone the BTSII gene, genomic DNA was prepared from *S. cerevisiae* strain S288C according to the method described in Sherman, et. al. (1986). The gene was amplified by PCR using the following two oligonucleotides.

```
                                            (SEQ ID NO:8)
5'oligo = VE100-5  gactctAGAGTTTACGAGTCTGGAAAATC (SEQ ID NO:9)
3'oligo = VE101-3  gtaggATCCATGGAATTGAGCAATAGAG
```

The PCR conditions were: 94° C., 3 minutes; 94° C., 1 minute; 52° C., 1 minute; 74° C., 1.5 minutes; 30 cycles; then 74° C., 7 minutes (1 cycle). The PCR product was digested with XbaI and BamHI and ligated into XbaI, BamHI digested pPGK315 to generate pTWM101. The plasmid pPGK315 contains the *S. cerevisiae* PGK promoter and terminator separated by a multiple cloning site. Cloning the BTS1 gene into pPGK315 as described above placed the BTS1 gene under control of the strong PGK promoter. Plasmid pPGK315 was constructed by digesting plasmid pRS315 with SacI and SmaI, then treating with T4 DNA polymerase to create blunt ends. The plasmid was religated to generate pRS315-DSS. Plasmid pRS315DSS was then digested with XhoI and ligated with a 994 bp SalI, XhoI fragment obtained from plasmid pPGKMCS that contained the PGK promoter and terminator separated by a multiple cloning site. Plasmid pPGKMCS was constructed by digesting pPGK (Kang et. al., 1990, Mol. Cell. Biol., 10:2582) with EcoRI and BamHI, then ligating with the following two annealed oligonucleotides.

```
                                            (SEQ ID NO:10)
5'oligo = AATTCCAAGCTTGCGGCCGCTCTAGAACGCGTG (SEQ ID NO:11)
3'oligo = GATCCACGCGTTCTAGAGCGGCCGCAAGCTTG
```

Plasmid pTWM110-11 was constructed by ligating a 2397 bp KpnI-SalI fragment containing the PGK promoter/BTS1/PGK terminator (obtained by digestion of PTWM110 with KpnI and SalI) into KpnI-SalI-digested YEp352.

To clone the crtE gene, genomic DNA was isolated from *E. uredovora* strain 2OD3 using the PureGene genomic DNA Isolation Kit (Gentra Systems, Inc., Minneapolis, Minn.) The crtE gene was amplified using the genomic DNA and the following two oligonucleotides.

```
                                            (SEQ ID NO:12)
5'oligo = 20D3Up   gaattcGTTTATAAGGACAGCCCGA (SEQ ID NO:13)
3'oligo = 20D3Lo   ctgcagTCCTTAACTGACGGCAGCGA
```

Oligo 2OD3Up contains sequences corresponding to position #206 to #224 of the Genbank Accession #D90087 sequence. Oligo 20D3Lo contains the reverse complement of sequences from position #1117 to #1136 of the same Genbank sequence file. The amplified DNA was ligated into the SrfI site of pCR-Script SK(+) (Stratagene, La Jolla, Calif.) to generate plasmid pSW1-B. This plasmid was then digested with EcoRI and SacI, and the 973 bp fragment containing the crtE gene was purified and ligated into EcoRI-SacI digested pAD314-956 to generate plasmid pSW2B. Plasmid pSW2-B was digested with BamHI to generate a 2199 bp fragment containing the ADH1 promoter, crtE coding sequence, and ADH1 terminator, and this fragment was ligated into BamH digested YEp352 to generate pSW4A, which placed the crtE gene in the orientation opposite to that of the URA3 gene in the plasmid, and pSW4B, which placed the crtE gene in the same orientation as the URA3 gene.

Plasmid pADH313-956 was generated in the following manner. Plasmid pRS313 (Sikorski and Hieter, 1989) was digested with SacI and XhaI, treated with T4 DNA polymerase to create blunt ends, then relegated to generate plasmid pDSX313. This plasmid was digested with SmaI and ApaI, treated with T4 DNA polymerase to create blunt ends, and then relegated to generate pDSXSA313. Plasmid pAAH5 (Ammerer, G., 1983, Meth. Enzymol. 11: 192-201), which carries the ADH1 promoter and terminator separated by a HindIII site, was digested with HindIII, then ligated to the following two annealed oligonucleotides to introduce a multiple cloning site and create pAAH5-MCS.

```
                                        (SEQ ID NO:14)
5'oligo = MCS1    AGCTGAATTCGAGCTCGGTACCCGGGCTCTAGAG
                  TCGACCTGCAGGCATGCA (SEQ ID NO:15)
3'oligo = MCS2    AGCTTGCATGCCTCCAGGTCGACTCTAGAGCCCG
                  GGTACCGAGCTCGAATTC
```

A PCR reaction containing pADH313-MCS as template and the following two oligonucleotides was performed, and a 1232 bp PCR product containing the ADH1 promoter, multiple cloning site, and ADH1 terminator was obtained.

```
                                        (SEQ ID NO:16)
5'oligo = ADH1A   gacggatCCGTGGAATATTTCGGATATCC (SEQ ID NO:17)
3'oligo = ADH1B   ctcggatccGGACGGATTACAACAGGTATTGTCC
```

Oligo ADH1A contains sequences corresponding to position #16 to #37 of the Genbank Accession #V01292 sequence. Oligo ADH1B contains the reverse complement of sequences from position #2092 to #2116 of the same Genbank sequence file. The 1232 bp PCR product was digested with BamHI and ligated into BamHI digested pDSXSA313 to generate plasmid pADH313-956.

To clone the *N. crassa* al-3 gene, genomic DNA was isolated from *N. crassa* strain ATCC 14692 using the method described by Borges et al. in the methods section of the Fungal Genetics Stock Center's web site (www.kumc.edu/research/fgsc/fgn37/borges.html). The gene was amplified by PCR using the following two oligonucleotides.

```
5' oligo = VE118-5
cagaatTCACCATGGCCGTGACTTCCTCCTC         (SEQ ID NO:18)

3' oligo = VE119-3
caagatctCATACATTCAATCCTCATGGACAC        (SEQ ID NO:19)
```

Oligo VE118-5 contains sequences corresponding to position # 1216 to # 1240 of the Genbank Accession #U20940 sequence. Oligo VE119-3 contains the reverse complement of sequences from position #2576 to #2599 of the same Genbank sequence file. The amplified DNA was ligated into the SrfI site of pCR-Script SK(+) (Stratagene, La Jolla, Calif.) to generate pSW7-1 and pSW7-2, two independent PCR clones of the al-3 gene. These two plasmids were then digested with EcoRI and BglII, and the 1393 bp fragment containing the al-3 gene was purified and ligated into EcoRI, BamHI digested pPGK (Kang et. al., 1990) to generate pSW9-1 and pSW9-2, with the al-3 sequence in each derived from pSW7-1 and pSW7-2, respectively.

To clone the ggs gene, genomic DNA was prepared from *Gibberella fujikuoi* strain ATCC 12617, using the same procedure described above for *Neurospora*. The ggs gene was amplified by PCR using the following two oligonucleotides.

```
5' oligo = VE120-5
gagaattCTTAACACGCATGATCCCCACGGC         (SEQ ID NO:20)

3' oligo = VE121-3
ctggatcCGTCAAATCCGTGAATCGTAACGAG        (SEQ ID NO:21)
```

Oligo VE120-5 contains sequences corresponding to position #607 to #630 of the Genbank Accession #X96943 sequence. Oligo VE121-3 contains the reverse complement of sequences from position #1908 to #1932 of the same Genbank sequence file. The amplified DNA was ligated into the SrfI site of pCR-Script SK(+) to generate pSW8-1 and pSW8-2, two independent PCR clones of the ggs gene. These two plasmids were then digested with EcoRI and BamHI, and the 1335 bp fragment containing the ggs gene was purified and ligated into EcoRI, BamHI digested pPGK to generate pSW10-1 and pSW10-2, with the ggs sequence in each derived from pSW8-1 and pSW8-2, respectively.

Strain EMS9-23 (ura3, erg9, described in Example 1.G.) was transformed with the plasmids described above using the LiOAc method, and transformants were selected on SCE-ura plates. Transformants were picked and restreaked on SCE-ura plates for purification. Representative transformants were tested for GG production. The strains were grown at 30° C. for 48 hours in liquid SCE-ura medium, then used to inoculate flasks containing YPDE medium, such that the initial $OD_{600}$ was 0.5. These cultures were incubated at 30° C. with shaking for 72 hours and analyzed for dry cell weight, farnesol and GG levels. A second set of flasks containing 20 ml of SCE-ura medium was also inoculated from the same starting cultures and was grown for 48 hours. The cells from these flasks were harvested, washed with 10 ml 50 mM BisTris-Propane buffer, pH 7.0, and repelleted. The cell pellets were then used to prepare permeabilized cell suspensions for GGPP synthase assays. The cells were permeabilized by resuspending in 1 ml of 50 mM Bis-Tris-Propane buffer, pH 7.0, containing 0.1% Triton X100, and frozen at 80° C. until needed. After thawing, the permeabilized cells were used for GGPP synthase assays. The GGPP synthase assay mixture contained 0.05M Bis-Tris propane buffer, pH 7.0 (X μl), 0.1M dithiothreitol (1 μl), 1 mg/ml FPP (5 μl), 1 mg/ml IPP (5 μl) and permeabilized cells (Y μl), where X+Y=87 μl. A control reaction was included in which the FPP and IPP were omitted. The assay mixtures were incubated at 37° C. for 20 minutes. 0.1 ml of 2× glycine buffer (0.2M glycine, 2 mM $MgCl_2$, 2 mM $ZnCl_2$, pH 10.4) and 63 units of alkaline phosphatase (Sigma Chemical Co., St. Louis, Mo.) were added, and the mixtures were incubated for 60 minutes at 37° C. The mixtures were then extracted with 0.2 ml 1:1 hexane:ethyl acetate, and analyzed for GG by GC/MS. GGPP synthase activity is expressed as nmol GGPP formed/min/mg protein.

The dry cell weights, farnesol production, GG production and GGPP synthase activities for the strains are summarized in Table 13. The control strain, EMS9-23/YEp352, which lacks a cloned GGPP synthase, made 8.7% farnesol (based on dry cell weight) and essentially no GG. The four other strains, each of which overexpressed a different cloned GGPP synthase, produced approximately the same amount of farnesol as the control (8.0-9.74%) and produced levels of GG ranging from 0.62-1.73%.

TABLE 13

GG Production in Shake Flask Cultures of Strains Overexpressing Four Different Cloned GGPP Synthase Genes.

| Strain | Cloned GGPP synthase gene | Dry cell weight (g/L) | FOH (% of dry cell weight) | GC (% of dry cell weight) | GGPP synthase activity (nmol/min/mg) |
|---|---|---|---|---|---|
| EMS9-23/YEp352 | — | 3.38 | 8.7 | 0.01 | ND |
| EMS9-23/pTWM110-11 | BTS1 | 3.12 | 8.98 | 1.73 | 0.065 |
| EMS9-23/pSW4B | crtE | 2.02 | 9.74 | 1.68 | 0.094 |
| EMS9-23/pSW9-1 | al3 | 3.38 | 8.0 | 0.62 | 0.032 |
| EMS9-23/pSW10-2 | ggs | 3.16 | 9.3 | 1.0 | 0.03 |

The effect of amplification of GGPP synthase activity on GG production was further evaluated in I-L fermentors. Strain EMS9-23 was transformed with plasmid pTWMI10-11, carrying the cloned *S. cerevisiae* BTS1 gene. Strain SWE23-ΔE91 (described in Example 1.G. above) was transformed with either Yep352 (vector control) or pSW4A-3 (an individual isolate of plasmid pSW4A, carrying the cloned crtE gene). Strains SWE23-ΔE91/YEp352, EMS9-23/pTWM110-11 and SWE23-ΔE91/pSW4A-3 were grown in 1-liter fermentors using the method described in Example 1.H., and growth, farnesol production and GG production were compared.

Figure 5:
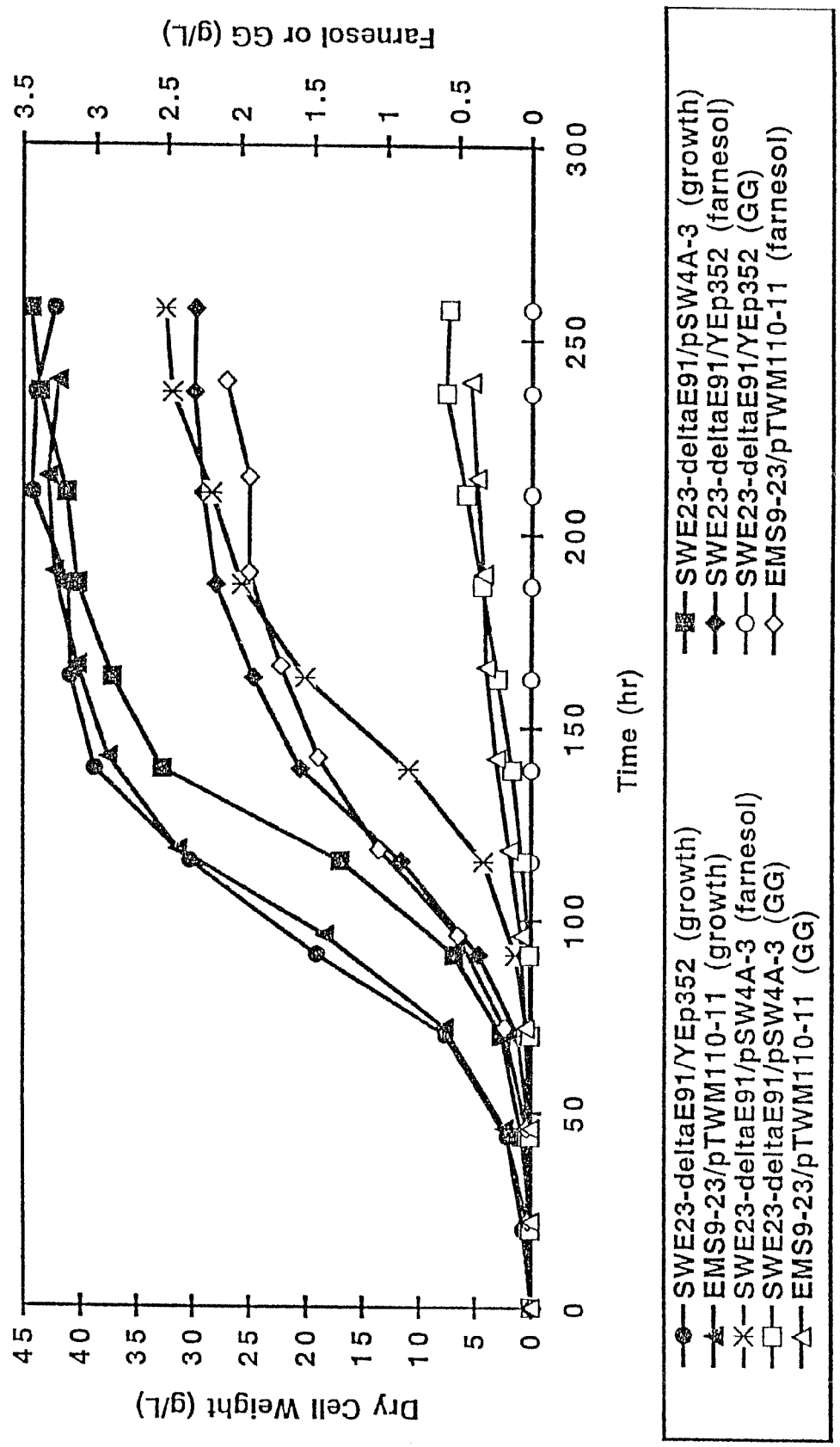
FIG. 5 illustrates the production of farnesol and GG in strains overexpressing GGPP synthases.

The results are shown in FIG. 5 and Table 14. The growth of the three strains was similar. Strain SWE23-ΔE91/YEp352 produced 2.32 g/L farnesol in 236 hours, and did not produce any detectable GG. EMS9-23/pTWM10-11 produced 2.1 g/L farnesol in 239 hours and also produced 0.42 g/L GG in the same time period. Strain SWE23-ΔE91/pSW4A-3 produced 2.47 g/L farnesol in 236 hours and also produced 0.59 g/L GG in the same period. The GGPP synthase activity in the control strain was below detectable limits. The production of GG by strains EMS9-23/pTWM110-11 and SWE23-ΔE91/pSW4A-3 correlated to increased GGPP synthase activity.

The ERG20 gene was amplified by PCR using genomic DNA from *S. cerevisiae* strain S288C (prepared according to the method described in Sherman et al., 1986). and the following two oligonucleotides.

```
5' oligo = BamFPPUp
ggccggatccATATTACGTAGAAATGGCTTCAG   (SEQ ID NO:22)

3' oligo = XhoFPPLo
gccgctcgagGGTCCTTATCTAGTTTG         (SEQ ID NO:23)
```

Oligo BamFPPUp contains sequences corresponding to position #790 to #810 of the Genbank Accession # J05091 sequence. Oligo XhoFPPLo contains the reverse complement of sequences from position #1891 to #1907 of the same Genbank sequence file. The PCR product was digested with BamHI and XhoI, and ligated into a vector containing the *S. cerevisiae* GPD (glyceraldehyde-3-phosphate dehydrogenase) promoter and PGK terminator. The promoter/terminator vector was obtained by digesting a plasmid containing the catalytic domain of the *S. cerevisiae* HMG2 gene cloned between the GPD promoter and PGK terminator, namely pRH124-31 (described in Example 4), with BamHI and SalI to remove the HMG2 DNA. The 6.3 kb band corresponding to the promoter/terminator vector was purified and ligated to the 1129 bp fragment containing ERG20 to generate pJMB1931 and pJMB19-32. Plasmids pJMB19-31 and pJMB19-32 were used to transform strain SWE23-ΔE91 (ura3, his3, erg9Δ:: HIS3) using the LiOAc method, and transformants were selected on SCE-ura plates. Transformants were picked and restreaked on SCE-ura plates for purification.

TABLE 14

Growth, Farnesol and GG Production in Strains Overexpressing GGPP Synthases and Grown in 1-L Fermentors

| Strain/Plasmid | Time (hr.) | Dry Cell Weight (g/L) | Farnesol g/L | Farnesol % Dry Cell Weight | GG g/L | GG % Dry Cell Weight | GGPP Synthase Activity (nmol/min/mg) |
|---|---|---|---|---|---|---|---|
| SWE23-ΔE91/YEp352 | 236 | 43.9 | 2.32 | 5.3 | 0 | 0 | not detected |
| EMS9-23/pTWM110-11 | 239 | 41.9 | 2.10 | 5.0 | 0.42 | 1.0 | 0.2 |
| SWE23-ΔE91/pSW4A-3 | 236 | 43.5 | 2.47 | 5.7 | 0.59 | 1.4 | 1.1 |

Example 6

This example illustrates the effect of overexpressing the ERG20 gene which encodes FPP synthase.

To determine the effects of elevating FPP synthase levels in erg9 mutants, the ERG20 gene coding for FPP synthase from *Saccharomyces cerevisiae* was cloned for overexpression.

To determine the effects of FPP synthase overexpression in erg9 mutant strains, representative transformants constructed as described above were grown in shake flask cultures and compared for growth, farnesol production, GG production and FPP synthase and GGPP synthase activities. The strains were grown with shaking at 30° C. for 48 hours in liquid SCE-ura medium, then used to inoculate flasks containing YPDE medium, such that the initial $OD_{600}$ was 0.5. These cultures were incubated at 30° C. with shaking for an additional 72 hours and analyzed for dry cell weight, farnesol and GG levels. A second set of flasks containing 20 ml of SCE-ura medium was also inoculated from the same starting cultures and was grown for 48 hours. The cells from these flasks were harvested, washed with 10 ml 50 mM BisTris-Propane buffer, pH 7.0, and repelleted. The cell pellets were then used to prepare permeabilized cell suspensions for FPP and GGPP synthase assays. The cells were permeabilized by resuspending in 1 ml of 50 mM Bis-Tris-Propane buffer, pH 7.0, containing 0.1% Triton X100, and frozen at 80° C. until needed. After thawing, the permeabilized cells were used for assays. The GGPP synthase assay mixture was the same as described in Example 5. The FPP synthase assay mixture contained 0.05 M Bis-Tris propane buffer, pH 7.0 (X μl), 0.1M dithiothreitol (1 μl), 0.5M $MgCl_2$ (2 μl), 1 mg/ml IPP (6 μl), 1 mg/ml geranyldiphosphate (GPP) (6 μl), and permeabilized cells (Y μl), where X+Y=85 μl. A control reaction was included in which the IPP and GPP were omitted. The assay mixtures were incubated at 37° C. for 15 minutes. 0.1 ml of 2× glycine buffer (0.2M glycine, 2 mM $MgCl_2$, 2 mM $ZnCl_2$, pH 10.4) and 63 units of alkaline phosphatase (Sigma Chemical Co., St. Louis, Mo.) were added, and the mixtures were incubated for 60 minutes at 37° C. The mixtures were then extracted with 0.2 ml 1:1 hexane:ethyl acetate, and analyzed for Farnesol by GC/MS. FPP synthase activity is expressed as nmol FPP formed/min/mg protein.

The data presented in Table 15 show that overexpression of FPP synthase did not increase farnesol production, but did, unexpectedly, increase GG production in these shake flask cultures. The level of GG produced by SWE23-ΔE91/pJMB19-31 or SWE23-ΔE91/pJMB19-32 was even higher than observed for the strain (EMS9-23/pTWM110-11) overexpressing the S. cerevisiae BTS1 (GGPP synthase) gene.

Figure 6:
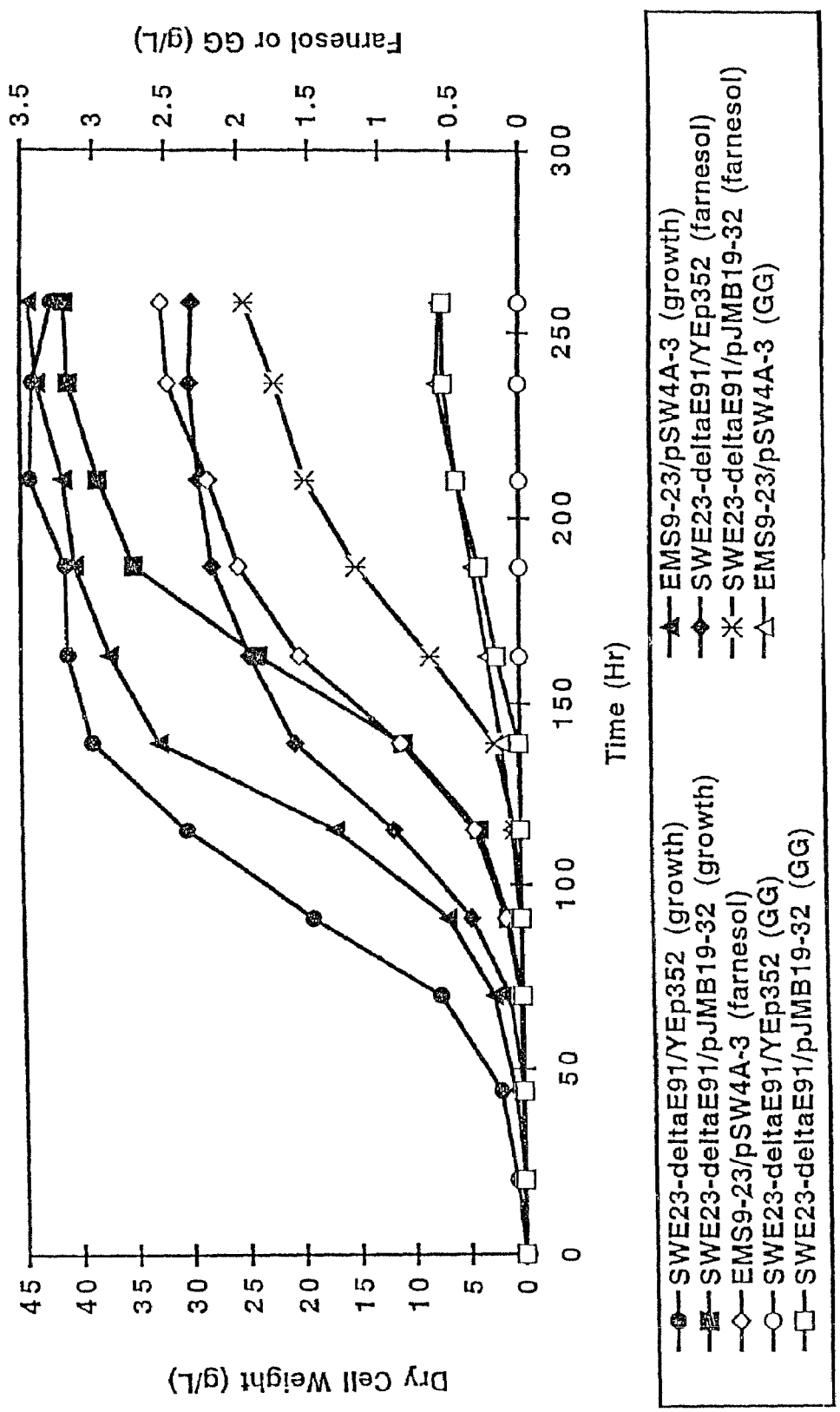
FIG. 6 illustrates the effect of amplified production of FPP synthase on farnesol and GG production.

The effect of amplification of FPP synthase activity on GG production was further evaluated in 1-L fermentors. Strains SWE23-ΔE91/YEp352 (control), EMS9-23/pSW4A3 (crtE, GGPP synthase) and SWE23-ΔE91/pJMB19-32 (ERG20, FPP synthase) were grown in 1-liter fermentors using the method described in Example 1.H., and growth, farnesol production, GG production and GGPP synthase activity were compared (FIG. 6 and Table 16). The growth of the three strains was similar, although SWE23-ΔE91/pJMB19-32 lagged behind before growing at a rate similar to the other strains. Strain SWE23-ΔE91/YEp352 produced 2.31 g/L farnesol in 258 hours, and did not produce any detectable GG. EMS9-23/pSW4A3 produced 2.52 g/L farnesol and 0.57 g/L GG in 258 hours. Strain SWE23-ΔE91/pJMB19-32 produced 1.95 g/L farnesol in 258 hours and also produced 0.59 g/L GG in the same period. The unexpected GG production by SWE23-ΔE91/pJMB19-32 correlated to increased GGPP synthase activity in this strain (see below).

No GGPP synthase activity was detected in the control strain SWE23-ΔE91/YEp352. Strain EMS9-23/pSW4A3, expressing the E. uredovora crtE (GGPP synthase) gene showed relatively high GGPP synthase activity (1.7 nmol/min/mg in cells from the 258-hour time point). As expected, strain SWE23-ΔE91/pJMB19-32, which overexpresses the S. cerevisiae FPP synthase, contained FPP synthase activity that was elevated >10-fold at all time points across the fermentation compared to a control having only normal levels of FPP synthase (data not shown). Surprisingly, however, strain SWE23-ΔE91/pJMB19-32 also had elevated GGPP synthase activity (Table 16). This activity undoubtedly accounts for the unexpected GG production by this strain.

The elevated GGPP synthase activity detected in strain SWE23-ΔE91/pJMB19-32 could be a result of the overexpression of FPP synthase inducing the activity of the GGPP synthase (the BTS1 gene product). It is also possible, however, that the FPP synthase has some low level of GGPP synthase activity which is revealed in this strain because of the high degree of overproduction of the FPP synthase.

TABLE 15

GG production in erg9 mutants overexpressing FPP synthase and GGPP synthase

| Strain/plasmid | Cloned gene (enzyme encoded) | Dry cell weight (g/L) | FOH (% of dry cell weight) | GG (% of dry cell weight) | FPP synthase activity (nmol/min/mg) | GGPP synthase activity (nmol/min/mg) |
|---|---|---|---|---|---|---|
| EMS9-23/YEp352 | — | 3.32 | 9.24 | 0.17 | 2.3 | Not detected |
| EMS9-23/pTWM110-11 | BTS1 (GGPP synthase) | 3.12 | 8.98 | 1.73 | Not tested | 0.19 |
| SWE23-ΔE-91/pJMB19-31 | ERG20 (FPP synthase) | 3.11 | 7.85 | 2.28 | 53.0 | Not tested |
| SWE23-ΔE-91/pJMB19-32 | ERG20 (FPP synthase) | 3.28 | 8.08 | 2.29 | 51.0 | Not tested |

TABLE 16

Effect of Amplified FPP Synthase on Growth, Farnesol and GG Production of Strains Grown in 1-L Fermentors

| Strain/plasmid | Time (hr.) | Dry Cell Weight (g/L) | Farnesol g/L | Farnesol % of Dry Cell Weight | GG g/L | GG % of Dry Cell Weight | GGPP Synthase Activity (nmol/min/mg) |
|---|---|---|---|---|---|---|---|
| SWE23-ΔE91/ Yep352 | 258 | 42.2 | 2.31 | 5.5 | 0 | 0 | Not detected |
| EMS9-23/ pSW4A3 | 258 | 44.3 | 2.52 | 5.3 | 0.57 | 1.28 | 1.7 |
| SWE23-ΔE91/ pJMB19-32 | 258 | 41.1 | 1.95 | 4.7 | 0.55 | 1.34 | 1.0 |

Example 7

This example evaluates several farnesol extraction procedures.

In the first experiment, a comparison was made between extraction of the whole broth (cells plus medium) and separate extractions of the cell pellet and medium under various conditions for MBNA1-13 (farnesol producer) and ATCC 28383 (ergosterol producer) (see Example 1). A 10 ml sample of culture was extracted generally as described in Example 1, but with the changes indicated in Table 17a below. Method 1 in Table 17a is the same as the extraction method described in Example 1. It was found that, for farnesol extraction, a whole broth extraction was just as efficient as a separate cell and medium extraction for methods 1, 2, 3, 5 and 7. The most farnesol was extracted by method 5, which is just a 2 ml addition of 0.2% pyrogallol in methanol prior to extracting the whole broth into hexane. The second highest extraction was method 1.

TABLE 17a

| Extraction method | pyrogallol 0.2% in MeOH | 60% KOH in dH2O | Incubation 75°, 1.5 h | Hexane |
|---|---|---|---|---|
| 1 | 2 ml | 1 ml | yes | 5 ml |
| 2 | 2 ml | 1 ml | no | 5 ml |
| 3 | 2 ml | 0 | yes | 5 ml |
| 4 | 0 | 1 ml | yes | 5 ml |
| 5 | 2 ml | 0 | no | 5 ml |
| 6 | 0 | 1 ml | no | 5 ml |
| 7 | 0 | 0 | no | 5 ml |

Next, experiments were conducted to determine the effects of the type of extraction solvent (method 1, whole broth), times used for extraction (method 1, hexane extraction, whole broth), and the amount of methanol added prior to extraction (method 1, hexane extraction, whole broth). The results are presented in the Tables 17b-19 below.

TABLE 17b

| Solvent | Farnesol (ng) |
|---|---|
| Hexane | 3273 |
| Chloroform | 2262 |
| Ethyl acetate | 3549 |
| N-heptane | 3560 |
| Hexadecane | Not determined* |
| Dodecane | 3529 |
| Toluene | 1055 |
| Carbon tetrachloride | 2023 |

TABLE 17b-continued

| Solvent | Farnesol (ng) |
|---|---|
| Isobutyl Alcohol | 2892 |
| 1-Octanol | 1814 |

*Solvent peak coeluted with farnesol, making quantification of farnesol impossible using this method.

TABLE 18

| Vortex time (min) | Farnesol (ng) |
|---|---|
| 0 | 204 |
| 0.25 | 2794 |
| 0.5 | 2691 |
| 1.0 | 2894 |
| 1.5 | 3302 |
| 2.0 | 3348 |
| 2.5 | 3357 |
| 3.0 | 3545 |
| 3.5 | 3535 |

TABLE 19

| Methanol volume (ml) | Farnesol (ng) |
|---|---|
| 0 | 3440 |
| 0.2 | 2820 |
| 0.4 | 3000 |
| 0.6 | 3440 |
| 0.8 | 3690 |
| 1.0 | 3730 |
| 1.2 | 4580 |
| 1.4 | 4350 |
| 1.6 | 4020 |
| 1.8 | 3880 |

Further work was done to optimize and simplify the extraction procedure for farnesol, and to adapt the procedure for extraction of GG from fermentation broths. This work resulted in the final extraction protocol described below.

1. Whole fermentation broth is used undiluted or diluted appropriately with water to a final volume of 2.0 ml in a 15 ml teflon capped glass test tube.
2. 2.0 ml of hexane is added.
3. 2.0 ml of methanol is added.
4. The tube is vortexed at high speed for 3.5 minutes.
5. The sample is centrifuged at 2,800 rpm in a table top centrifuge for 25-30 minutes to separate the phases.
6. The supernatant (organic phase) is removed and placed in a 2.0 ml teflon capped glass GC/MS vial for determination of farnesol and GG by GC/MS.

Example 8

The following example demonstrates the effect of HMG CoA reductase amplification on GG production by a strain over-expressing GGPP synthase.

In this experiment, a strain was constructed that contained a single copy of a plasmid integrated into its genome that allows the cells to over-express GGPP synthase. The integrating plasmid is known as pSW35-42, and was constructed as follows. Plasmid pSW4A (see Example 5) was digested with BamHI to generate a 2199 bp fragment containing a fusion of the ADH1 promoter, crtE coding sequence, and ADH1 terminator. This fragment was then ligated into BamHI digested YIp351 (Hill et al, 1986, *Yeast/E. coli Shuttle Vectors with Multiple Unique Restriction Sites*, YEAST 2:163-167) to generate pSW35-42.

To construct a strain containing pSW35-42, this plasmid was digested with the restriction endonuclease BstEII to introduce a single cut within the LEU2 gene. The linearized plasmid was purified and used to transform strain SWE23-DL1 using the LiOAc method. Transformants in which pSW35-42 had integrated at the LEU2 locus were selected on medium lacking leucine. One of the resulting transformed strains is referred to as SWE23-DL1::pSW35-42. This strain was then transformed with either YEp352 (an empty vector control, Hill et al, 1986, YEAST 2:163-167) or with pRH124-31 (contains the catalytic domain of the HMG2 gene, see Example 4), which resulted in strains SWE23-DL1::pSW35-42/YEp352 and SWE23-DL1::pSW35-42/pRH124, respectively. Strain SWE23-DL1::pSW35-42/YEp352 over-expresses GGPP synthase while SWE23-DL1::pSW35-42/pRH124 over-expresses GGPP synthase and HMG CoA reductase.

Fermentation experiments of strains SWE23-DL1::pSW35-42/pRH124 and SWE23-DL1::pSW35-42/Yep352 were conducted to compare the GG production by these two strains. The strains were tested for GG production in 1-L fermentors using the protocol described in Example 1.H. The fermentation data are presented in Table 20. This experiment shows that the fermentation of SWE23-DL1::pSW35-42/pRH124 accumulated more GG than the fermentation of SWE23-DL1::pSW35-42/Yep352, and demonstrates that elevation of HMG CoA reductase activity in a strain designed to produce GG resulted in a further elevation of GG levels as compared to a similar strain with un-amplified HMG CoA reductase.

A second approach to achieve over-expression of HMG CoA reductase and GGPP synthase in the same strain was accomplished by cloning both genes into a high copy-number yeast vector, and transforming this plasmid into an erg9 mutant strain. The plasmid used for this purpose is referred to as pSW46-1, and this was constructed as follows. Plasmid pSW4A (see Example 5) was digested with EcoRI and SacI and the 0.9 kb fragment containing the crtE gene was purified and ligated into EcoRI, SacI digested pADH313-956 to generate pSW38-10. Two regions of this plasmid were deleted by digestion with restriction enzymes, filling the ends of the DNA using Pfu polymerase, and ligating to reform the circular plasmid. The regions deleted in this manner were between the NdeI and SpeI sites, and between the HindIII and PstI sites. The resulting plasmid is referred to as pSW43-5. Plasmid pSW43-5 was digested with BamHI, and the resulting 2199 bp fragment containing the ADH1 promoter, crtE gene, and ADH1 terminator (referred to as the ADHp/crtE/ADHt fragment) was purified and ligated into the BamHI site of YEp352. The resulting plasmid is referred to as pSW44-17, and differs from pSW4A in that it contains one instead of two PstI sites.

Plasmid pRH124-31 was digested with XbaI and PstI and the 3.2 kB fragment containing the GPD promoter, HMG2 catalytic domain gene, and the PGK terminator (referred to as the GPDp/HMG2cat/PGKt fragment) was cloned into XbaI, PstI digested pSW44-17 to generate pSW46-1. This plasmid replicates to high copy number in yeast and contains both HMG2 and crtE genes, providing for over-expression of HMG CoA reductase and GGPP synthase. Plasmid pSW46-1 was transformed into the erg9 mutant strain SWE-DE91, and URA+ transformants were isolated. Several of the resulting transformants were tested in a shake flask experiment and were compared to a strain that over-expresses only GGPP synthase (EMS9-23/pSW4A). The results from that experiment are presented in Table 21, and demonstrate that higher levels of GG accumulate in strains that over-express both HMG CoA reductase and GGPP synthase when compared to a strain that over-expresses only GGPP synthase.

TABLE 21

| Strain | Over-expressed Genes | Dry Cell Wt. mg/ml | GG mg/ml | GG % Dry Wt. |
|---|---|---|---|---|
| SWE23-ΔE91/YEp352 | control | 4.35 | 0.0007 | 0.02 |
| EMS9-23/pSW4A | GGPP synthase | 2.82 | 0.0469 | 1.66 |
| SWE23-ΔE91/pSW46-1 | GGPP synthase HMG CoA reductase | 3.45 | 0.0866 | 2.45 |

TABLE 20

| Strain | Dry Cell Weight @ 192 hr g/l | Farnesol @ 192 hr g/l | Farnesol @ 192 hr % dry wt. | GG @ 192 hr g/l | GG @ 192 hr % dry wt. |
|---|---|---|---|---|---|
| SWE23-ΔL1::pSW35-42/Yep352 | 41.4 | 2.04 | 4.9 | 0.30 | 0.72 |
| SWE23-ΔL1::pSW35-42/pRH124 | 44.0 | 3.27 | 7.4 | 0.60 | 1.36 |

These data support the idea that over-expression of HMG CoA reductase in a strain that is capable of producing elevated levels of GG leads to a further increase in the amount of GG produced.

Example 9

The following example describes the production of more stable strains that over-express HMG CoA reductase.

As described in Example 4, strains were constructed that over-expressed HMG CoA reductase due to the presence of high-copy number replicating plasmids containing the HMG1cat or HMG2cat genes. Since replicating plasmids can frequently be lost during cell division, this mitotic instablity of the replicating plasmids can lead eventually to cultures with a high proportion of cells containing only normal HMG CoA reductase levels. In order to obtain more stable strains that over-expressed HMG CoA reductase, copies of the gene coding for the catalytic domain of HMG2p were integrated into the genome of strain SW23B. This was accomplished by first constructing a plasmid that allowed for multiple integrations of the HMG2 gene into the spacer region of the rRNA gene. This approach is modeled after the rDNA integration method described by Lopes et al, 1989 (Lopes, T. S., Klootwijk, J., Veenstra, A. E., van der Aar, P. C., van Heerikhuizen, H., Raue, H. A., and Planta, R. J. 1989. High-copy-number integration into the ribosomal DNA of *Saccharomyces cerevisiae*: a new vector for high-level expression. Gene 79:199-206).

PCR was used to amplify two regions of the rDNA locus that lie in the intergenic region between the gene coding for the 35S rRNA and the gene coding for the 5S rDNA, referred to here as the rDNA spacer region. The oligonucleotides used to amplify the first of the two rDNA spacer region fragments contained sequences corresponding to bases # 11161 to # 11130 and the reverse complement of # 10311 to # 10330 of Gene Bank Accession #Z73326. The oligonucleotide sequences are listed below. The lower case letters are used to indicate bases that were altered or added to create restriction endonuclease recognition sites, which are indicated in parentheses following the oligonucleotide sequence.

```
SEQ ID NO:24:
R6XbaI Lo    5'-tctagaGGCACCTGTCACTTTGGAAA  (XbaI)
             AAAAATATACGC-3'

SEQ ID NO:25:
R7SacII Up   5'-ccgcggGCCGGAAATGCTCTCTGTT  (SacII)
             C-3'
```

The DNA fragment generated from PCR amplification using these two oligonucleotides is referred to herein as the R6/R7 fragment. The R6/7 fragment generated by PCR was cloned initially into the plasmid pCR-Script to generate pSW48-1, then cut from this plasmid by digestion with XbaI and SacI. The resulting 759 bp fragment was then cloned into XbaI, SacI digested pBluescript SK– (Stratagene) to generate pSW49-1.

The oligonucleotides used to amplify the second rDNA spacer region fragment contained sequences corresponding to bases #11247 to #11272 and the reverse complement of #12054 to #12072 of Gene Bank Accession #Z73326. The sequences of these oligonucleotides are listed below.

```
SEQ ID NO:26:
R5Sal UpB    5'CACgtCgACCATTCAAACTTTACTAC-3'  (SalI)

SEQ ID NO:27:
R4ApaI LoB   5'-GAGGGCccGGTCCAGACAT-3'       (ApaI)
```

The DNA fragment generated from PCR amplification using the two oligonucleotides listed above is referred to herein as the R4/R5 fragment. The R4/R5 fragment generated by PCR was digested with ApaI and SalI, and ligated into ApaI, SalI digested pSW49-1 to generate pSW52-11.

PCR was used to amplify the TRP1 gene such that the gene carried an incomplete promoter. The incomplete promoter was intended to reduce expression of the TRP1 gene, and thereby provide a means of selection for high copy number integration of the final expression cassette. The oligonucleotides used to the TRP1 gene contained sequences corresponding to bases #53 to #73 and the reverse complement of #804 to #823 of Gene Bank Accession #J01374. The oligonucleotide sequences are listed below.

```
SEQ ID NO:28:
TRP1 SmaUp   5'-cccgggTATTGAGCACGTGAGTATAC  (SmaI)
             G-3'

SEQ ID NO:29:
TRP1 BamLo   5'-ggatccGGCAAGTGCACAAACAATA  (BamHI)
             C-3'
```

In the next step, pSW50-1 was digested with BamHI and SmaI, and the resulting 779 bp TRP1 fragment was purified. Plasmid pRH124-31 was digested with PstI and SmaI to generate a 3261 bp fragment containing the GPD promoter, HMG2 cat gene, and the PGK terminator (referred to as the GPDp/HMG2cat/PGKt fragment), and this fragment was purified. The TRP1 fragment and the GPDp/HMG2cat/PGKt fragment were ligated into PstI, BamHI digested pSW52-11 in a three fragment ligation to generate pSW58-77 and pSW58-45.

The DNA fragment containing the R6/R7-TRP1-GPD p/HMG2cat/PGK t-R4/R5 gene fusions was cut from pSW58-77 by digestion with the restriction endonucleases KpnI and SacI. The 5671 bp fragment corresponding to the integrating construct was purified and used to transform strain SW23B. Transformants were selected on SCE-trp medium. Strains isolated in this manner were screened for elevation of HMG CoA reductase activity and by Southern blot analysis for elevation of HMG2 gene copy number. Strains were identified that carried one copy of the integrating construct, two copies of the integrating construct, three copies of the integrating construct, and eight copies of the integrating construct, and are referred to as SW23B#19, SW23B#31, SW23B#40, and SW23B#74, respectively. Table 22 gives the specific activity of HMG CoA reductase as determined by in vitro enzyme assays, and copy number of the HMG cat gene as determined by Southern blotting. The HMG CoA reductase assay was previously described (Quain, D. E. and Haslam, J. M. 1979. The Effects of Catabolite Derepression on the Accumulation of Steryl Esters and the Activity of β-Hydroxymethylglutaryl-CoA Reductase in *Saccharomyces cerevisiae*. *J. Gen. Microbiol.* 111:343-351).

TABLE 22

| Strain | HMG CoA Reductase nmol/min mg | GPDp/HMG2cat/PGKt copies/cell |
|---|---|---|
| SW23B | 5.26 | 0 |
| SW23B#19 | 14.53 | 1 |
| SW23B#31 | 37.47 | 2 |
| SW23B#40 | 50.33 | 3 |
| SW23B#76 | 59.04 | 8 |

These strains require exogenously supplied leucine and uracil for growth due to the leu2 and ura3 mutations in these strains. To eliminate the need to supply these nutrients during fermentation experiments, the strains were transformed with a plasmid, pTWM138, containing functional copies of URA3, LEU2, and TRP1. The presence of this plasmid in these strains allowed the strains to grow without leucine and uracil supplementation.

Fermentation experiments were carried out to compare farnesol production by these strains. Also included in this experiment was the strain SWE23-DE91/pRH124-31 which contains the GPDp/HMG2cat/PGKt gene fusion on a high copy number plasmid (see Example 4.B). The strains were tested for farnesol production in 1-L fermentors using the protocol described in Example 1.H, and the data from this experiment are presented in Table 23.

TABLE 23

| Strain | Genes Amplified copy no. | Ferm Time hr | Dry Cell Weight g/l | Farnesol g/l | % Dry Cell Wt. |
|---|---|---|---|---|---|
| SW23B/pTWM138 | control | 216 | 53.3 | 3.25 | 6.10 |
| SW23B#19/pTWM 138 | HMG2 cat 1 copy | 192 | 52.4 | 4.58 | 8.74 |
| SW23B#74/pTWM 138 | HMG2 cat 8 copies | 216 | 43.5 | 4.70 | 10.80 |
| SW23B/pRH124-31 | HMG2 cat >20 copies | 192 | 43.8 | 4.89 | 11.16 |

These data support the idea that strains with elevated levels of HMG CoA reductase produce more farnesol than a strain with normal levels of HMG CoA reductase. The data also indicate that a strain containing eight integrated copies of the HMG2cat gene produce essentially as much farnesol as a strain that carries more than 20 extrachromosomal copies of the HMG2cat gene as is the case with strain SW23B/pRH124-31. A strain containing a single integrated copy of the HMG2 cat gene produced more farnesol than the control strain, but slightly less than strains with more copies of the HMG2cat gene. In addition, the strains containing elevated HMG CoA reductase levels accumulated mevalonate in the culture while the strains with normal levels of HMG CoA reductase did not. This suggests that a step downstream of HMG CoA reductase limits carbon flux in the pathway once the HMG CoA reductase enzyme activity has been elevated (see Example 10). Carbon flux through the pathway is restricted by the activity of one of the enzymes downstream of HMG CoA reductase resulting in mevalonate accumulation in the medium.

Example 10

This example shows the effects of over-expression of multiple isoprenoid pathway genes in a strain that has an erg9 mutation and elevated levels of HMG CoA reductase.

As shown in Examples 4 and 9, elevation of HMG CoA reductase levels led to higher carbon flux through the isoprenoid/sterol pathway. Over-expression of other isoprenoid pathway genes in strains containing amplified HMG CoA reductase may further increase carbon flux through this pathway. Amplification of isoprenoid pathway genes in strains that have elevated levels of HMG CoA reductase as well as a defective erg9 gene may result in further elevation of farnesol levels. Also, amplification of isoprenoid pathway genes may result in further elevation of GG levels in strains that have a defective erg9 gene and have elevated levels of HMG CoA reductase and GGPP synthase.

To test these ideas, plasmids were constructed that allowed for the over-expression of multiple isoprenoid pathway genes. One of the plasmids provided for the over-expression of mevalonate kinase, phosphomevalonate kinase, and diphosphomevalonate decarboxylase, coded by the ERG12, ERG8, and ERG19 genes respectively. This plasmid is referred to as pSW77-69, and was constructed from DNA fragments obtained from a number of plasmids containing single isoprenoid pathway genes. The construction of those plasmids is described first.

PCR was used to amplify the ERG12 gene for cloning. The oligonucleotides used to amplify the ERG12 gene contained sequences corresponding to bases #2827 to #2846 and the reverse complement of #5247 to #5229 of Gene Bank Accession #Z49809. The sequences of the two oligonucleotides are given below. The lower case letters are used for bases that were altered or added to create restriction endonuclease recognition sites, which are indicated in parentheses following the oligonucleotide sequence.

```
SEQ ID NO:30:
E12.4SN         5'-CCAAATATAACtCGAGCTTTG-3'    (XhoI)

SEQ ID NO:31:
E12.SALI3       5'-GCAAAGTcCaCCACCGCAG-3'     (SalI)
```

The ERG12 gene was amplified using the two oligonucleotides E12.4SN and E12.5AL13 and genomic DNA from strain ATCC 28383. The resulting DNA was cloned into pCR-Script at the SfrI site to generate pSW68.

The oligonucleotides used to amplify the ERG19 gene contained sequences corresponding to bases #911 to #937 of Gene Bank Accession #Z71656 and the reverse complement of bases #1930 to #1962 of Gene Bank Accession #Z71658. The sequences of the two oligonucleotides are given below.

```
SEQ ID NO:32:
E19 SMAI    5'-GCCACGTGCCCcCGGGTTTCTCTAGCC-    (SmaI)
            3'

SEQ ID NO:33:
E19 SACI3   5'-GGAAAAGagCtCGATAATTATTGATGAT    (SacI)
            AGATC-3'
```

The ERG19 gene was amplified using the two oligonucleotides E19 SMAI, E19 SACI3, and genomic DNA from strain ATCC 28383. The resulting DNA was cloned into pCR-Script at the SfrI site to generate pSW69.

The oligonucleotides used to amplify the ERG8 gene contained sequences corresponding to bases #2729 to #2749 and the reverse complement of #5177 to #5196 of Gene Bank Accession #Z49939. The sequences of the two oligonucleotides are given below.

```
SEQ ID NO:34:
E8.2135N    5'-CCGTTTTGGATccTAGATCAG-3'       (BamHI)

SEQ ID NO:35:
E8SMAI3     5'-gttcccGGGTTATTGTCCTGCATTT      (SmaI)
            G-3'
```

The ERG8 gene was amplified using the two oligonucleotides E8.2135N, E8SMAI3, and genomic DNA from strain ATCC 28383. The resulting DNA was cloned into pCR-Script at the SfrI site to generate pSW71.

Plasmid pSW71 was digested with BamHI and SmaI, and the resulting 2459 bp fragment containing the ERG8 gene was purified. Plasmid pSW69-3 was digested with SmaI and SacI, and the resulting 2239 bp fragment containing the ERG19 gene was purified. The high copy number yeast vector YEp352 (containing a URA3 selection marker) was digested with BamHI and SacI and purified. The three purified DNA fragments were ligated together to generate pSW76-11.

Next, pSW68 was digested with SalI and XhoI and the resulting 2400 bp band containing the ERG12 gene was purified and ligated into SalI digested pSW76-11 to generate pSW77-69. This plasmid contains ERG12, ERG8, and ERG19, and provides for over-expression of mevalonate kinase, phosphomevalonate kinase, and diphosphomevalonate decarboxylase.

Another plasmid provided for the over-expression of mevalonate kinase, phospho-mevalonate kinase, diphosphomevalonate decarboxylase, and IPP isomerase, coded by ERG12, ERG8, ERG19, and IDI1 genes respectively. This plasmid is referred to as pSW78-68, and was constructed as follows. The IDI1 gene was amplified by PCR for cloning. The oligonucleotides used to amplify the IDI1 gene contained sequences corresponding to bases #19577 to #19604 and the reverse complement of #17477 to #17502 of Gene Bank Accession #U43503. The sequences of the two oligonucleotides are given below.

```
SEQ ID NO:36:
ISO SACI5    5'-AAGAGctcATCTGATAATAGATCAAGC    (SacI)
             G-3'

SEQ ID NO:37:
ISO SACI3    5'-AGGAGCTCAACGACAATAAATGGCTG-    (SacI)
             3'
```

The IDI1 gene was amplified using the two oligonucleotides ISOSACI5, ISOSACI3, and genomic DNA from strain ATCC 28383. The resulting DNA was cloned into pCR-Script at the SfrI site to generate pSW73. Plasmid pSW73 was digested with SacI and the resulting 2117 bp fragment containing the IDI1 gene was ligated with SacI digested pSW77-69 to generate pSW78-68. This plasmid contains ERG12, ERG8, ERG19, and IDI1, and provides for over-expression of mevalonate kinase, phosphomevalonate kinase, diphosphomevalonate decarboxylase, and IPP isomerase.

Another plasmid provided for the over-expression of acetoacetyl CoA thiolase and HMG CoA synthase, coded by the ERG10 and ERG13 genes, respectively. This plasmid is referred to as pSW79-29, and was constructed as follows.

PCR was used to amplify the ERG13 and ERG10 genes for cloning. The oligonucleotides used to amplify the ERG13 gene contained sequences corresponding to the reverse complement of bases #21104 to #21127 and bases #18270 to #18292 of Gene Bank Accession #Z50178. The sequences of the two oligonucleotides are given below.

```
SEQ ID NO:38:
E13 XBAI5    5'-GTCCTctAGATCTTGAATGAAATC-3'    (XbaI)

SEQ ID NO:39:
E13 SACI3    5'-CTTTGAGCtcGTACAAGAAGCAG-3'    (SacI)
```

The ERG13 gene was amplified using the two oligonucleotides E13 XBAI5, E13 SACI3, and genomic DNA from strain ATCC 28383. The resulting DNA was cloned into pCR-Script at the SfrI site to generate pSW72.

The oligonucleotides used to amplify the ERG10 gene contained sequences corresponding to bases #4073 to #4093 and the reverse complement of #6542 to #6565 of Gene Bank Accession #U36624. The sequences of the two oligonucleotides are given below.

```
SEQ ID NO:40:
E10 HIND5    5'-CTAAGCttTGCGCCCGTGAAG-3'    (HindIII)

SEQ ID NO:41:
E10 XBAI3-2  5'-GTTCTAGAAGTTTTCAAAGCAGA    (XbaI)
             G-3'
```

The ERG10 gene was amplified using the two oligonucleotides E10 HIND5, E10 XBAI3-2, and genomic DNA from strain ATCC 28383. The resulting DNA was cloned into pCR-Script at the SfrI site to generate pSW70.

Plasmid pSW70 was digested with XbaI and HindIII, and the resulting 2482 bp fragment containing the ERG10 gene was purified. Plasmid pSW72-4 was digested with XbaI and SacI, and the resulting 2850 bp fragment containing the ERG13 gene was purified. The two purified DNA fragments were then ligated together with SacI, HindIII digested YEp351 (LEU2 selectable marker) to generate pSW79-30. This plasmid contains the ERG13 and ERG10 genes and allows for the over-expression of acetoacetyl CoA thiolase and HMG CoA synthase.

Strain SW23B#74 (contains eight integrated copies of the HMG2 cat gene, see Example 9) was transformed with pSW77-69 and pSW78-68, and transformants were selected on SCE-ura medium. The resulting strains are referred to as SW23B#74/pSW77-69 and SW23B#74/pSW78-68, respectively. These strains require added leucine for growth due to the leu2 mutation. To eliminate the need to supplement these strains with leucine during fermentation experiments, they were transformed with a linear fragment of DNA containing a functional LEU2 gene, and LEU+ transformants were isolated. These strains are referred to as SW23B#74L/pSW77-69 and SW23B#74L/pSW78-68, respectively.

SW23B#74 was also transformed with pSW79-30, and transformants were selected on SCE-leu medium. SW23B#74/pSW79-30 requires uracil since it contains a mutation in the ura3 gene. To eliminate the need to supplement these strains with uracil during fermentation experiments, this strain was transformed with a linear fragment of DNA containing a functional URA3 gene, and URA+ transformants were isolated. This strain is referred to as SW23B#74U/pSW79-30.

SW23B#74 was also transformed with both pSW78-68 and pSW79-30, and transformants were isolated that were capable of growing on SCE-ura,-leu medium indicating that the transformants contained both plasmids. The resulting strain is referred to as SW23B#74/pSW78-68/pSW79-30.

Fermentation experiments were carried out with the strains described above to examine the effect of these gene amplifications on farnesol production. The strains were tested in 1-L fermentors using the protocol described in Example 1.H, and data from these experiments are presented in Table 24.

TABLE 24

| Strain | Genes Amplified | Ferm. Time (hr) | Dry Cell Weight g/l | Farnesol g/l | Farnesol % Dry Wt. | Mevalonate g/l | Mevalonate % Dry Wt. |
|---|---|---|---|---|---|---|---|
| SW23B#74/ pTWM138 | HMG2cat | 215 | 45.5 | 4.95 | 10.88 | 0.2 | 0.4 |
| SW23B#74L/ pSW77-69 | HMG2cat, ERG8, ERG12, ERG19, | 287 | 41.6 | 4.67 | 11.23 | 0 | 0 |
| SW23B#74L/ pSW78-68 | HMG2cat, ERG8, ERG12, ERG19, IDI1 | 215 | 46.4 | 4.87 | 10.50 | 0 | 0 |

TABLE 24-continued

| Strain | Genes Amplified | Ferm. Time (hr) | Dry Cell Weight g/l | Farnesol g/l | Farnesol % Dry Wt. | Mevalonate g/l | Mevalonate % Dry Wt. |
|---|---|---|---|---|---|---|---|
| SW23B#74U/ pSW79-30 | HMG2cat, ERG10, ERG13 | 215 | 46.1 | 4.63 | 10.04 | 5.4 | 11.7 |

These data show that a strain which over-expresses HMG CoA reductase accumulates the isoprenoid pathway intermediate mevalonate in the culture medium. Since mevalonate accumulation is not observed in strains with normal levels of HMG CoA reductase, this demonstrates that carbon flux through the isoprenoid pathway has been increased by HMG CoA reductase amplification to the point where another step subsequent to HMG CoA reductase limits the conversion of pathway intermediates. Furthermore, over-expression of the first three enzymes in the isoprenoid pathway, namely acetoacetyl CoA thiolase, HMG CoA synthase, and HMG CoA reductase (coded by ERG 13, ERG10, and HMG2cat, respectively) led to even higher accumulation of mevalonate in the medium. This demonstrates that carbon flux into the isoprenoid pathway has been increased further by amplification of the first three steps, and emphasizes that one of the enzymes downstream of HMG CoA reductase limits conversion of isoprenoid pathway intermediates. Since mevalonate serves as a precursor to farnesol and GG, the modifications described above can be used to increase carbon flux into the isoprenoid pathway, and, if the mevalonate can be more efficiently metabolized, can lead to increased farnesol and GG accumulation.

In regard to this last point, enzymes downstream of HMG CoA reductase were amplified in a strain that over-expressed HMG CoA reductase. The enzymes amplified were HMG CoA reductase, mevalonate kinase, phosphomevalonate kinase, diphosphomevalonate decarboxylase, and IPP isomerase (coded by HMG2cat, ERG12, ERG8, ERG19, and IDI1, respectively). These strains accumulated less mevalonate when compared to strains over-expressing only HMG CoA reductase, indicating that the increased flux through the isoprenoid pathway resulting from HMG CoA reductase over-expression was accommodated by elevated levels of the downstream enzymes. Although elevated farnesol levels were not observed in the experiment described above, this may be due to the low level of mevalonate available for conversion. However, these data suggest that amplification of one or more of the enzymes downstream of HMG CoA reductase in a strain with amplified levels of the first three pathway enzymes may lead to increased accumulation of farnesol and GG since flux to mevalonate is greatly increased in these strains. It is likely that over-expression of one or more genes downstream of HMG CoA reductase in a strain that over-expresses acetoacetyl CoA thiolase, HMG CoA synthase, and HMG CoA reductase will lead to significant increases in farnesol and GG accumulation.

Example 11

This example describes an experiment in which squalene synthase is blocked by zaragozic acid in a strain with an intact and functional sterol pathway, including a functional ERG9 gene, and the effect of this squalene synthase inhibitor on farnesol and GG accumulation is observed.

Zaragozic acids are a family of compounds that act as potent inhibitors of squalene synthase (Bergstrom, J. D., Dufresne, C., Bills, G. F., Nallin-Omstead, M., and Byrne, K. 1995. Discovery, Biosynthesis, and Mechanism of Action of the Zaragozic Acids: Potent Inhibitors of Squalene Synthase. Ann. Rev. Microbiol. 49:607-639). They are capable of inhibiting cholesterol biosynthesis in mammals and ergosterol biosynthesis in fungi. Since ergosterol is necessary for fungal cell growth, zaragozic acids are potent fungicidal compounds.

Strain SWE23-E9 (ura3, sue; see EXAMPLE 1.G) was used in this experiment because it contained the sue mutation that provided for the uptake of sterols under aerobic conditions. This allowed the yeast to grow in ergosterol-supplemented medium when squalene synthase was blocked by zaragozic acid. A strain without the sue mutation would not be able to take up sterols, including ergosterol, from the medium, and therefore could not grow in the presence of zaragozic acid.

SWE23-E9 containing either an empty vector (Yep352) or plasmids that allow for the over-expression of HMG Co A reductase (pRH124-31), GGPP synthase (pSW4A), or both HMG Co A reductase and GGPP synthase (pSW46-1) were tested in shake flasks by first growing the strains in SCE-ura medium for 48 hr to select for the plasmids. Samples of these cultures were then inoculated into YPDE medium or YPDE medium containing zaragozic acid at 100 µg/ml. The YPDE (+/−zaragozic acid) cultures were incubated at 30° C. for 48 hr, then analyzed for dry cell weight and farnesol accumulation. The data from this experiment are shown in Table 25. All of the cultures treated with zaragozic acid exhibited elevated accumulation of farnesol relative to the untreated cultures. GG accumulation was not measured in this experiment.

TABLE 25

| Strain | Zaragozic Acid @100 µg/m | Dry Cell Weight mg/ml | Farnesol µg/ml | Farnesol % Dry Wt. |
|---|---|---|---|---|
| SWE23-E9/Yep352 | + | 7.65 | 43 | 0.56 |
| SWE23-E9/Yep352 | − | 9.72 | 0 | 0 |
| SWE23-E9/pRH124-31 | + | 7.88 | 11 | 0.14 |
| SWE23-E9/pRH124-31 | − | 9.89 | 0 | 0 |
| SWE23-E9/pSW4A | + | 7.03 | 45 | 0.64 |
| SWE23-E9/pSW4A | − | 9.05 | 1 | 0 |
| SWE23-E9/pSW46-1 | + | 7.09 | 51 | 0.72 |
| SWE23-E9/pSW46-1 | − | 8.54 | 0 | 0 |

In a separate experiment, SWE23-E9 containing either an empty vector (Yep352) or a plasmid that allows for over-expression of both HMG Co A reductase and GGPP synthase (pSW46-1) were tested in shake flasks by first growing the strains in SCE-ura medium for 48 hr to select for the plasmids. Samples of these cultures were then inoculated into YPDE medium or YPDE medium containing zaragozic acid at 100 mg/ml. The YPDE (+/− zaragozic acid) cultures were incubated at 30° C. for 72 hr, then analyzed for dry cell weight and GG. The data are presented in Table 26. The culture of SWE23-E9/pSW46-1 treated with zaragozic acid exhibited a higher level of GG as compared to the same strain grown in the absence of zaragozic acid. These experiments demonstrate that strains without mutations in the sterol biosynthetic pathway can be induced to accumulate farnesol by blocking the pathway using a squalene synthase inhibitor. The amount of farnesol or GG accumulated by the zaragozic acid treated cultures was much less than the amount accumulated by strains with completely defective erg9 genes indicating that a genetic block of squalene synthase is more effective than a block induced by a squalene synthase inhibitor.

TABLE 26

| Strain | Zaragozic Acid @100 μg/ml | Dry Cell Weight mg/ml | GG μg/ml | % Dry Wt. |
|---|---|---|---|---|
| SWE23-E9/Yep352 | + | 7.17 | 0 | 0 |
| SWE23-E9/Yep352 | − | 9.25 | 0 | 0 |
| SWE23-E9/pSW46-1 | + | 6.68 | 17.8 | 0.27 |
| SWE23-E9/pSW46-1 | − | 8.41 | 6.7 | 0.08 |

Example 12

An alternative pathway leading to FPP has been described in a number of bacteria and plants, and is referred to as the non-mevalonate or Rohmer pathway (Eisenreich, W., Schwarz, M., Cartayrade, A., Arigoni, D., Zenk, M. H., and Bacher, A., 1998. The Deoxyxylulose Phosphate Pathway of Terpenoid Biosynthesis in Plants and Microorganisms. Chem. Biol. 5: R221-233. Paseshnichenko, V. A., 1998. A New Alternative Non-Mevalonate Pathway for isoprenoid Biosynthesis in Eubacteria and Plants. Biochemistry (Mosc) 63:139-148). Some of the enzymes of the non-mevalonate pathway and their genes have been identified and studied in *E. coli*, and these include the deoxyxylulose-5-phosphate synthase, deoxyxylulose-5-phosphate reductase, IPP isomerase, and FPP synthase, coded by the dxr, dxs, idi, and ispA genes, respectively.

In order to construct strains of *E. coli* that accumulate elevated levels of farnesol, plasmids were constructed for the over-expression in *E. coli* of the genes listed above. In some cases, additional genes adjacent to the known isoprenoid pathway gene were included in the cloned DNA.

The idi gene coding for IPP isomerase was PCR amplified using the two oligonucleotides listed below and genomic DNA isolated from *E. coli* strain W3110. The oligonucleotides used to amplify the idi gene contained sequences corresponding to bases #42309 to #42335 and the reverse complement of #43699 to #43726 of Gene Bank Accession #U28375. The lower case letters are used for bases that were altered to create restriction endonuclease recognition sites, which are indicated in parentheses following the oligonucleotide sequence. A natural EcoRI site was used in VE145-5.

```
SEQ ID NO:42:
VE145-5     5'-GGGATTCGAATTCTGTCGCGCTGTAA  (EcoRI)
            C-3'

SEQ ID NO:43:
VE146-3     5'-TGggATCcGTAACGGCTTTAGCGAGC  (BamHI)
            TG-3'
```

The idi PCR product was digested with EcoRI and BamHI, and ligated into EcoRI, BamHI digested pUC19. The resulting clone is referred to as pHS-O182.

The dxr gene was PCR amplified using the two oligonucleotides listed below and genomic DNA isolated from *E. coli* strain W3110. The oligonucleotides used to amplify a region of DNA which included the frr, dxr, and yaeS genes contained sequences corresponding to bases #2131 to #2150 and the reverse complement of #5297 to #5315 of Gene Bank Accession #D83536.

```
SEQ ID NO:44:
DXR17.SN     GATTCCGCGTAAGgATCcCG   (BamHI)

SEQ ID NO:45:
DXR3179.ASN  CCAGCATctAGACCACCAG    (XbaI)
```

The resulting PCR product was digested with BamHI and XbaI, and ligated into BamHI, XbaI digested pHS-O182 to generate pHS-O182R.

The ispA and dxs genes appear to be part of an operon that possibly include two other genes referred to as xseB and yajO. PCR was used to amplify a region of DNA which included xseB, ispA, dxs, and yajO using the oligonucleotides listed below and genomic DNA isolated from *E. coli* strain W3110. The oligonucleotides contained sequences corresponding to bases #4157 to #4183 and the reverse complement of bases # 8938 to #48956 of Gene Bank Accession #AE000148.

```
SEQ ID NO:46:
DXS.5619P    5'-gactgcagCTGGCCGCTGGGTATTCTGT  (PstI)
             CGTAGTT-3'

SEQ ID NO:47:
DXS.820X     5'-gatctagaTCACGCGTACGCAGAAGGTT  (XbaI)
             TTGC-3'
```

The resulting PCR product was digested with XbaI and PstI and ligated to XbaI, PstI digested pUC19 to generate pHS-dxs.

The DNA fragment containing the dxs gene will be cut from pHS-dxs using XbaI and PstI, and ligated into XbaI, PstI digested pHS-O182R to generate a plasmid that contains dxs, dxr, ispA, and idi. The resulting plasmid will be transformed into *E. coli*, and a transformed strain containing the plasmid will be tested for production of farnesol in shake flask and fermentation experiments.

In order to construct strains of *E. coli* that accumulate elevated levels of GG, a plasmid was constructed for the over-expression in *E. coli* of GGPP synthase from *Erwinia herbicola*. The crtE gene coding for GGPP synthase was amplified by PCR using genomic DNA isolated from *Erwinia herbicola* strain Eho10 and the following two oligonucleotides. The oligonucleotides contained sequences corresponding to bases #3513 to #3531 and the reverse complement of bases # 4459 to #4481 of Gene Bank Accession #M87280.

```
SEQ ID NO:48:
Eho10E Up    5'-gaattcCAATTCAGCGGGTAACCT  (EcoRI)
             T-3'

SEQ ID NO:49:
Eho10E Lo    5'-aagcttTGCTTGAACCCAAAAGGG  (HindIII)
             CGGTA-3'
```

The resulting PCR product was digested with EcoRI and HindIII, and ligated into pET24d(+) (Novagen) so that expression of the ctrE gene was controlled by the T7 promoter. The resulting plasmid is referred to as pKL19-63. This plasmid can be transformed into *E. coli* strains such as BL21 (DE3) (available from Novagen) which contains an IPTG inducible gene coding for T7 polymerase. This allows IPTG induction of the crtE gene in this strain. The T7 promoter/crtE gene fusion can be cut from pKL19-63 using BglII and HindIII, and ligated into BamHI, HindIII digested pACYC184 (Accession #X06403) to construct a plasmid relying on chloramphenicol resistance for selection. This plasmid contains the p 15A origin of replication and would be compatible with plasmids containing the ColE1 origin of replication such as the clones carrying the E. coli isoprenoid pathway genes described above. These latter plasmids confer ampicillin resistance, and so E. coli transformants can be obtained that carry both the crtE plasmid and the plasmid containing the dxs, dxr, idi, and ispA genes by transforming E. coli with both plasmids and selecting for resistance to chloramphenicol and ampicillin. Therefore, strains of E. coli BL21(DE3) will be obtained that contain plasmids for over-expression deoxyxylulose-5-phosphate synthase, deoxyxylulose-5-phosphate reductoisomerase, IPP isomerase, FPP synthase, and GGPP synthase. These strains will be tested for production of GG in shake flask and fermentation experiments.

Example 13

The following example describes the construction of strains of Saccharomyces cerevisiae that are engineered to produce elevated levels of farnesol and GG by expressing enzymes corresponding to the non-mevalonate pathway enzymes. Biosynthesis of IPP occurs in many bacteria and plants starting from pyruvate and glyceraldehyde-3- and proceeding through a series of enzymatic steps known as the non-mevalonate pathway, and includes the enzymes deoxyxylulose-5-phosphate synthase and deoxyxylulose-5-phosphate reductoisomerase. The compound resulting from these two enzymatic steps is 2-C-methyl-D-erythritol 4-phosphate (also known as MEP), which is further metabolized by unknown enzymes to yield IPP. Plasmids are constructed that express the E. coli dxs and dxr genes in yeast by fusing the coding regions of those genes to promoter elements that allow for expression in yeast. The dxs and dxs genes are amplified by PCR with oligonucleotides that include restriction sites to allow cloning into yeast expression vectors which contain promoters such as the ADH1 promoter, PGK promoter, or GPD promoter. The two gene fusions are then combined into a single plasmid by subcloning one gene fusion into the other plasmid. The resulting plasmid containing both genes is then transformed into an erg9 mutant of yeast. The resulting strain is capable of synthesizing MEP, which may be further metabolized to IPP by endogenous enzymes capable of carrying out the desired reactions to IPP. This capability may lead to increased accumulation of IPP, which may cause the cells to accumulate elevated levels of farnesol through the action of the endogenous IPP isomerase and FPP synthase enzymes. If this is done in a strain that also over-expresses GGPP synthase, then elevated levels of GG may accumulate in these strains.

Example 14

This example describes the construction of a strain of Saccharomyces cerevisiae that over-expresses a mutated ERG20 gene coding for an FPP synthase enzyme exhibiting altered product specificity. Unlike strains over-expressing wild-type FPP synthase, strains expressing the mutated FPP synthase accumulated more GG than farnesol.

Comparison of the amino acid sequences of FPP synthases from a variety of organisms revealed several highly conserved domains including two aspartate rich domains, which are essential for catalytic activity. Researchers have reported that mutations effecting the amino acid located at the fifth position before the first aspartate rich domain can alter the product specificity of the enzyme such that the enzyme readily catalyzes the formation of GGPP as well as FPP. This has been shown for both avian and Bacillus stearothermophilus FPP synthases (Tarshis, L. C., Proteau, P. J., Kellogg, B. A., Sacchettini, J. C., Poulter, C. D. 1996. Regulation of Product Chain Length by Isoprenyl Diphosphate Synthases. Proc. Natl. Acad. Sci. USA 93:15018-15023; Ohnuma, S., Narita, K., Nakazawa, T., Ishida, C., Takeuchi, Y., Ohto, C., and Nichino, T. 1996. A Role of the Amino Acid Residue Located on the Fifth Position Before the First Aspartate-rich Motif of Farnesyl Diphosphate Synthase on Determination of the Final Product. J. Biol. Chem. 271:30748-30754; U.S. Pat. No. 5,766,911). In the case of the Bacillus enzyme, the amino acid in the fifth position before the first aspartate rich domain was changed from tyrosine to serine. The avian enzyme contains a phenylalanine in this position. It is thought that aromatic amino acids in that position block extension of the isoprenyl chain beyond fifteen carbons, and that the restriction can be alleviated by replacing the phenylalanine with a less-bulky amino acid such as serine.

As in the Bacillus FPP synthases mentioned above, the FPP synthase from Saccharomyces cerevisiae has a tyrosine at the fifth position before the first aspartate rich domain. Site directed mutagenesis was used to alter the sequence of the ERG20 gene to code for a serine instead of a tyrosine at that position. The method used to introduce the mutation relied on PCR amplification of the entire pJMB19-31 plasmid using mutagenic oligonucleotides that introduced the desired mutation, and is outlined in the instruction booklet for the QuikChange Site-Directed Mutagenesis Kit (Stratagene). The oligonucleotides contained sequences corresponding to bases #1063 to #1097 and the reverse complement of bases # 1063 to #1097 of Gene Bank Accession #J05091. The sequences of the oligonucleotides are given below, with the changes indicated by small case letters. An alteration of A to T was made at position #1084 to change the encoded amino acid from tyrosine to serine. Also, an alteration of T to C was made at position #1074 to create a new PstI site, which allowed for rapid identification of the mutant gene. This latter mutation was silent in that it did not change the encoded amino acid.

```
SEQ ID NO:50:
Y95S-SN      5'-GCATTGAGTTGcTGCAGGCTTcCTTCTTGGTCGC
             C-3'

SEQ ID NO:51:
Y95S-ASN     5'-GGCGACCAAGAAGgAAGCCTGCAgCAACTCAATG
             C-3'
```

The two oligonucleotides were used to amplify pJMB19-31, and the resulting PCR product was ligated to itself to reform the circular plasmid, except that ERG20 gene now contained the desired mutation. The resulting plasmid is referred to as pHS31.Y95S, and this plasmid was transformed into the erg9 mutant strain SWE23-DE91 to form SWE23-DE91/pHS31.Y95S. Shake flask experiments were carried out to compare farnesol and GG production by strains over-expressing the wild-type ERG20 gene and the mutated ERG20 gene. Strains were grown overnight in SCE-ura, and this was used to inoculate flasks containing YPDE medium. These cultures were grown at 30° C. for 72 hr, then harvested for dry cell weight and isoprenoid analysis. The data from this experiment is presented in Table 27.

TABLE 27

| Strain | FPP Synthase | Dry Cell Wt mg/ml | Farnesol mg/ml | % Dry Wt. | GG mg/ml | % Dry Wt. |
|---|---|---|---|---|---|---|
| SWE23-DE91/ JMB19-31 | Wild type | 4.7 | 0.22 | 4.76 | 0.05 | 1.1 |
| SWE23-DE91/ pHS31.Y95S | Tyr to Ser Mutant | 4.9 | 0.01 | 0.2 | 0.13 | 2.7 |

These data show that the farnesol:GG ratio is dramatically altered by over-expression of the tyr to ser mutant of the ERG20 gene in an erg9 mutant strain. The strain over-expressing the mutant ERG20 gene exhibited proportionally more GG than the strain over-expressing the wild-type ERG20 gene. In addition, the total amount of GG produced by the strain over-expressing the mutant ERG20 was higher while the total amount of farnesol was lower as compared to the strain over-expressing the wild-type ERG20 gene. The decrease in farnesol level was not completely reflected in the GG pool, suggesting that some of the FPP may be converted to other compounds besides GG. Alternatively, it is possible that feedback inhibition plays a role in regulating the amount of GG accumulated by these strains.

The foregoing description of the invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain best modes known of practicing the invention and to enable others skilled in the art to utilize the invention in such, or other, embodiments and with the various modifications required by the particular applications or uses of the invention. It is intended that the appended claims be construed to include alternative embodiments to the extent permitted by the prior art.

What is claimed is:

1. A recombinant yeast comprising one or more heterologous nucleic acid molecules encoding:
   a. an enzyme that converts pyruvate and D-glyceraldehyde 3-phosphate to 1-deoxyxylose 5-phosphate; and,
   b. an enzyme that converts 1-deoxy-D-xylulose 5-phosphate to 2-C-methyl-D-erythritol 4-phosphate;
   wherein, each of the encoded enzymes is a bacterial enzyme.

2. The yeast of claim 1 wherein the one or more heterologous nucleic acid molecules are on one or more plasmids.

3. The yeast of claim 1 wherein the one or more heterologous nucleic acid molecules are integrated into a chromosome.

4. The yeast of claim 1 wherein the one or more heterologous nucleic acid molecules are under inducible control.

* * * * *

```
                        SEQUENCE LISTING

<160> NUMBER OF SEQ ID NOS: 51

<210> SEQ ID NO 1
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: PRIMER
<220> FEATURE:
<223> OTHER INFORMATION: Description of Artificial Sequence:PRIMER

<400> SEQUENCE: 1
ctcagtacgc tggtacccgt cac                                             23

<210> SEQ ID NO 2
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: PRIMER
<220> FEATURE:
<223> OTHER INFORMATION: Description of Artificial Sequence:PRIMER

<400> SEQUENCE: 2
gatggatccc aatatgtgta gctcagg                                         27

<210> SEQ ID NO 3
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: PRIMER
<220> FEATURE:
<223> OTHER INFORMATION: Description of Artificial Sequence:PRIMER
```

```
<400> SEQUENCE: 3
gcgcatccac gggctatata aa                                              22

<210> SEQ ID NO 4
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: PRIMER
<220> FEATURE:
<223> OTHER INFORMATION: Description of Artificial Sequence:PRIMER

<400> SEQUENCE: 4
gcggatccta ttatgtaagt acttag                                          26

<210> SEQ ID NO 5
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: PRIMER
<220> FEATURE:
<223> OTHER INFORMATION: Description of Artificial Sequence:PRIMER

<400> SEQUENCE: 5
gagcatccac gggctatata aa                                              22

<210> SEQ ID NO 6
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: PRIMER
<220> FEATURE:
<223> OTHER INFORMATION: Description of Artificial Sequence:PRIMER

<400> SEQUENCE: 6
tccccccggg cgcagacttc acgctc                                          26

<210> SEQ ID NO 7
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: PRIMER
<220> FEATURE:
<223> OTHER INFORMATION: Description of Artificial Sequence:PRIMER

<400> SEQUENCE: 7
gatccgcggc tcaagctagc ggtattatgc c                                    31

<210> SEQ ID NO 8
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: PRIMER
<220> FEATURE:
```

<223> OTHER INFORMATION: Description of Artificial Sequence:PRIMER

<400> SEQUENCE: 8
gactctagag tttacgagtc tggaaaatc                               29

<210> SEQ ID NO 9
<211> LENGTH: 28
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: PRIMER
<220> FEATURE:
<223> OTHER INFORMATION: Description of Artificial Sequence:PRIMER

<400> SEQUENCE: 9
gtaggatcca tggaattgag caatagag                                28

<210> SEQ ID NO 10
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: PRIMER
<220> FEATURE:
<223> OTHER INFORMATION: Description of Artificial Sequence:PRIMER

<400> SEQUENCE: 10
aattccaagc ttgcggccgc tctagaacgc gtg                          33

<210> SEQ ID NO 11
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: PRIMER
<220> FEATURE:
<223> OTHER INFORMATION: Description of Artificial Sequence:PRIMER

<400> SEQUENCE: 11
gatccacgcg ttctagagcg gccgcaagct tg                           32

<210> SEQ ID NO 12
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: PRIMER
<220> FEATURE:
<223> OTHER INFORMATION: Description of Artificial Sequence:PRIMER

<400> SEQUENCE: 12
gaattcgttt ataaggacag cccga                                   25

<210> SEQ ID NO 13
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: PRIMER

```
<220> FEATURE:
<223> OTHER INFORMATION: Description of Artificial Sequence:PRIMER

<400> SEQUENCE: 13
ctgcagtcct taactgacgg cagcga                                          26

<210> SEQ ID NO 14
<211> LENGTH: 52
<212> TYPE: DNA
<213> ORGANISM: Artificial Sequence
<220> FEATURE:
<221> NAME/KEY: misc_feature
<222> LOCATION: (1)..(52)
<223> OTHER INFORMATION: PRIMER
<220> FEATURE:
<223> OTHER INFORMATION: Description of Artificial Sequence:PRIMER

<400> SEQUENCE: 14
agctgaattc gagctcggta cccgggctct agagtcgacc tgcaggcatg ca            52

<210> SEQ ID NO 15
<211> LENGTH: 52
<212> TYPE: DNA
<213> ORGANISM: Artificial Sequence
<220> FEATURE:
<221> NAME/KEY: misc_feature
<222> LOCATION: (1)..(52)
<223> OTHER INFORMATION: PRIMER
<220> FEATURE:
<223> OTHER INFORMATION: Description of Artificial Sequence:PRIMER

<400> SEQUENCE: 15
agcttgcatg cctccaggtc gactctagag cccgggtacc gagctcgaat tc            52

<210> SEQ ID NO 16
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: PRIMER
<220> FEATURE:
<223> OTHER INFORMATION: Description of Artificial Sequence:PRIMER

<400> SEQUENCE: 16
gacggatccg tggaatattt cggatatcc                                       29

<210> SEQ ID NO 17
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: PRIMER
<220> FEATURE:
<223> OTHER INFORMATION: Description of Artificial Sequence:PRIMER

<400> SEQUENCE: 17
ctcggatccg gacggattac aacaggtatt gtcc                                 34

<210> SEQ ID NO 18
<211> LENGTH: 31
<212> TYPE: DNA
<213> ORGANISM: Artificial Sequence
<220> FEATURE:
<221> NAME/KEY: misc_feature
<222> LOCATION: (1)..(31)
```

<223> OTHER INFORMATION: PRIMER
<220> FEATURE:
<223> OTHER INFORMATION: Description of Artificial Sequence:PRIMER

<400> SEQUENCE: 18
cagaattcac catggccgtg acttcctcct c                              31

<210> SEQ ID NO 19
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: PRIMER
<220> FEATURE:
<223> OTHER INFORMATION: Description of Artificial Sequence:PRIMER

<400> SEQUENCE: 19
caagatctca tacattcaat cctcatggac ac                             32

<210> SEQ ID NO 20
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: PRIMER
<220> FEATURE:
<223> OTHER INFORMATION: Description of Artificial Sequence:PRIMER

<400> SEQUENCE: 20
gagaattctt aacacgcatg atccccacgg c                              31

<210> SEQ ID NO 21
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: PRIMER
<220> FEATURE:
<223> OTHER INFORMATION: Description of Artificial Sequence:PRIMER

<400> SEQUENCE: 21
ctggatccgt caaatccgtg aatcgtaacg ag                             32

<210> SEQ ID NO 22
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: PRIMER
<220> FEATURE:
<223> OTHER INFORMATION: Description of Artificial Sequence:PRIMER

<400> SEQUENCE: 22
ggccggatcc atattacgta gaaatggctt cag                            33

<210> SEQ ID NO 23
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: PRIMER
<220> FEATURE:
<223> OTHER INFORMATION: Description of Artificial Sequence:PRIMER

<400> SEQUENCE: 23
gccgctcgag ggtccttatc tagtttg                                              27

<210> SEQ ID NO 24
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: PRIMER
<220> FEATURE:
<223> OTHER INFORMATION: Description of Artificial Sequence:PRIMER

<400> SEQUENCE: 24
tctagaggca cctgtcactt tggaaaaaaa atatacgc                                  38

<210> SEQ ID NO 25
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: PRIMER
<220> FEATURE:
<223> OTHER INFORMATION: Description of Artificial Sequence:PRIMER

<400> SEQUENCE: 25
ccgcgggccg gaaatgctct ctgttc                                               26

<210> SEQ ID NO 26
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: PRIMER
<220> FEATURE:
<223> OTHER INFORMATION: Description of Artificial Sequence:PRIMER

<400> SEQUENCE: 26
cacgtcgacc attcaaactt tactac                                               26

<210> SEQ ID NO 27
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: PRIMER
<220> FEATURE:
<223> OTHER INFORMATION: Description of Artificial Sequence:PRIMER

<400> SEQUENCE: 27
gagggcccgg tccagacat                                                       19

<210> SEQ ID NO 28
<211> LENGTH: 27
<212> TYPE: DNA
<213> ORGANISM: Artificial Sequence
<220> FEATURE:

-continued

```
<221> NAME/KEY: misc_feature
<222> LOCATION: (1)..(27)
<223> OTHER INFORMATION: PRIMER
<220> FEATURE:
<223> OTHER INFORMATION: Description of Artificial Sequence:PRIMER

<400> SEQUENCE: 28
cccgggtatt gagcacgtga gtatacg                                              27

<210> SEQ ID NO 29
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: PRIMER
<220> FEATURE:
<223> OTHER INFORMATION: Description of Artificial Sequence:PRIMER

<400> SEQUENCE: 29
ggatccggca agtgcacaaa caatac                                               26

<210> SEQ ID NO 30
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: PRIMER
<220> FEATURE:
<223> OTHER INFORMATION: Description of Artificial Sequence:PRIMER

<400> SEQUENCE: 30
ccaaatataa ctcgagcttt g                                                    21

<210> SEQ ID NO 31
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: PRIMER
<220> FEATURE:
<223> OTHER INFORMATION: Description of Artificial Sequence:PRIMER

<400> SEQUENCE: 31
gcaaagtcca ccaccgcag                                                       19

<210> SEQ ID NO 32
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: PRIMER
<220> FEATURE:
<223> OTHER INFORMATION: Description of Artificial Sequence:PRIMER

<400> SEQUENCE: 32
gccacgtgcc cccgggtttc tctagcc                                              27

<210> SEQ ID NO 33
<211> LENGTH: 33
<212> TYPE: DNA
<213> ORGANISM: Artificial Sequence
```

```
<220> FEATURE:
<221> NAME/KEY: misc_feature
<222> LOCATION: (1)..(33)
<223> OTHER INFORMATION: PRIMER
<220> FEATURE:
<223> OTHER INFORMATION: Description of Artificial Sequence:PRIMER

<400> SEQUENCE: 33
ggaaaagagc tcgataatta ttgatgatag atc                          33

<210> SEQ ID NO 34
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: PRIMER
<220> FEATURE:
<223> OTHER INFORMATION: Description of Artificial Sequence:PRIMER

<400> SEQUENCE: 34
ccgttttgga tcctagatca g                                       21

<210> SEQ ID NO 35
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: PRIMER
<220> FEATURE:
<223> OTHER INFORMATION: Description of Artificial Sequence:PRIMER

<400> SEQUENCE: 35
gttcccgggt tattgtcctg catttg                                  26

<210> SEQ ID NO 36
<211> LENGTH: 28
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: PRIMER
<220> FEATURE:
<223> OTHER INFORMATION: Description of Artificial Sequence:PRIMER

<400> SEQUENCE: 36
aagagctcat ctgataatag atcaagcg                                28

<210> SEQ ID NO 37
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: PRIMER
<220> FEATURE:
<223> OTHER INFORMATION: Description of Artificial Sequence:PRIMER

<400> SEQUENCE: 37
aggagctcaa cgacaataaa tggctg                                  26

<210> SEQ ID NO 38
<211> LENGTH: 24
<212> TYPE: DNA
```

```
<213> ORGANISM: Artificial Sequence
<220> FEATURE:
<221> NAME/KEY: misc_feature
<222> LOCATION: (1)..(24)
<223> OTHER INFORMATION: PRIMER
<220> FEATURE:
<223> OTHER INFORMATION: Description of Artificial Sequence:PRIMER

<400> SEQUENCE: 38
gtcctctaga tcttgaatga aatc                                            24

<210> SEQ ID NO 39
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: PRIMER
<220> FEATURE:
<223> OTHER INFORMATION: Description of Artificial Sequence:PRIMER

<400> SEQUENCE: 39
ctttgagctc gtacaagaag cag                                             23

<210> SEQ ID NO 40
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: PRIMER
<220> FEATURE:
<223> OTHER INFORMATION: Description of Artificial Sequence:PRIMER

<400> SEQUENCE: 40
ctaagctttg cgcccgtgaa g                                               21

<210> SEQ ID NO 41
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: PRIMER
<220> FEATURE:
<223> OTHER INFORMATION: Description of Artificial Sequence:PRIMER

<400> SEQUENCE: 41
gttctagaag ttttcaaagc agag                                            24

<210> SEQ ID NO 42
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: PRIMER
<220> FEATURE:
<223> OTHER INFORMATION: Description of Artificial Sequence:PRIMER

<400> SEQUENCE: 42
gggattcgaa ttctgtcgcg ctgtaac                                         27

<210> SEQ ID NO 43
<211> LENGTH: 28
```

```
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: PRIMER
<220> FEATURE:
<223> OTHER INFORMATION: Description of Artificial Sequence:PRIMER

<400> SEQUENCE: 43
tgggatccgt aacggcttta gcgagctg                                  28

<210> SEQ ID NO 44
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: PRIMER
<220> FEATURE:
<223> OTHER INFORMATION: Description of Artificial Sequence:PRIMER

<400> SEQUENCE: 44
gattccgcgt aaggatcccg                                           20

<210> SEQ ID NO 45
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: PRIMER
<220> FEATURE:
<223> OTHER INFORMATION: Description of Artificial Sequence:PRIMER

<400> SEQUENCE: 45
ccagcatcta gaccaccag                                            19

<210> SEQ ID NO 46
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: PRIMER
<220> FEATURE:
<223> OTHER INFORMATION: Description of Artificial Sequence:PRIMER

<400> SEQUENCE: 46
gactgcagct ggccgctggg tattctgtcg tagtt                          35

<210> SEQ ID NO 47
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: PRIMER
<220> FEATURE:
<223> OTHER INFORMATION: Description of Artificial Sequence:PRIMER

<400> SEQUENCE: 47
gatctagatc acgcgtacgc agaaggtttt gc                             32

<210> SEQ ID NO 48
```

```
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: PRIMER
<220> FEATURE:
<223> OTHER INFORMATION: Description of Artificial Sequence:PRIMER

<400> SEQUENCE: 48
gaattccaat tcagcgggta acctt                                          25

<210> SEQ ID NO 49
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: PRIMER
<220> FEATURE:
<223> OTHER INFORMATION: Description of Artificial Sequence:PRIMER

<400> SEQUENCE: 49
aagctttgct tgaacccaaa agggcggta                                      29

<210> SEQ ID NO 50
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: PRIMER
<220> FEATURE:
<223> OTHER INFORMATION: Description of Artificial Sequence:PRIMER

<400> SEQUENCE: 50
gcattgagtt gctgcaggct tccttcttgg tcgcc                               35

<210> SEQ ID NO 51
<211> LENGTH: 35
<212> TYPE: DNA
<213> ORGANISM: Artificial Sequence
<220> FEATURE:
<221> NAME/KEY: misc_difference
<222> LOCATION: (1)..(35)
<223> OTHER INFORMATION: PRIMER
<220> FEATURE:
<223> OTHER INFORMATION: Description of Artificial Sequence:PRIMER

<400> SEQUENCE: 51
ggcgaccaag aaggaagcct gcagcaactc aatgc                               35
```